US011305024B2

(12) United States Patent
Yantasee et al.

(10) Patent No.: US 11,305,024 B2
(45) Date of Patent: *Apr. 19, 2022

(54) CROSS-LINKED POLYMER MODIFIED NANOPARTICLES

(71) Applicants: OREGON HEALTH & SCIENCE UNIVERSITY, Portland, OR (US); PDX Pharmaceuticals, Inc., Portland, OR (US)

(72) Inventors: Wassana Yantasee, Lake Oswego, OR (US); Worapol Ngamcherdtrakul, Portland, OR (US); Jingga Morry, Portland, OR (US); David Castro, Portland, OR (US); Joe William Gray, Lake Oswego, OR (US)

(73) Assignees: Oregon Health & Science University, Portland, OR (US); PDX Pharmaceuticals, Inc., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/398,954

(22) Filed: Aug. 10, 2021

(65) Prior Publication Data

US 2021/0393806 A1    Dec. 23, 2021

Related U.S. Application Data

(63) Continuation of application No. 15/429,971, filed on Feb. 10, 2017, now Pat. No. 11,207,428, which is a continuation of application No. PCT/US2016/022655, filed on Mar. 16, 2016.

(60) Provisional application No. 62/133,913, filed on Mar. 16, 2015.

(51) Int. Cl.

| A61K 49/00 | (2006.01) |
|---|---|
| A61K 31/713 | (2006.01) |
| A61K 49/18 | (2006.01) |
| A61K 47/60 | (2017.01) |
| A61K 47/59 | (2017.01) |
| A61K 47/69 | (2017.01) |
| A61K 47/68 | (2017.01) |
| A61K 47/55 | (2017.01) |
| A61K 38/16 | (2006.01) |
| B82Y 30/00 | (2011.01) |
| B82Y 5/00 | (2011.01) |

(52) U.S. Cl.
CPC ........ *A61K 49/0093* (2013.01); *A61K 31/713* (2013.01); *A61K 38/16* (2013.01); *A61K 47/551* (2017.08); *A61K 47/59* (2017.08); *A61K 47/60* (2017.08); *A61K 47/6849* (2017.08); *A61K 47/6855* (2017.08); *A61K 47/6923* (2017.08); *A61K 47/6929* (2017.08); *A61K 49/186* (2013.01); *A61K 49/1857* (2013.01); *A61K 49/1875* (2013.01); *B82Y 5/00* (2013.01); *B82Y 30/00* (2013.01)

(58) Field of Classification Search
None
See application file for complete search history.

(56) References Cited

U.S. PATENT DOCUMENTS

| 7,045,356 | B2 | 5/2006 | Trubetskoy et al. |
|---|---|---|---|
| 9,884,026 | B2 | 2/2018 | Fahmy et al. |
| 2003/0018002 | A1 | 1/2003 | Sagara |
| 2003/0059465 | A1 | 3/2003 | Unger et al. |
| 2006/0293396 | A1 | 12/2006 | Bringley et al. |
| 2007/0184068 | A1 | 8/2007 | Renner et al. |
| 2008/0161547 | A1 | 7/2008 | Khvorova et al. |
| 2008/0279954 | A1 | 11/2008 | Davis et al. |
| 2009/0110719 | A1 | 4/2009 | Roy et al. |
| 2011/0275704 | A1 | 11/2011 | Troiano et al. |
| 2012/0027820 | A1 | 2/2012 | Troiano et al. |
| 2012/0207795 | A1 | 8/2012 | Zink et al. |
| 2013/0337067 | A1 | 12/2013 | Prakash et al. |
| 2017/0173169 | A1 | 6/2017 | Yantasee et al. |

FOREIGN PATENT DOCUMENTS

WO    WO2017120537    7/2017

OTHER PUBLICATIONS

Argyo, et al., "Multifunctional mesoporous silica nanoparticles as a universal platform for drug delivery," Chem. Mater., vol. 26, No. 1, 2014, pp. 435-451.
Barbe, et al., "Silica Particles: A Novel Drug-Delivery System," Advanced Materials, vol. 16, 2004, pp. 1959-1966.
Bartlett, et al., "Impact of tumor-specific targeting on the biodistribution and efficacy of siRNA nanoparticles measured by multimodality in vivo imaging," PNAS USA, vol. 104, No. 39, 2007, pp. 15549-15554.
Bharali, et al., "Organically modified silica nanoparticles: A nonviral vector for in vivo gene delivery and expression in the brain," PNAS, vol. 102, No. 32, 2005, pp. 11539-11544.
Breunig, et al., "Breaking up the correlation between efficacy and toxicity for nonviral gene delivery," PNAS, vol. 104, No. 36, 2007, pp. 14454-14459.
Bringley, et al., "Controlled, simultaneous assembly of polyethylenimine onto nanoparticle silica colloids," Langmuir., vol. 22, No. 9, 2006, pp. 4198-4207.

(Continued)

*Primary Examiner* — Michael G. Hartley
*Assistant Examiner* — Lance W Rider
(74) *Attorney, Agent, or Firm* — Tanya M. Harding; C. Rachal Winger; Lee & Hayes, PC

(57) ABSTRACT

Disclosed herein are nanoconstructs comprising a nanoparticle, coated with additional agents such as cationic polymers, stabilizers, targeting molecules, labels, oligonucleotides and small molecules. These constructs may be used to deliver compounds to treat solid tumors and to diagnose cancer and other diseases. Further disclosed are methods of making such compounds and use of such compounds to treat or diagnose human disease.

30 Claims, 38 Drawing Sheets

Specification includes a Sequence Listing.

(56) References Cited

OTHER PUBLICATIONS

Buchman, et al., "Silica nanoparticles and polyethyleneimine (PEI)-mediated functionalization: a new method of PEI covalent attachment for siRNA delivery applications," Bioconjugate Chemistry, vol. 24, No. 12, 2013, pp. 2076-2087.

Choi & Lee, "Enhanced gene delivery using disulfide-crosslinked low molecular weight polyethylenimine with listeriolysin o-polyethylenimine disulfide conjugate," J. Control. Release, vol. 131, No. 1, 2008, pp. 70-76.

Crist, et al., "Common pitfalls in nanotechnology: lessons learned from NCI's Nanotechnology Characterization Laboratory," Integr. Biol. (Camb)., vol. 5, No. 1, 2013, pp. 66-73.

Davis, Mark, "The first targeted delivery of siRNA in humans via a self-assembling, cyclodextrin polymerbased nanoparticle: from concept to clinic," Mol. Pharm., vol. 6, No. 3, 2009, pp. 659-668.

Dekker, Robert, "Immobilization of a Lactase onto a Magnetic Support by Covalent Attachment to Polyethyleneimine-Glutaraldehyde-Activated Magnetite," Applied Biochemstry and Biotechnology, vol. 22, 1989, pp. 289-310.

Gref, et al., "'Stealth' corona-core nanoparticles surface modified by polyethylene glycol (PEG): influences of the corona (PEG chain length and surface density) and of the core composition on phagocytic uptake and plasma protein adsorption," Colloids and Surface B Biointerfaces, vol. 18, No. 3-4, 2000, pp. 301-313.

Gu, et al., "Therapeutic siRNA for drug-resistant HER2-positive breast cancer," Oncotarget, vol. 7, No. 12, 2016, pp. 14727-14741.

Hatakeyama, et al., "Assessment of in vivo siRNA delivery in cancer mouse models," Methods Mol. Biol., vol. 1402, 2016, pp. 189-197.

Haussecker, Dirk, "The Business of RNAi Therapeutics in 2012," Mol. Ther. Nucleic Acids, vol. 2, No. 8, 2012, 12 pages.

Kanasty, et al. "Delivery materials for siRNA therapeutics," Nat. Mater., vol. 12, No. 11, 2013, pp. 967-977.

Kim & Kim, "Bioreducible polymers for gene delivery," React. Funct. Polym., vol. 71, No. 3, 2011, pp. 344-349.

Koopaei, et al., "Docetaxel immunonanocarriers as targeted delivery systems for HER 2-positive tumor cells: preparation, characterization, and cytotoxicity studies," Int. J. Nanomedicine, vol. 6, 2011, pp. 1903-1912.

Lee, et al., "Controlled synthesis of PEI-coated gold nanoparticles using reductive catechol chemistry for siRNA delivery," J. Cont. Release, vol. 155, No. 1, 2011, pp. 3-10.

Li, et al., "GALA: a designed synthetic pH-responsive amphipathic peptide with applications in drug and gene delivery," Adv. Drug Deliv. Rev., vol. 56, No. 7, 2004, pp. 967-985.

Lin, et al., "Intracellular cleavable poly(2-dimethylaminoethyl methacrylate) functionalized mesoporous silica nanoparticles for efficient siRNA delivery in vitro and in vivo," Nanoscale, vol. 5, No. 10, 2013, pp. 4291-4301.

Maeda, et al., "Tumor vascular permeability and the EPR effect in macromolecular therapeutics: a review," J. Control Release, vol. 65, No. 1-2, 2000, pp. 271-284.

Mao, et al., "Influence of Polyethylene Glycol Chain Length on the Physicochemical and Biological Properties of Poly (ethylene imine)-graft-Poly(ethylene glycol) Block Copolymer/SiRNA Polyplexes," Bioconjugate Chem., vol. 17, No. 5, 2006, pp. 1209-1218.

Meng, et al., "Use of size and a copolymer design feature to improve the biodistribution and the enhanced permeability and retention effect of doxorubicin-loaded mesoporous silica nanoparticles in a murine xenograft tumor model," ACS Nano, vol. 5, No. 5, 2011, pp. 4131-4144.

Milicic, et al., "Small Cationic DDA:TDB Liposomes as Protein Vaccine Adjuvants Obviate the Need for TLR Agonists in Inducing Cellular and Humoral Responses," PLoS One, vol. 7, No. 3, 2012, 10 pages.

Mitra, et al., "Novel epithelial cell adhesion molecule antibody conjugated polyethyleneimine-capped gold nanoparticles for enhanced and targeted small interfering RNA delivery to retinoblastoma cells," Mol. Vis., vol. 19, 2013, pp. 1029-1038.

Morry, et al., "Dermal delivery of HSP47 siRNA with NOX4-modulating mesoporous silica-based nanoparticles for treating fibrosis," Biomaterials, vol. 66, 2015, pp. 41-52.

Morry, et al., "Oxidative stress in cancer and fibrosis: Opportunity for therapeutic intervention with antioxidant compounds, enzymes, and nanoparticles," Redox Biol., vol. 11, 2017, pp. 240-253.

Morry, et al., "Targeted Treatment of Metastatic Breast Cancer by PLK1 siRNA Delivered by an Antioxidant Nanoparticle Platform," Mol. Cancer Ther., vol. 16, No. 4, 2017, pp. 763-772.

Neu, et al., "Bioreversibly crosslinked polyplexes of PEI and high molecular weight PEG show extended circulation times in vivo," J. Contr. Release, vol. 124, No. 1-2, 2007, pp. 69-80.

Ngamcherdtrakul, et al., "Cationic Polymer Modified Mesoporous Silica Nanoparticles for Targeted siRNA Delivery to HER2+ Breast Cancer," Advanced Functional Materials, vol. 25, 2015, pp. 2646-2659.

Ngamcherdtrakul, et al., "Current development of targeted oligonucleotide-based cancer therapies: Perspective on HER2-positive breast cancer treatment," Cancer Treatment Reviews, vol. 45, 2016, pp. 19-29.

Pan, et al., "Nuclear-targeted drug delivery of TAT peptide-conjugated monodisperse mesoporous silica nanoparticles," Journal of American Chemical Society, vol. 13, No. 13, 2012, pp. 5722-5725.

Park, et al., "Clustered Magnetite Nanocrystals Cross-Linked with PEI for Efficient siRNA Delivery," Biomacromolecules, vol. 12, No. 2, 2011 pp. 457-465.

Saraswathy & Oupicky, "Chapter 13: Endolysosomal Escape into Cytosol," CRC Press—Taylor & Francis Group, Boca Raton, FL, USA, 2016, pp. 341-365.

Shao, et al., "Nanoparticle-Based Immunotherapy for Cancer," ACS Nano, vol. 9, No. 1, 2015, pp. 16-30.

Shen, et al., "Cyclodextrin and polyethylenimine functionalized mesoporous silica nanoparticles for delivery of siRNA cancer therapeutics," Theranostics, vol. 4, No. 5, 2014, pp. 487-497.

Slowing, et al., "Mesoporous Silica Nanoparticles for Drug Delivery and Biosensing Applications," Advanced Functional Materials, vol. 17, No. 8, 2007, pp. 1225-1236.

Tang, et al., "Mesoporous silica nanoparticles: synthesis, biocompatibility and drug delivery," Adv. Mater., vol. 24, No. 12, 2012, pp. 1504-1534.

Tarn, et al., "Mesoporous Silica Nanoparticle Nanocarriers: Biofunctionality and Biocompatibility," Accounts of Chemical Research, vol. 46, No. 3, 2013, pp. 792-801.

Towns & Regnier, "Polyethyleneimine-bonded phases in the separation of proteins by capillary electrophoresis," Journal of Chromatography, vol. 516, No. 1, 1990, pp. 69-78.

Xia, et al., "Cationic Polystyrene Nanosphere Toxicity Depends on Cell-Specific Endocytic and Mitochondrial Injury Pathways," ACS Nano, vol. 2, No. 1, 2008, pp. 85-96.

Xia, et al., "Polyethyleneimine Coating Enhances the Cellular Uptake of Mesoporous Silica Nanoparticles and Allows Safe Delivery of siRNA and DNA Constructs," ACS Nano, vol. 3, No. 10, 2009, pp. 3273-3286.

Yantasee, et al., "Removal of Heavy Metals from Aqueous Systems with Thiol Functionalized Superparamagnetic Nanoparticles," Environ Sci. Technol., vol. 41, No. 14, 2007, pp. 5114-5119.

Yousefpour, et al., "Targeted delivery of doxorubicin-utilizing chitosan nanoparticles surface-functionalized with anti-Her2 trastuzumab," Int. J. Nanomedicine, vol. 6, 2011, pp. 1977-1990.

Zhang, et al., "Differential Expression of Syndecan-1 Mediates Cationic Nanoparticle Toxicity in Undifferentiated versus Differentiated Normal Human Bronchial Epithelial Cells," ACS Nano, vol. 5, No. 4, 2011, pp. 2756-2769.

Zhang, et al., "Synthesis of poly(ethylene glycol) (PEG)-grafted colloidal silica particles with improved stability in aqueous solvents," J. Colloid. Interface Sci., vol. 310, No. 2, 2007, pp. 446-455.

LM2-4luc+/H2N
(2 days post-treatment)

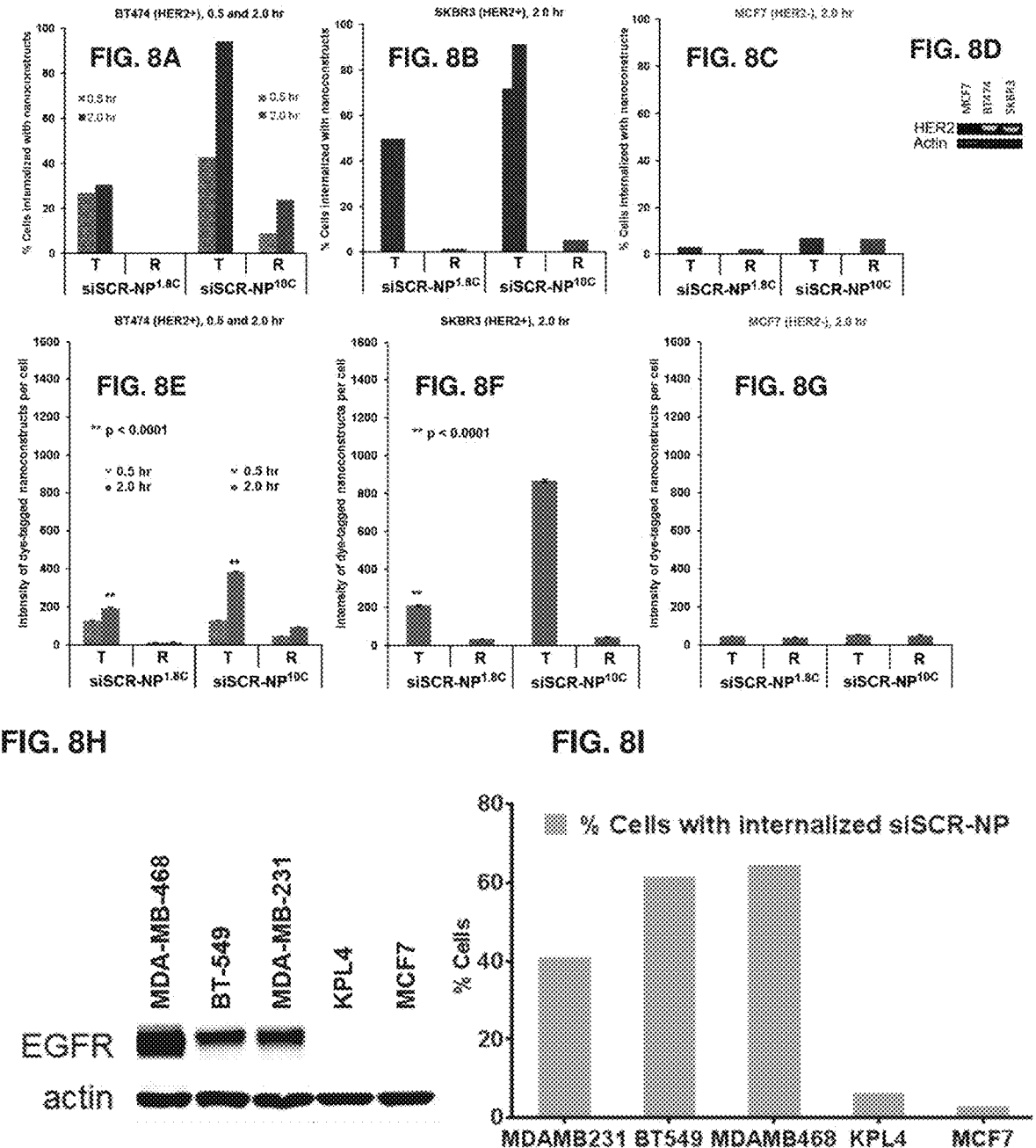

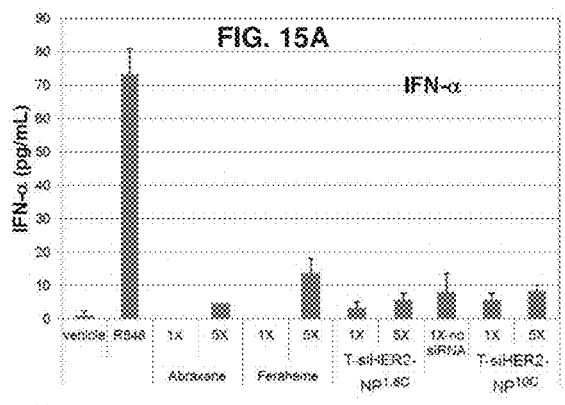
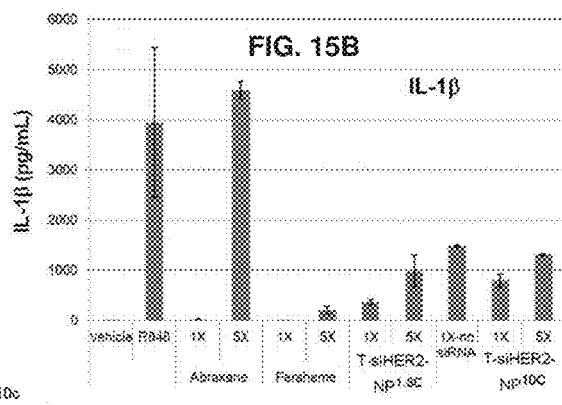
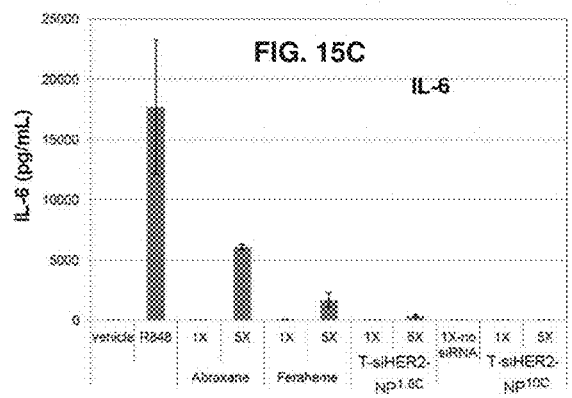
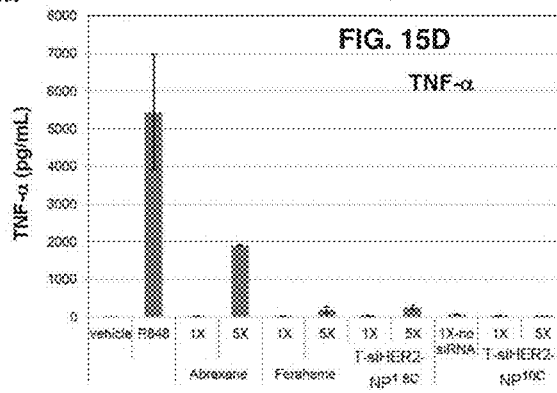
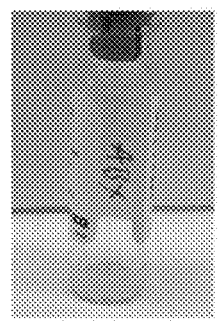

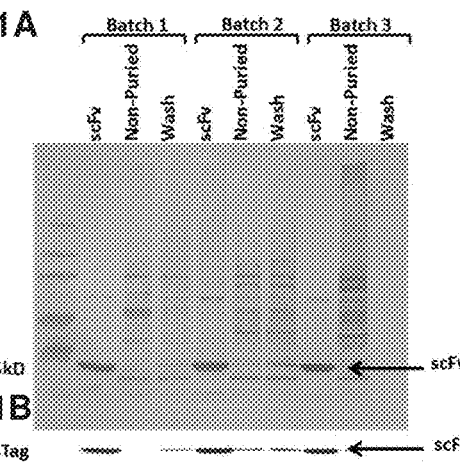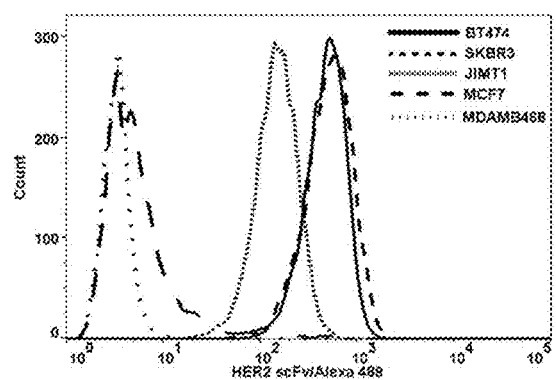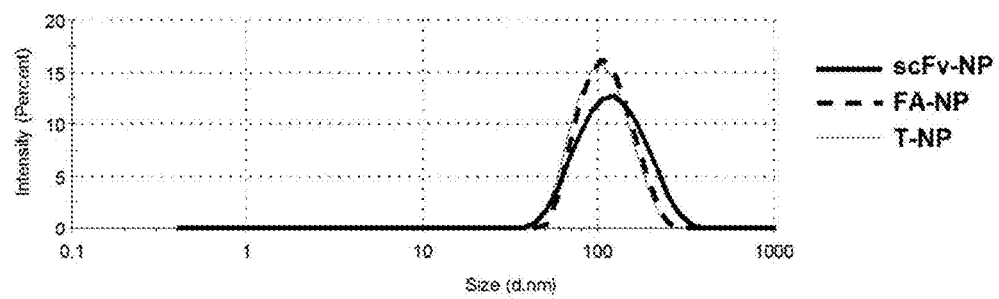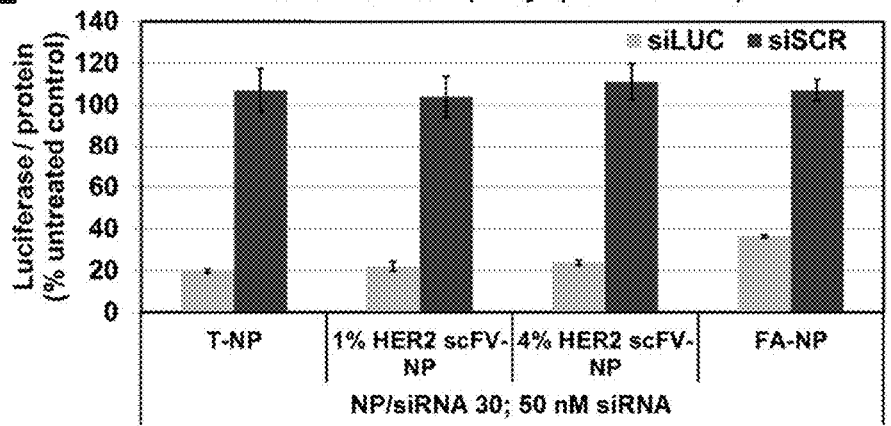

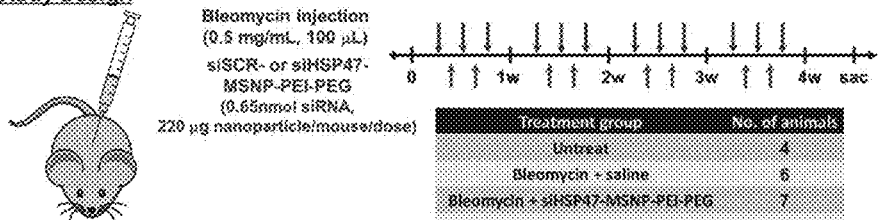
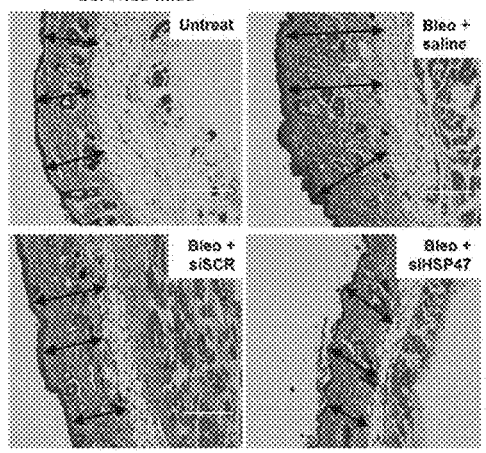
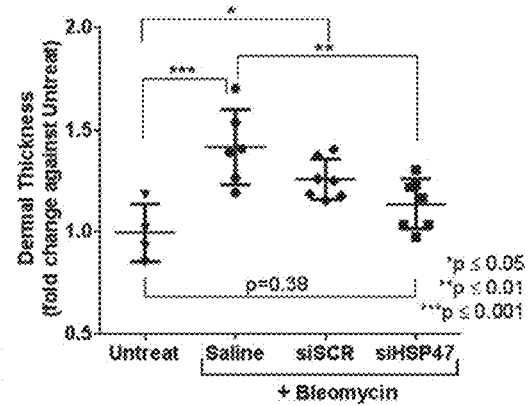
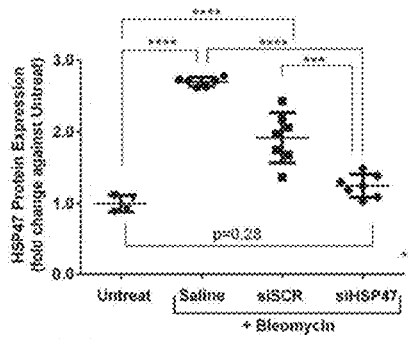
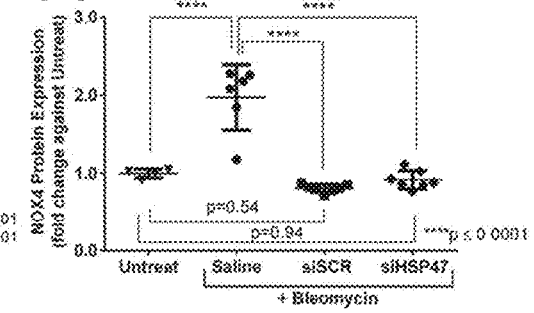
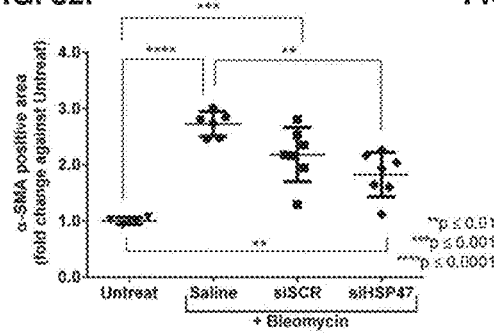
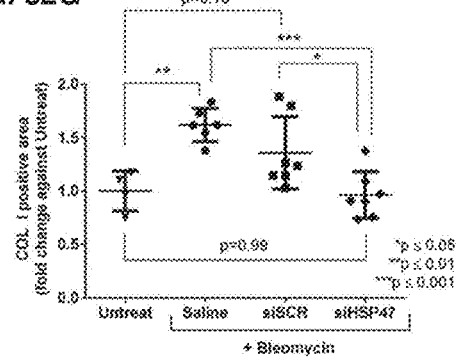

FIG. 34A
FIG. 34B
FIG. 34C
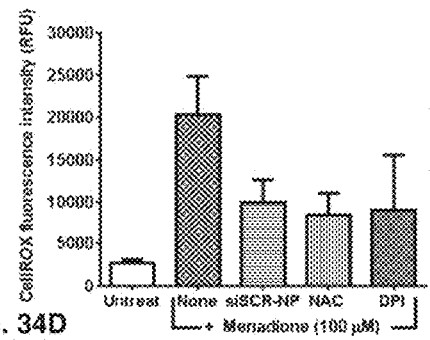
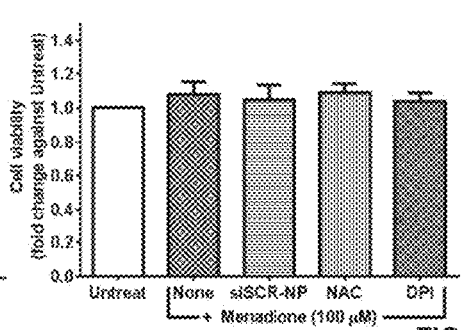
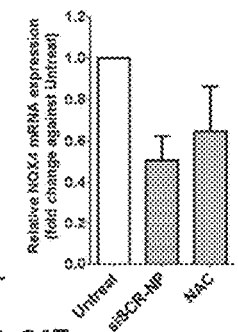
FIG. 34D
FIG. 34E
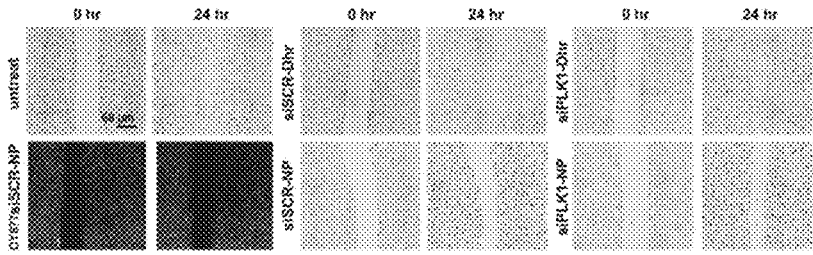
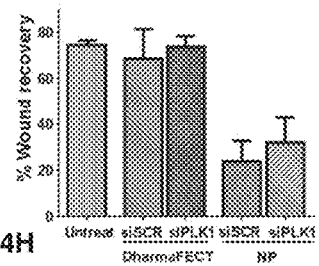
FIG. 34F
FIG. 34G
FIG. 34H
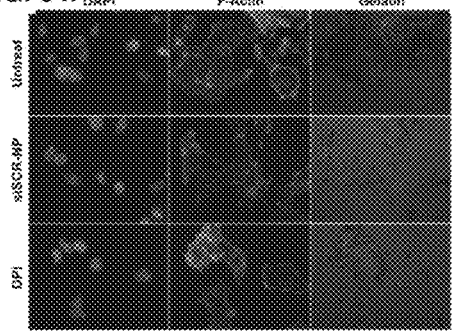
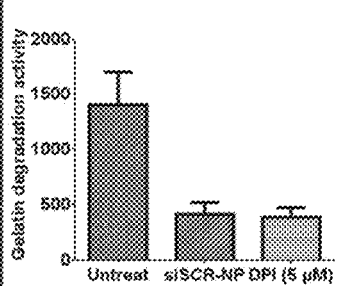
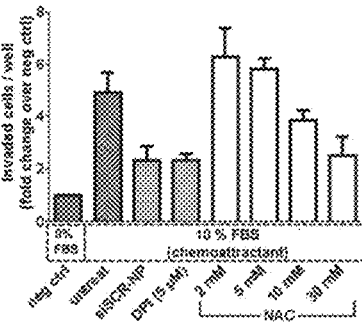

FIG. 35A
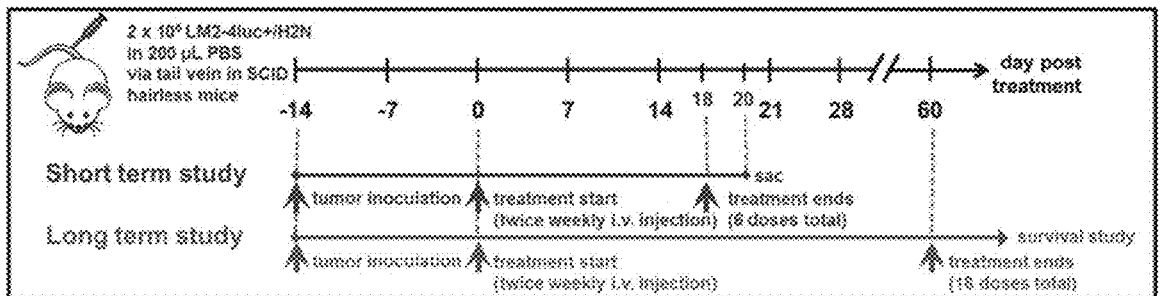
FIG. 35B
| Group | Parameter | Brain | Lung | Liver | Spleen | Kidney | Lymph nodes | Spine | Peritoneal/Pleural | Total tumor signal | Ratio over saline |
|---|---|---|---|---|---|---|---|---|---|---|---|
| Saline | Incidence rate | 2/5 | 5/5 | 2/5 | 1/5 | 1/5 | 4/5 | 3/5 | 1/5 | | |
| | Tumor signal | 288 | 76 | 73 | 16 | 12 | 103 | 1550 | 4 | 2121 | 1.00 |
| T-siSCR-NP | Incidence rate | 1/5 | 4/5 | - | - | - | 4/5 | 4/5 | 1/5 | | |
| | Tumor signal | 141 | 155 | - | - | - | 131 | 1322 | 13 | 1763 | 0.83 |
| T-siPLK1-NP | Incidence rate | - | 3/5 | - | - | - | 1/5 | 2/5 | 2/5 | | |
| | Tumor signal | - | 19 | - | - | - | 3 | 924 | 8 | 954 | 0.45 |
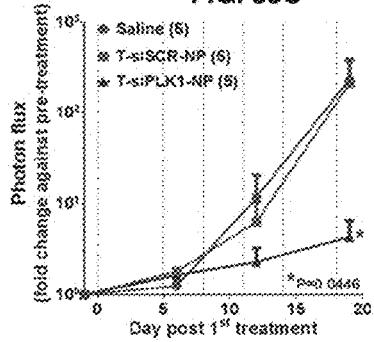
FIG. 35C
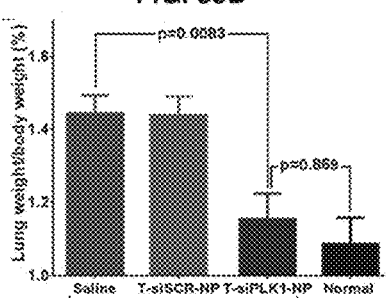
FIG. 35D
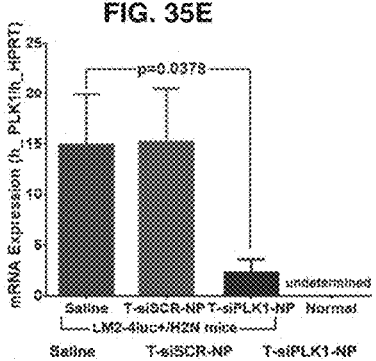
FIG. 35E
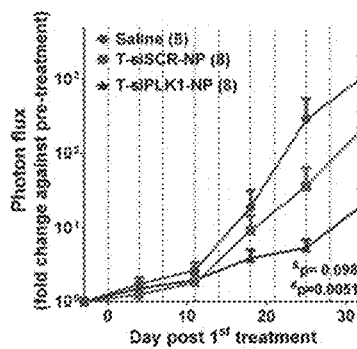
FIG. 35F
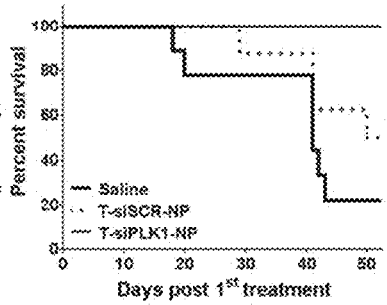
FIG. 35G
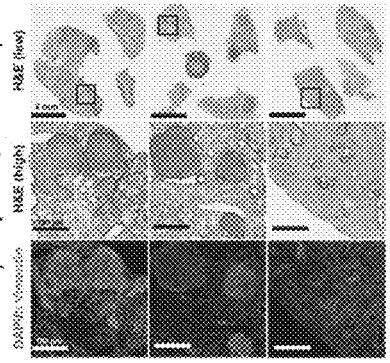
FIG. 35H

CROSS-LINKED POLYMER MODIFIED NANOPARTICLES

CROSS-REFERENCE TO RELATED APPLICATION

This is a continuation of co-pending U.S. patent application Ser. No. 15/429,971, filed Feb. 10, 2017; which is a continuation of PCT/US2016/022655, filed Mar. 16, 2016; which claims priority to and the benefit of the earlier filing date of U.S. Provisional Application No. 62/133,913, filed Mar. 16, 2015. Each of these earlier related applications is incorporated by reference herein in its entirety.

STATEMENT OF GOVERNMENT INTEREST

This invention was made with the support of the United States government under the terms of grant numbers R01GM089918, and R41DK094571, as well as contract number HHSN261201300078C awarded by the National Institutes of Health. The United States government has certain rights in this invention.

BACKGROUND

A wide variety of molecular architectures have been developed for the treatment of human pathologies, yet the inability to effectively deliver such molecules to their intended biological target has hindered their implementation as therapeutic modalities. Oligonucleotides, proteins, antibodies and antigen-binding fragments thereof, peptides, and small molecules alike have often exhibited poor penetration through biological barriers, or stability in metabolically active systems. In spite of the often promising in vitro characteristics of compounds within these classes, their inability to elicit therapeutic phenotypes has inspired attempts to enhance their delivery and stability in vivo.

For instance, RNA therapeutics represent a promising class of compounds for modulating gene expression. RNA oligonucleotides, such as small interfering RNA (siRNA) and micro RNA (miRNA), while often effective in vitro, may experience short circulation half-life and difficulty penetrating extracellular and intracellular barriers. The same phenomenon has been observed for peptidic therapeutics, such as small proteins, antibodies and antigen-binding fragments thereof, and peptides, as well as a variety of small molecules.

To address these challenges, a variety of particle-based technologies have been developed with the aim of producing agents capable of improving the biological delivery and stability of the above molecules. For instance, a wide range of organic and inorganic nanoparticle materials such as viral-capsids, cyclodextrin, cationic polymers, gold nanoparticles, peptides (R. Kanasty et al., 2013; D. Haussecker, 2012) and mesoporous silica nanoparticles (MSNP) (C. Argyo et al., 2013; F. Tang et al., 2012) have been evaluated as siRNA carriers with the potential to increase siRNA half-life in the blood, allow escape from the reticuloendothelial system, and enhance tumor specific cellular uptake. However, none of the nanoconstructs have achieved a desirable therapeutic index in clinics for treating solid tumors at sites other than the liver.

Attempts to improve tumor accumulation have exploited passive delivery using the enhanced permeability and retention (EPR) effect of tumors (H. Maeda et al., 2000). It was found that attachment of cationic polymers including polyethylenimine-cyclodextrin (J. Shen et al., 2014) and poly(2-dimethylaminoethyl methacrylate) (PDMAEMA) (D. Lin et al., 2013) increased cellular uptake of mesoporous silica nanoparticles. While promising, significant anti-tumor activity in vivo has not been reported for these constructs (J. Shen et al., 2014, D. Lin et al., 2013).

There is therefore an unmet need for nanoparticle constructs capable of improving the delivery and stability of therapeutic compounds in vivo, such as oligonucleotides (e.g., siRNA or miRNA), small proteins, peptides, and small molecules.

SUMMARY OF THE INVENTION

In one aspect, the invention features a nanoconstruct that contains a cationic polymer bound to an exterior surface of a nanoparticle, wherein the cationic polymer is cross-linked. The nanoconstruct may further include a stabilizer bound to the cationic polymer or nanoparticle, for instance, to prevents aggregation of the nanoconstruct in solution. In some embodiments, the nanoparticle is mesoporous, such as a mesoporous silica nanoparticle. The nanoparticle may be a silica nanoparticle, a silicon nanoparticle, an iron oxide nanoparticle, a gold nanoparticle, a silver nanoparticle, or a carbon nanotube, e.g., a mesoporous silica nanoparticle or an iron oxide nanoparticle.

The nanoconstruct may have a hydrodynamic diameter of from about 10 to about 200 nm. In some embodiments, the nanoparticle has a diameter of 5 to 90 nm. In some embodiments, the exterior surface of the nanoparticle includes thiol, amine, carboxylate, or phosphonate functional groups.

In some embodiments, the cationic polymer is from about 5% to about 30% by weight of the nanoconstruct. In some embodiments, the cationic polymer is from about 10% to about 25% by weight of the nanoconstruct. The cationic polymer may be polyethylenimine (PEI), chitosan, polypropyleneimine, polylysine, polyamidoamine, poly(allylamine), poly(diallyldimethylammonium chloride), poly(N-isopropyl acrylamide-co-acrylamide), poly(N-isopropyl acrylamide-co-acrylic acid), diethylaminoethyl-dextran, poly-(N-ethyl-vinylpyridinium bromide), poly(dimethylamino)ethyl methacrylate, and/or poly(ethylene glycol)-co-poly(trimethylaminoethylmethacrylate chloride). In some embodiments, the polyethylenimine has a molecular weight of from about 0.8 kDa to about 10 kDa. The cationic polymer may be cross-linked by reacting cationic polymer on the surface of the nanoparticle with a cross-linker in the presence of cationic polymer in solution, e.g., to prevent or reduce aggregation of nanoconstructs.

In some embodiments, the stabilizer is from about 1% to about 30% by weight of the nanoconstruct. For instance, the stabilizer may be from about 5% to about 25% by weight of the nanoconstruct. The stabilizer may be polyethylene glycol (PEG), dextran, polysialic acid, hyaluronic acid (HA), polyvinyl pyrrolidone (PVP), polyvinyl alcohol (PVA), and polyacrylamide (PAM). The polyethylene glycol may have a molecular weight of from about 1 kDa to about 20 kDa.

In some embodiments, the nanoconstruct includes at least one type of oligonucleotide, e.g., siRNA, miRNA, miRNA mimic, or antisense oligomer, electrostatically bound to the cationic polymer. In some embodiments, the at least one type of oligonucleotide is siRNA, e.g., that targets one or more genes selected from the group consisting of HER2, AKT1, AKT2, AKT3, EPS8L1, GRB7, AR, Myc, VEGF, VEGF-R1, RTP801, proNGF, Keratin K6A, Bcl-2, PLK1, LMP2, LMP7, MECL1, RRM2, PKN3, Survivin, HIF1α, Furin, KSP, eiF-4E, p53, β-catenin, ApoB, PCSK9, HSP47, CFTR, CTGF, SNALP, RSV nucleocapsids, CD47, PD-L1, and CTLA-4. The at least one type of oligonucleotide may be from about 1% to about 15% by weight of the nanoconstruct. In some embodiments, the at least one type of oligonucleotide is from about 1% to about 5% by weight of the nanoconstruct. The at least one type of oligonucleotide may include two or more different siRNAs loaded onto the nanoconstruct.

In some embodiments, the nanoconstruct further includes a small molecule or a protein, e.g., a cytokine. In some embodiments, the small molecule or protein is from about 0.5% to about 30% by weight of the nanoconstruct. In some embodiments, the small molecule is a chemotherapeutic agent, small molecule inhibitor, or a polypeptide. In some embodiments, the small molecule is a label. In some embodiments, the label is a lanthanide, a fluorescent dye, a gold nanoparticle, a quantum dot, a positron emission tomography (PET) tracer, or a magnetic resonance imaging (MRI) contrast agent.

The nanoconstruct may also include a targeting agent, such as an antibody, a scFv antibody, an affibody, an aptamer, a peptide, or small targeting molecule. In some embodiments, the targeting agent is from about 0.1% to about 10% by weight of the nanoconstruct, e.g., from about 0.3% to about 5% by weight of the nanoconstruct. In some embodiments, the small targeting molecule is a carbohydrate or ligand.

In some embodiments, the nanoconstruct is lyophilized, for instance, with a sugar, such as trehalose, or other lyoprotectant. The sugar, e.g., trehalose, or other lyoprotectant may be from about 1% to about 10% by weight of the nanoconstruct.

The invention also provides a pharmaceutical composition including an effective amount of a nanoconstruct of the invention and a pharmaceutically acceptable carrier.

In another aspect, the invention features a method of delivering an agent to a site in a human or other mammalian subject. The method may include administering an effective amount of a nanoconstruct of the invention containing the agent to the human or other mammalian subject. The administration is performed under conditions to deliver the nanoconstruct to the site, such as a cell or tumor. In some embodiments, the nanoconstruct is administered under conditions that the nanoconstruct is internalized by the cell. The nanoconstruct may be administered subcutaneously, topically, systemically, intravesically, orally, intratumorally, or intraperitoneally.

The subject is, for example, suffering from a disease or condition characterized by over-expression of one or more genes relative to expression of the one or more genes in a healthy subject. In some embodiments, the disease or condition is AMD, macular edema, chronic optic nerve atrophy, pachyonychia congenital, chronic lymphocytic leukemia, metastatic lymphoma, metastatic cancer, solid tumors, acute kidney injury, delayed graft function, familia adenomatous polyposis, hypercholesterolemia, liver fibrosis, cystic fibrosis, dermal scarring, Ebola infection, RSV infection, or inflammation. In some embodiments, the nanoconstruct is administered in an amount sufficient to treat the subject having the disease or condition.

In some embodiments, the agent is a label, such as a lanthanide, a gold nanoparticle, a quantum dot, a fluorescent dye, a PET tracer, or a MRI contrast agent.

In some embodiments, the agent is a therapeutic agent, such as a nucleic acid capable of modulating expression of a target protein. The nucleic acid may be a siRNA, miRNA, miRNA mimic, or antisense oligomer. In some embodiments, expression of the target gene is reduced. In some embodiments, the therapeutic agent is a chemotherapeutic agent, a small molecule inhibitor, an antibody, a peptide, and/or a cytokine.

In some embodiments, the subject is diagnosed with cancer. In some embodiments, the effective amount is a therapeutically effective amount. In some embodiments, the cancer is resistant to a monoclonal antibody or a small molecule inhibitor. The therapeutic agent may be an oligonucleotide that targets expression of a protein inhibited by the monoclonal antibody or the small molecule inhibitor.

In some embodiments, the subject is diagnosed with or is at risk for fibrosis or inflammation. In some embodiments, the nanoconstruct reduces reactive oxygen species, bioavailable copper, and/or NOX expression level in the subject. In some embodiments, the agent is administered in an amount sufficient to reduce tumor migration or inflammation in the human or other mammalian subject. In some embodiments, the nanoconstruct modulates an adverse effect of one or more cytokines.

In another aspect, the invention features a method of making a nanoconstruct including providing a nanoparticle coated with a cationic polymer and cross-linking the cationic polymer to make the nanoconstruct. The nanoparticle may be a silica nanoparticle, a silicon nanoparticle, an iron oxide nanoparticle, a gold nanoparticle, a silver nanoparticle, or a carbon nanotube, e.g., a mesoporous silica nanoparticle or an iron oxide nanoparticle. In some embodiments, the cationic polymer is cross-linked in the presence of free cationic polymer. In some embodiments, the cationic polymer is polyethylenimine, chitosan, polypropyleneimine, polylysine, polyamidoamine, poly(allylamine), poly(diallyldimethylammonium chloride), poly(N-isopropyl acrylamide-co-acrylamide), poly(N-isopropyl acrylamide-co-acrylic acid), diethylaminoethyl-dextran, poly-(N-ethyl-vinylpyridinium bromide), poly(dimethylamino)ethyl methacrylate, and/or poly(ethylene glycol)-co-poly(trimethylaminoethyl-methacrylate chloride). The polyethylenimine may have a molecular weight of from about 0.8 kDa to about 10 kDa.

The cationic polymer may be cross-linked using dithiobis [succinimidyl propionate] (DSP), 3, 3'-dithiobis(sulfosuccinimidyl propionate (DTSSP), or dimethyl 3, 3'-dithiobis-propionimidate (DTBP). For instance, in some embodiments, the cationic polymer is cross-linked using DSP.

In some embodiments, the method includes attaching a stabilizer to the nanoconstruct. The stabilizer may be selected from the group consisting of polyethylene glycol, dextran, polysialic acid, HA, PVP, PVA, and PAM. In some embodiments, the polyethylene glycol has a molecular weight of from about 1 kDa to about 20 kDa. In some embodiments, the method includes incubating maleimide-polyethylene glycol-N-hydroxysuccinimidyl ester (Mal-PEG-NHS) with the nanoconstruct at a weight ratio of from about 0.5:1 to about 5:1.

In some embodiments, the method further includes attaching a targeting agent to the nanoconstruct, e.g., to the nanoparticles, cationic polymer, or stabilizer. The method may include admixing the nanoconstruct with at least one type of oligonucleotide, e.g., a siRNA, miRNA, miRNA mimic, or antisense oligomer, that binds noncovalently to the cationic polymer.

In some embodiments, the method includes admixing a small molecule or protein with the nanoparticle or the nanoconstruct so that the small molecule or protein binds to the nanoconstruct, e.g., to the nanoparticles, cationic polymer, or stabilizer. The small molecule or protein may be a chemotherapeutic agent, a label, a peptide, and/or a cytokine.

In some embodiments, the method includes lyophilizing the nanoconstruct, e.g., with a sugar, e.g., trehalose, or other lyoprotectant.

In another aspect, the invention features a method of labeling a target by contacting a nanoconstruct of the invention with the target under conditions to bind the nanoconstruct to the target. In some embodiments, the target is a cell or protein. The nanoconstruct may be internalized by the cell. In some embodiments, the nanoconstruct binds to the exterior of the cell. The nanoparticle of the nanoconstruct is, for example, a silica nanoparticle, a silicon nanoparticle, an iron oxide nanoparticle, a gold nanoparticle, a silver nanoparticle, or a carbon nanotube, e.g., a mesoporous silica nanoparticle or an iron oxide nanoparticle.

In some embodiments, the label is a lanthanide, a fluorescent dye, a gold nanoparticle, a quantum dot, a PET tracer, or a MRI contrast agent. The method may include quantifying the amount of target by detecting the label after the nanoconstruct binds to the target.

In some embodiments, the method includes administering the labeled target to a subject and detecting the location of the target after the labeled target is administered. In some embodiments, the nanoconstruct further includes a therapeutic agent. In some embodiments, the detecting is by fluorescence, magnetic resonance, or PET.

In another aspect, the invention features a multilayer nanoconstruct that contains a mesoporous silica nanoparticle between about 10 nm to about 90 nm in diameter and a cationic polymer electrostatically bound to an exterior surface of the mesoporous silica nanoparticle. The cationic polymer is cross-linked. The nanoconstruct additionally contains a stabilizer covalently attached to an amine of the cationic polymer, as well as a targeting agent covalently attached to the stabilizer. The stabilizer may prevent aggregation of the nanoconstruct in solution.

In some embodiments, the cationic polymer is cross-linked with a cleavable bond. In some embodiments, the mesoporous silica nanoparticle is about 30 nm to about 60 nm in diameter. In some embodiments, the mesoporous silica nanoparticle is an antioxidant. In some embodiments, the hydrodynamic size of the nanoconstruct is about 80 nm to about 200 nm, e.g., from about 90 nm to about 120 nm.

The nanoconstruct may include at least one type of oligonucleotide electrostatically bound to the cationic polymer. In some embodiments, the at least one type of oligonucleotide is a siRNA, miRNA, miRNA mimic, or antisense oligomer. In some embodiments, the mass ratio of the mesoporous silica nanoparticle to the at least one type of oligonucleotide is about 10:1 to about 100:1. The at least one type of oligonucleotide may be a siRNA that silences expression of PLK1, AKT1/BCL2, HER2, EPS8L1, and HSP47. For instance, the at least one type of oligonucleotide may be miR-342-5p.

In some embodiments, the at least one type of oligonucleotide includes two or more different siRNAs loaded onto the nanoconstruct, such as two or more different siRNAs loaded onto the nanoconstruct that target different tumor genes. In some embodiments, the two or more different siRNAs loaded onto the nanoconstruct are selected from siPLK1, siAKT1/BCL2, siHER2, siEPS8L1, or siHSP47.

In some embodiments, the stabilizer protects the at least one type of oligonucleotide from serum enzymatic degradation for at least 24 hours.

The mesoporous silica nanoparticle may be porous. For instance, the pores may be from about 1 nm to about 6 nm in diameter. In some embodiments, the pore has a first opening at a first location on an exterior surface of the mesoporous silica nanoparticle and a second different opening at a second location on the exterior surface of the mesoporous silica nanoparticle.

In some embodiments, the nanoconstruct includes at least one label, such as a lanthanide or fluorescent dye. In some embodiments, the label is attached to both an inner surface of the pore and the exterior surface of the mesoporous silica nanoparticle. In some embodiments, the label is bound to the cationic polymer.

The nanoconstruct may include a small molecule. In some embodiments, the small molecule is attached on an inside of a pore. The small molecule may be attached to the exterior surface of the mesoporous silica nanoparticle. In some embodiments, the small molecule is attached to the cationic polymer. In some embodiments, the small molecule is about 0.5% to about 30% by weight of the mesoporous silica nanoparticle. In some embodiments, the small molecule is a chemotherapeutic agent, such as doxorubicin, paclitaxel, docetaxel, cisplatin, carboplatin, rapamycin, or camptothecin.

In some embodiments, the cationic polymer is about 5% to about 40% by weight of the mesoporous silica nanoparticle. The cationic polymer may be polyethylenimine, such as branched polyethylenimine. In some embodiments, the polyethylenimine is about 0.8 kDa to about 10 kDa. In some embodiments, the polyethylenimine is about 5% to about 40% by weight of the mesoporous silica nanoparticle.

In some embodiments, the stabilizer is between about 5 to about 40% by weight of the mesoporous silica nanoparticle. The stabilizer may be polyethylene glycol, such as polyethylene glycol that is from about 1 kDa to about 20 kDa. In some embodiments, the polyethylene glycol is about 5% to about 40% by weight of the mesoporous silica nanoparticle.

In some embodiments, the nanoconstruct does not trigger cytokine release from peripheral blood mononuclear cells.

In some embodiments, the targeting agent is about 0.5% to about 10% by weight of the mesoporous silica nanoparticle. The targeting agent may be a monoclonal antibody, a scFv antibody, an aptamer, a peptide, or small targeting molecule agent. For instance, the monoclonal antibody may be an anti-HER2 antibody, anti-EGFR antibody, anti-CD20 antibody, anti-VEGF-A antibody, anti-CD33 antibody, anti-CD52 antibody, or anti-TNFα antibody. In some embodiments, the targeting agent is a therapeutic agent, such as an anti-HER2 antibody.

In some embodiments, the nanoconstruct is lyophilized, e.g., with trehalose. In some embodiments, the trehalose is from about 5% to about 10% by weight of the mesoporous silica nanoparticle.

In another aspect, the invention features a method of making a nanoconstruct. The method may include combining a first surfactant with a second different surfactant to form a first mixture and adding a silica precursor to the first mixture to form a second mixture. This can result in the synthesis of a mesoporous nanoparticle. The method may include removing the first and second surfactants from the mesoporous silica nanoparticle and coating an exterior surface of the mesoporous silica nanoparticle with a cationic polymer to form a mesoporous silica nanoparticle-cationic polymer. The method may include cross-linking the cationic polymer in the presence of free cationic polymer, conjugating a stabilizer to an amine of the cationic polymer to form a mesoporous silica nanoparticle-cationic polymer-stabilizer, and conjugating a targeting agent to a maleimide group of the stabilizer to form the nanoconstruct.

In some embodiments, the first surfactant is cetyltrimethylammonium chloride. In some embodiments, the second different surfactant is triethanolamine.

The first mixture may be heated prior to adding the silica precursor. In some embodiments, the second mixture is heated prior to recovering the mesoporous silica nanoparticles.

In some embodiments, the method includes adding organosilanes to the second mixture after the solution is heated.

In some embodiments, coating the cationic polymer on the exterior surface of the mesoporous silica nanoparticle includes mixing the cationic polymer with the mesoporous silica nanoparticle in the presence of a solvent to form a third mixture. In some embodiments, the mass ratio of the cationic polymer to the mesoporous silica nanoparticle is about 1:1 to about 1:4. In some embodiments, the cationic polymer is polyethylenimine. In some embodiments, the polyethylenimine is about 0.8 kDa to about 10 kDa. In some embodiments, the cationic polymer is cross-linked using DSP (Dithiobis[succinimidyl propionate], DTSSP (3, 3'-dithiobis (sulfosuccinimidyl propionate), or DTBP (dimethyl 3, 3'-dithiobispropionimidate). In some embodiments, the cationic polymer is cross-linked using dithiobis succinimidyl propionate.

In some embodiments, the stabilizer is added to the mesoporous silica nanoparticle-cationic polymer in the presence of a PBS buffer in an amount from about 5:1 to about 1:1 of the mesoporous silica nanoparticle. In some embodiments, the stabilizer is polyethylene glycol. In some embodiments, the polyethylene glycol is about 1 kDa to about 20 kDa. In some embodiments, the polyethylene glycol is about 5 kDa.

In some embodiments, the targeting agent is a monoclonal antibody, a scFv antibody, an aptamer, a peptide, or a small molecule targeting agent.

In some embodiments, the method includes admixing a mesoporous silica nanoparticle-cationic polymer-stabilizer-targeting agent construct with at least one type of oligonucleotide.

In some embodiments, the at least one type of oligonucleotide electrostatically binds to the nanoconstruct.

In some embodiments, the at least one type of oligonucleotide is siRNA, miRNA, miRNA mimics, DNA, or an antisense oligomer. In some embodiments, the at least one type of oligonucleotide is siPLK1, siAKT1/BCL2, siHER2, siEPS8L1, or siHSP47. In some embodiments, the at least one type of oligonucleotide is miR-342-5p. In some embodiments, the oligonucleotide is admixed with the mesoporous silica nanoparticle-cationic polymer-stabilizer-targeting agent construct at a mass ratio of nanoparticle per oligonucleotide of about 10:1 to about 100:1. In some embodiments, the at least one type of oligonucleotide is siRNA. In some embodiments, the siRNA is against HER2 (siHER2). In some embodiments, the siRNA is admixed with the mesoporous silica nanoparticle-cationic polymer-stabilizer-targeting agent construct at a mass ratio of nanoparticle per oligonucleotide of about 25:1 to about 50:1.

In some embodiments, the method includes combining the first mixture with a small molecule prior to coating the mesoporous silica nanoparticle with the cationic polymer. In other embodiments, the method includes combining the first mixture with a small molecule after coating the mesoporous silica nanoparticle with the cationic polymer. In some embodiments, the small molecule is a chemotherapeutic agent. In some embodiments, the chemotherapeutic agent is doxorubicin, paclitaxel, docetaxel, cisplatin, carboplatin, rapamycin, or camptothecin.

In some embodiments, the method includes admixing at least one label. In some embodiments, the label is added to the first mixture. In some embodiments, the label is added to the mesoporous silica nanoparticle. In some embodiments, the label is added to the mesoporous silica nanoparticle-cationic polymer. In some embodiments, the label is added to the mesoporous silica nanoparticle-cationic polymer-stabilizer. In some embodiments, the label is a lanthanide. In other embodiments, the label is a fluorescent dye. In some embodiments, the fluorescent dye is conjugated to both an inner surface of the pore and the exterior surface of the mesoporous silica nanoparticle using an amine-NHS ester reaction.

In some embodiments, the method includes lyophilizing the nanoconstruct, e.g., with trehalose. The amount of the trehalose may be 1-10% by weight of the mesoporous silica nanoparticle.

In another aspect, the invention features a method of treating cancer in a human or other mammalian subject by administering an effective amount of a nanoconstruct that contains a mesoporous silica nanoparticle between about 30 nm to about 90 nm in diameter and a cross-linked cationic polymer electrostatically bound to an exterior surface of the mesoporous silica nanoparticle. The nanoconstruct may contain a stabilizer covalently attached to an amine of the cationic polymer, a targeting agent covalently attached to the stabilizer, and at least one type of oligonucleotide electrostatically bound to the cationic polymer on the exterior surface of the mesoporous silica nanoparticle. The at least one type of oligonucleotide may be protected by the stabilizer, e.g., from enzymatic degradation.

In some embodiments, the cancer is resistant to a monoclonal antibody, and the at least one type of oligonucleotide may target the same gene as the monoclonal antibody. In some embodiments, the cancer is resistant to a small molecule inhibitor, and the at least one type of oligonucleotide may target the same gene as the small molecule inhibitor. In some embodiments, the cancer is HER2+, and may be resistant to trastuzumab and/or lapatinib. In some embodiments, one dose of the nanoconstruct reduces the HER2 protein levels by at least 40%. In some embodiments, the at least one type of oligonucleotide can target two or more genes. In some embodiments, the at least one type of oligonucleotide is a siRNA duplex against both AKT1 and BCL2.

In some embodiments, the mesoporous silica nanoparticle is an antioxidant. The mesoporous silica nanoparticle may be therapeutic. In some embodiments, the at least one type of oligonucleotide is a siRNA, miRNA, miRNA mimic, or antisense oligomer. For instance, delivery of the siRNA on the nanoconstruct may increase the rate of cancer cell death by at least 15% over delivery of the siRNA with a transfection reagent.

In some embodiments, the nanoconstruct includes a chemotherapeutic agent. In some embodiments, the addition of the chemotherapeutic agent does not negatively impact the gene silencing efficacy of the at least one type of oligonucleotide. In some embodiments, co-delivery of the siRNA and the chemotherapeutic agent improves cancer cell death caused by chemotherapeutic agents by at least 10%.

In another aspect, the invention features a method of diagnosing cancer in a mammalian subject. The method includes administering a nanoconstruct that contains a porous mesoporous silica nanoparticle between about 10 nm to about 80 nm in diameter and a cross-linked cationic polymer electrostatically bound to an exterior surface of the mesoporous silica nanoparticle. The nanoconstruct may contain a stabilizer covalently attached to an amine of the cationic polymer, a targeting agent covalently attached to the stabilizer, and a label attached to the nanoconstruct. The use of the label allows imaging of tumors and quantification of tumor proteins targeted by the targeting agent.

In some embodiments, the exterior surface of the mesoporous silica nanoparticle includes thiol, amine, or phosphonate functional groups. The label, e.g., a fluorescent dye or a lanthanide, may be attached to functional groups on the surface of the mesoporous silica nanoparticle.

In some embodiments, the nanoconstruct enables tumor detection by MRI. In some embodiments, the label is gadolinium. The label may be attached on both an inner surface of the pore in the mesoporous silica nanoparticle and on the exterior surface of the mesoporous silica nanoparticle. In some embodiments, the label is attached to the cationic polymer electrostatically bound to the exterior surface of the mesoporous silica nanoparticle. In some embodiments, the targeting agent is a monoclonal antibody, a scFv antibody, an aptamer, a peptide, or a small targeting molecule agent. In some embodiments, the targeting agent is a monoclonal antibody. In some embodiments, the targeting agent is an anti-HER2 antibody, anti-EGFR antibody, anti-CD20 antibody, anti-VEGF-A antibody, anti-CD33 antibody, anti-CD52 antibody, or anti-TNFα antibody.

In another aspect, the invention features a method of characterizing targeted protein in a tissue specimen. The method includes staining the targeted protein with a nanoconstruct containing a mesoporous silica nanoparticle between about 10 nm to about 80 nm in diameter and a cross-linked a cationic polymer electrostatically bound to an exterior surface of the mesoporous silica nanoparticle. The nanoconstruct may contain a stabilizer covalently attached to an amine of the cationic polymer, a targeting agent covalently attached to the stabilizer, and a label attached to the mesoporous silica nanoparticle. The label allows an amount of the targeted protein to be quantified, e.g., by imaging.

In some embodiments, the exterior surface of the mesoporous silica nanoparticle includes thiol, amine, or phosphonate functional groups. The label may be attached to the functional groups on the exterior surface of the mesoporous silica nanoparticle. In some embodiments, the label is attached to the cationic polymer on the exterior surface of the mesoporous silica nanoparticle. In some embodiments, the label is lanthanide, such as gadolinium, or a fluorescent dye. The targeted protein may be quantified by mass spectrometry.

In another aspect, the invention features a method of treating cancer, inflammation, and fibrosis in a human or other mammalian subject. The method includes administering an effective amount of a nanoconstruct containing a porous mesoporous silica nanoparticle between about 30 nm to about 90 nm in diameter and a cross-linked cationic polymer electrostatically bound to an exterior surface of the mesoporous silica nanoparticle. The nanoconstruct contains a stabilizer covalently attached to an amine of the cationic polymer and at least one type of oligonucleotide electrostatically bound to the cationic polymer on the exterior surface of the mesoporous silica nanoparticle via electrostatic interaction. The at least one type of oligonucleotide may be protected by the stabilizer, e.g., from enzymatic degradation.

The nanoconstruct may be an antioxidant. In some embodiments, the nanoconstruct reduces reactive oxygen species and NOX4 expression level. The nanoconstruct may modulate the adverse effect of cytokines. In some embodiments, use of the nanoconstruct decreases a fibrotic marker. In some embodiments, the fibrotic marker is COL I or alpha-SMA. The at least one type of oligonucleotide may be a siRNA, miRNA, miRNA mimic, or an antisense oligomer, such as a siRNA against HSP47 (siHSP47).

In some embodiments, the mesoporous silica nanoparticle carrier is therapeutic. The nanoconstruct may include a small molecule inhibitor selected from dasatinib, imatinib, and nilotinib.

In some embodiments, the small molecule inhibitor is attached to both an inner surface of the pore in the mesoporous silica nanoparticle and the exterior surface of the mesoporous silica nanoparticle. The small molecule inhibitor may be attached to the cationic polymer. In some embodiments, the nanoconstruct delivers the small molecule inhibitor to target cells. In some embodiments, the nanoconstruct is administered subcutaneously. In some embodiments, the nanoconstruct is administered topically.

For any of the above aspects, the nanoconstruct may include a stabilizer, e.g., PEG, and a targeting agent, e.g., an antibody. In these embodiments, the nanoparticles is, for example, mesoporous silica or iron oxide, and cationic polymer is, for example, PEI. Such nanoconstructs may further include an oligonucleotide, a small molecule, and/or a label.

BRIEF DESCRIPTION OF THE DRAWINGS

FIGS. 8A-8I show the cellular uptake of siSCR-NP by various cell lines. FIG. 8A is a chart illustrating the % cellular uptake of trastuzumab(T)-siSCR-NP by BT474 breast cancer cells (HER2+). FIG. 8B is a chart illustrating the % cellular uptake of trastuzumab(T)-siSCR-NP by SKBR3 breast cancer cells (HER2+). FIG. 8C is a chart illustrating the % cellular uptake of trastuzumab(T)-siSCR-NP by MCF7 (HER2−) breast cancer cells. A negative control antibody, rituximab (R), demonstrated specificity for the trastuzumab-conjugated nanoconstruct counterpart. FIG. 8D shows a western blot confirming the HER2 content of these 3 cell lines. FIG. 8E shows the extent of cellular internalization of dye-tagged siSCR nanoconstructs by BT474 cells. FIG. 8F shows the extent of cellular internalization of dye-tagged siSCR nanoconstructs by SKBR3 cells. FIG. 8G shows the extent of cellular internalization of dye-tagged siSCR nanoconstructs by MCF7 cells. FIGS. 8H-8I shows that when changing from trastuzumab to a different antibody (e.g. anti-EGFR-antibody or cetuximab or "C"), the material (C-siSCR-N$^{10C}$) could target (H) cells with high EGFR expression. FIG. 8I shows higher cellular uptake of C-siSCR-NP$^{10C}$ nanoconstructs by EGFR+ cells as compared to cells with no EGFR expression.

FIG. 9A is a graph depicting HER2 knockdown by siHER2-nanoconstructs (T-Np$^{10C}$) as reduced HER2 protein expression per cell of three HER2$^+$ cells at 72 hours post-treatment with siHER2 vs. siSCR (60 nM) on T-NP$^{10C}$. FIG. 9B is a graph showing reduced HER2 expression at the mRNA level (48 hours post-treatment with siHER2 vs. siSCR), FIG. 9C is a graph showing the functional outcome of increased apoptotic activity (4 days post-treatment with siHER2 vs. siSCR). FIG. 9D is a graph showing reduced cell viability of BT474 cells (4 days post-treatment with siHER2 vs. siSCR).

FIG. 12A is a graph showing HER2 protein reduction in three HER2$^+$ cell lines upon treatment with 60 nM siHER2 vs. siSCR on nanoconstructs with cross-linked 1.8-kDa PEI. FIG. 12B is a graph showing HER2 protein reduction in three HER2$^+$ cell lines upon treatment with 120 nM siHER2 vs. siSCR on nanoconstructs with cross-linked 1.8-kDa PEI. FIG. 12C is a graph showing HER2 protein reduction in three HER2+ cell lines upon treatment with 60 nM siHER2 vs. siSCR on the commercial transfection agent, DharmaFECT™. The same treatment condition was utilized as that used in FIG. 9A.

FIG. 13A is a graph showing BT474-R to be resistant to trastuzumab, compared to parental BT474. FIG. 13B is a graph showing the ability of T-siHER2-NP$^{10C}$ to achieve the same response in BT474-R and BT474 with respect to siHER2 action, while FIG. 13C is a graph showing that trastuzumab on a nanoconstruct without siHER2 (T-siSCR-NP$^{10C}$) elicits less of a response in the resistant BT474-R cells. 60 nM siRNA was used, and cell viability was measured 5 days post-treatment with media replenished overnight after treatment.

FIGS. 14A-14O show the blood compatibility of siHER2-nanoconstructs. FIG. 14A shows excellent blood compatibility of siHER2-nanoconstructs (T-siHER2-NP$^{1.8C}$ and T-siHER2-NP$^{10C}$) with no significant increase in hemolysis over vehicle controls (saline and PBS) or an FDA-approved nanoparticle-drug benchmark (Abraxane).

FIGS. 15A-15F show cytokine induction in peripheral blood mononuclear cells following nanoconstruct treatment and endotoxin test of the nanoconstruct. FIG. 15A is a chart showing IFN-α induction in peripheral blood mononuclear cells following 24-hour exposure with T-siHER2-NP$^{1.8C}$, T-NP$^{10C}$, T-siHER2-NP$^{10C}$, Abraxane, or Feraheme. FIG. 15B is a chart showing IL-1β induction in peripheral blood mononuclear cells following 24-hour exposure with T-siHER2-NP$^{1.8C}$, T-NP$^{10C}$, T-siHER2-NP$^{10C}$, Abraxane, or Feraheme. FIG. 15C is a chart showing IL-6 induction in peripheral blood mononuclear cells following 24-hour exposure with T-siHER2-NP$^{1.8C}$, T-NP$^{10C}$, T-siHER2-NP$^{10C}$, Abraxane, or Feraheme. FIG. 15D is a chart showing TNF-α induction in peripheral blood mononuclear cells following 24-hour exposure with T-siHER2-NP$^{1.8C}$, T-NP$^{10C}$, T-siHER2-NP$^{10C}$, Abraxane, or Feraheme. FIG. 15E is an image recorded from the LAL gel-clot assay on the nanoconstructs (T-siHER2-NP$^{10C}$) at 5× concentration. FIG. 15F is an image recorded from the LAL gel-clot assay on Abraxane at 5× concentration. Both are negative for endotoxin according to the manufacturer's protocol.

FIG. 17A is a graph showing tumor growth in mice bearing orthotopic HCC1954 tumor xenografts receiving multiple doses (i.v., time points indicated by arrows) of T-NP$^{10C}$ loaded with siHER2 or siSCR (1.25 mg/kg siRNA, NP/siRNA of 50) or PBS control (n=5/group). FIG. 17B is a graph showing tumor growth in mice bearing orthotopic HCC1954 tumor xenografts receiving multiple doses of trastuzumab (10 mg/kg, i.p.) or saline (n=7/group) at time points indicated by arrows. FIG. 17C is a graph showing tumor growth in mice bearing orthotopic HCC1954 tumor xenografts receiving multiple doses of trastuzumab (5 mg/kg, i.v.) or saline (n=5/group) at time points indicated by arrows. FIG. 17D is a graph showing tumor growth in mice bearing orthotopic HCC1954 tumor xenografts receiving multiple doses of trastuzumab (5 mg/kg, i.v.) plus paclitaxel (3.1 mg/kg, i.v.) or saline (n=9/group) at time points indicated by arrows.

FIG. 20A is a graph showing BT474-TRgf to be resistant to trastuzumab in vitro compared to parental BT474. FIG. 20B is a graph showing tumor growth in mice bearing BT474-TRgf xenografts (n=5-7/group) post i.v. injection with saline, trastuzumab (2.5 mg/kg, twice weekly) or trastuzumab-conjugated nanoconstruct (T-NP) loaded with siHER2 or siSCR at the time points indicated by arrows. Black indicates 1.25 mg siRNA/kg, and gray indicates 2.5 mg siRNA/kg.

FIGS. 21A-21E show the purity and specificity of HER2 scFV, and size distribution, and luciferase silencing efficacy of nanoconstructs containing HER2 scFV, trastuzumab (T), or folic acid (FA). FIG. 21A shows a gel indicating comparable purity of three batches of HER2 scFv. FIG. 21B is a diagram confirming the presence of the HER2 scFv using Anti-6xHisTag antibody. FIG. 21C shows specificity of HER2 scFv for HER2+ cells (BT474, SKBR3, and JIMT1) over HER2− cells (MCF7 and MDAMB468). FIG. 21D shows the hydrodynamic sizes of HER2 scFV conjugated NP (scFV-NP), folic acid conjugated NP (FA-NP), and trastuzumab-conjugated NP (T-NP), all loaded with same content of siHER2. FIG. 21E shows the luciferase silencing efficacy of nanoconstructs having three different targeting agents as in FIG. 21D. For HER2 scFV loading, 1 and 4% by weight of MSNP was used during synthesis. For FA, 25% by weight as Mal-PEG(5 kDa)-FA was used during synthesis.

FIG. 22A is a chart showing the hydrodynamic diameter of lyophilized nanoconstructs (NP or T-NP) with varied amounts of trehalose (TL) compared to freshly made nanoconstructs (Fresh) from the same batch. FIG. 22B is a chart showing the zeta potential of lyophilized nanoconstructs (NP or T-NP) with varied amounts of trehalose (TL) compared to freshly made nanoconstructs (Fresh) from the same batch. FIG. 22C is a chart showing the silencing efficacy of lyophilized nanoconstructs (NP or T-NP) with varied amounts of trehalose (TL) compared to freshly made nanoconstructs (Fresh) from the same batch. FIG. 22D is a chart showing the cancer cell-killing efficacy of lyophilized nanoconstructs (NP or T-NP) with varied amounts of trehalose (TL) compared to freshly made nanoconstructs (Fresh) from the same batch. Data indicate 5% TL (by weight of nanoconstruct) as the best condition for preserving all properties of the fresh material. (A-B) no siRNA, (C) with 30 nM siLUC vs. siSCR, (D) with 60 nM siHER2 vs. siSCR.

FIG. 23A is a chart showing the relative hydrodynamic diameter of lyophilized T-NP with 5% trehalose (TL) and stored at various temperatures. FIG. 23B is a chart showing the relative zeta potential of lyophilized T-NP with 5% trehalose (TL) and stored at various temperatures. FIG. 23C is a chart showing relative siRNA loading of lyophilized T-NP with 5% trehalose (TL) and stored at various temperatures. FIG. 23D is a chart showing relative silencing efficacy of lyophilized T-NP with 5% trehalose (TL) and stored at various temperatures. FIG. 23E is a chart showing relative cancer cell-killing efficacy of lyophilized T-NP with 5% trehalose (TL) and stored at various temperatures. Data indicate −20° C. as the best storage temperature for preserving all properties of the fresh material for at least 24 weeks (6 months). (A-D): 30 nM siLUC and siLUC/NP of 50; (E): 60 nM siHER2 and siHER2/NP of 50.

FIGS. 31A-31B are a series of graphs showing nanoconstructs containing PEI and PEG (MSNP-PEI-PEG and loaded with non-targeting siSCR) could reduce intracellular ROS activity of primary dermal fibroblast with a potency similar to that of NAC (A), as well as the antioxidant properties (DPPH scavenging) of the material (measured in a cell free system) were attributed to the MSNP core rather than PEI or PEG (B). FIG. 31C is a graph showing that the nanoconstructs could reduce protein expressions of pro-fibrotic genes (HSP47, NOX4) and fibrotic markers (COL I and alpha-SMA) without harming cells in an in vitro fibrosis model (TGF-beta stimulated dermal fibroblast). FIG. 31D is a graph showing that the nanoconstructs could reduce mRNA levels of NOX4, COL I and alpha-SMA in a second in vitro fibrosis model (bleomycin treated fibroblast). Data from Morry et al. 2015.

FIGS. 32A-32G show the experimental design and results of assays conducted to probe the ability of nanoconstructs to treat skin fibrotic disease. FIG. 32A is a schematic showing the study design of a series of experiments aimed at determining the effectiveness of siHSP47-nanoconstruct (MSNP-PEI-PEG) for treating skin fibrotic disease in vivo (bleomycin stimulated skin fibrosis in mice). FIG. 32B is a series of representative images showing that the siHSP47-NP could reduce dermal thickening of mice caused by bleomycin treatment. FIG. 32C is a chart showing the ability of siHSP47-NP to reduce dermal thickening of mice caused by bleomycin treatment. FIG. 32D is a chart showing the ability of siHSP47-NP to reduce the expression of the fibrotic marker HSP47. FIG. 32E is a chart showing the ability of siHSP47-NP to reduce the expression of the fibrotic marker NOX4. FIG. 32F is a chart showing the ability of siHSP47-NP to reduce the expression of the fibrotic marker alpha-SMA. FIG. 32G is a chart showing the ability of siHSP47-NP to reduce the expression of the fibrotic marker COL I. Some (albeit less) reduction effects were observed with siSCR-NP due to the antioxidant properties of the MSNP core.

FIG. 33A is a graph showing that siPLK1-NP treatment of LM2-4luc+/H2N cells could reduce PLK1 expression at the mRNA level. FIG. 33B is a graph showing that siPLK1-NP treatment can reduce PLK1 protein expression at the protein level. FIG. 33C is a graph showing the ability of siPLK1-NP to increase G2/M cell cycle phase distribution with a potency similar to that of PLK1 inhibitor (BI2536). FIG. 33D is a graph showing the ability of siPLK1-NP to decrease cancer cell viability. siRNA dose of 50 nM and NP/siRNA of 50, BI2536 dose of 10 nM, treatment time: 24 hr for (A), 48 hr for (B), 24 hr for (C) and 5 days for (D).

FIGS. 34A-34H show the effect of nanoconstruct treatment on LM2-4luc+H2N cancer cells. FIG. 34A is a graph showing that the nanoconstruct treatment of LM2-4luc+/H2N cancer cells could reduce intracellular ROS level with a potency similar to that of 2 mM NAC and 5 µM DPI. FIG. 34B is a graph showing that nanoconstruct treatment of LM2-4luc+/H2N cancer cells does not cause cell death at the concentrations used. FIG. 34C is a graph showing the ability of nanoconstruct treatment of LM2-luc+/H2N cancer cells to reduce NOX4 mRNA expression with a potency similar to that of 20 mM NAC. FIG. 34D is a series of images showing that the nanoconstructs (loaded with siSCR, DY677-siSCR, or siPLK1) could reduce cancer cell migration in wound healing assays. FIG. 34E is a chart showing that nanoconstructs loaded with siSCR or siPLK1 could reduce cancer cell migration more effectively than siRNA delivered with DharmaFECT™. FIG. 34F is a series of images showing that the nanoconstructs (loaded with siSCR) could inhibit cancer cell invasion in FITC-gelatin degradation assays with a potency similar to that of 5 µM DPI. FIG. 34G is a chart showing that nanoconstructs loaded with siSCR could inhibit cancer cell invasion in FITC-gelatin degradation assays with a potency similar to that of 5 µM DPI. FIG. 34H is a chart showing that nanoconstructs loaded with siSCR could inhibit cancer cell invasion in Matrigel-coated Boyden chamber assays with a potency similar to the DPI but greater than that of 2-10 mM NAC. A siRNA dose of 50 nM and a NP/siRNA ratio of 50 by mass were used throughout.

FIGS. 35A-35H show the experimental design and results of assays conducted to determine the therapeutic effects of trastuzumab-conjugated nanoconstructs and loaded with siPLK1 (T-siPLK1-NP) in a metastatic cancer mouse model. FIG. 35A is a schematic showing the design of short and long term studies aimed at understanding whether T-siPLK1-NP can treat metastatic HER2+ breast cancer (LM2-4luc+/H2N) in vivo. FIG. 35B is a chart showing the results of the Short-term study (n=5/group). T-siPLK1-NP could reduce the incidence rate of cancer in various organs of mice and total tumor burden after 6 doses of treatment. Some reduction of the incidence rate was also observed with T-siSCR-NP. FIG. 35C is a chart showing that T-siPLK1-NP could also reduce in vivo imaging signals (IVIS) of the cancer in the thorax region (lung) of the mice. FIG. 35D is a graph showing that T-siPLK1-NP could reduce lung weight of mice bearing cancer to the level similar to that of normal mice (without cancer). FIG. 35E is a graph showing that T-siPLK1-NP could reduce PLK1 mRNA expression levels of the human cancer presiding in the lungs of mice. Long-term study (n=8/group): FIG. 35F is a chart showing that T-siPLK1-NP could reduce IVIS signals of the cancer in the thorax region (lung) of the mice. FIG. 35G is a chart showing the extended survival of mice from the same study due to T-siPLK1-NP treatment. FIG. 35H is a series of images showing the ability of T-siPLK1-NP to reduce cancer lesions in the lung tissues as shown by representative H&E images and anti-human vimentin staining. Treatments as specified; vertical lines in (C) and (F) represent dosing days.

FIG. 38A shows the hydrodynamic size distribution of nanoconstructs containing an iron oxide nanoparticle core (ION, Feraheme) modified with 10-kDa PEI, prepared using 4:1 by mass of ION:PEI (called F1) or 3:1 of ION:PEI (called F2), 5-kDa PEG, and conjugated with trastuzumab (T-F2). FIG. 38B is a graph showing the luciferase silencing efficacy of the three materials with a siRNA dose of 50 nM and NP/siRNA of 10. FIG. 38C is a chart showing the enhanced T2 relaxivity of the F2 and T-F2 over Feraheme, measured by T2 MRI (small animal Bruker BioSpin 11.75 T MRI instrument) indicating that the materials can be used as MRI contrast agents.

REFERENCE TO SEQUENCE LISTING

Figure 1A:
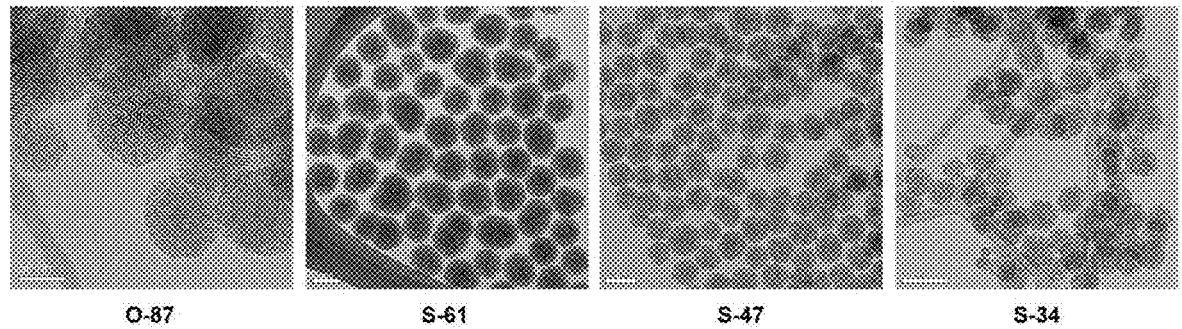
FIGS. 1A-1C show (A) TEM images of mesoporous silica nanoparticle (MSNP) cores of various sizes (B) schematic of the surface modification of the MSNP, and (C) the hydrodynamic size distribution of the nanoconstructs made from MSNP cores shown in (A) and surface modified as illustrated in (B). Unless specified otherwise, MSNP was a S-47 core, polyethylenimine (PEI) was 10 kDa and cross-linked, PEG was 5 kDa, and antibody was trastuzumab (T) throughout this application.

The nucleic acid sequences described herein are shown using standard letter abbreviations, as defined in 37 C.F.R. § 1.822. Only one strand of each nucleic acid sequence is shown, but the complementary strand is understood as included in embodiments where it would be appropriate. A computer readable text file, entitled "2JE1181.txt (Sequence Listing.txt)" created on or about Aug. 10, 2021, with a file size of 4 KB, contains the sequence listing for this application and is hereby incorporated by reference in its entirety.

DETAILED DESCRIPTION

Described herein are nanoconstructs for the treatment or diagnosis of disease including cancer, inflammation and fibrosis. The nanoconstruct contains a nanoparticle, such as a mesoporous silica nanoparticles (MSNP), a gold nanoparticle, a silver nanoparticle, an iron oxide nanoparticle, or a carbon nanotube, optionally loaded with a variety of additional agents including, but not limited to, cationic polymers, stabilizers, targeting agents, small molecules or proteins, labels, and/or oligonucleotides. Combinations of various additional agents are also contemplated. For example, the nanoconstruct includes a cationic polymer, stabilizer, targeting agent, and small molecule, label, and/or oligonucleotide. Nanoconstructs may also include more than one type of cationic polymer, stabilizer, targeting agent, small molecule, protein, label, and/or oligonucleotide. For example, nanoconstructs may include multiple, different oligonucleotides and/or small molecules or proteins that act on the same or different targets. The use of such additional agents may provide an additive or synergistic effect for disease treatment when delivered together on a nanoconstruct.

Nanoparticles

Nanoparticles useful with the compositions and methods of the invention include, without limitation, mesoporous silica nanoparticles (e.g., MSNPs), iron oxide nanoparticles, silver nanoparticles, gold nanoparticles, and carbon nanotubes. Nanoparticles may or may not be porous. Exemplary sizes for the nanoparticle cores are from about 5 nm to about 200 nm, about 5 to about 20 nm, about 30 nm to about 100 nm, about 30 nm to about 80 nm, about 30 nm to about 60 nm, about 40 nm to about 80 nm, about 70 nm to about 90 nm, or about 5 nm, about 10 nm, about 20 nm, about 30 nm, about 40 nm, about 50 nm, about 60 nm, about 70 nm, about 80 nm, about 90 nm, or about 100 nm. Generally, the nanoparticle cores are spherical, although other shapes, such as rods and discs, may also be used.

Additional components may be attached to nanoparticles by various mechanisms, covalently or noncovalently. For example, cationic polymers may be attached to nanoparticles by charge, e.g., for silica or iron oxide nanoparticles. Alternatively, the surfaces of the nanoparticles may be altered to include reactive moieties for conjugation to cationic polymers and/or other components, or the cationic polymers or other components may include a moiety that binds to the nanoparticles. For example, nanoparticle cores such as silica, silicon, gold, iron oxide, and silver nanoparticles, as well as carbon nanotubes, may be modified with reactive moieties such as thiols, phosphonate, carboxylate, and amines prior to attachment with cationic polymers and other components. Cationic polymers and other components may be modified to include these or other moieties, including but not limited to, maleimide, N-hydroxy succinimidyl (NHS) esters, or azides, prior to binding to the nanoparticle cores. Components may be attached directly to nanoparticles, either on the surface or within pores if present.

Cationic Polymers

In some embodiments, nanoparticles, such as MSNPs, are coated with cationic polymers or other compounds. The cationic polymer may bind to the surface of the nanoparticle using any appropriate means. In some embodiments, the cationic polymer binds to the nanoparticle via electrostatic interaction. The cationic polymer may be any polymer with a positive charge, such as, but not limited to, polyethylenimine (PEI) (see, e.g., Example III), polyamidoamine, poly(allylamine), poly(diallyldimethylammonium chloride), chitosan, poly(N-isopropyl acrylamide-co-acrylamide), poly(N-isopropyl acrylamide-co-acrylic acid), poly(L-lysine), diethylaminoethyl-dextran, poly-(N-ethyl-vinylpyridinium bromide), poly(dimethylamino)ethyl methacrylate), or poly(ethylene glycol)-co-poly(trimethylaminoethylmethacrylate chloride). Other cationic polymers will be apparent to those of skill in the art, and may be found, for example, in Polymer Handbook, 4th Edition, Edited by: Brandrup, E. H. Immergut, and E. A. Grukle; John Wiley & Sons, 2003).

The cationic polymers may be linear or branched. In some embodiments, the cationic polymers may range in size from about 500 Da to 25 kDa and may be branched or linear. For example, branched PEI with an average size of 1.8 kDa to 10 kDa may be loaded onto the nanoparticle core. The ratio of cationic polymer to nanoparticle may be varied depending on the desired result. The cationic polymer may be present from 1 to 50 wt. % of polymer per nanoconstruct, e.g., 5 to 40, 10 to 30%, 20 to 30%, 5 to 15%, 5 to 20%, 5 to 25%, 5 to 30%, 10 to 20%, 10 to 25%, or 25 to 40%, e.g., about 5, 10, 15, 20, 25, 30, or 35%. For example, as shown in Example III, PEI per MSNP at a weight ratio of 1:4 during initial coating and at a weight ratio of 1:4 during cross-linking resulted in 14 wt. % PEI per nanoconstruct if 10-kDa PEI was used or 16 wt. % if 1.8-kDa PEI was used (see, e.g., Table 5).

Figure 2A:
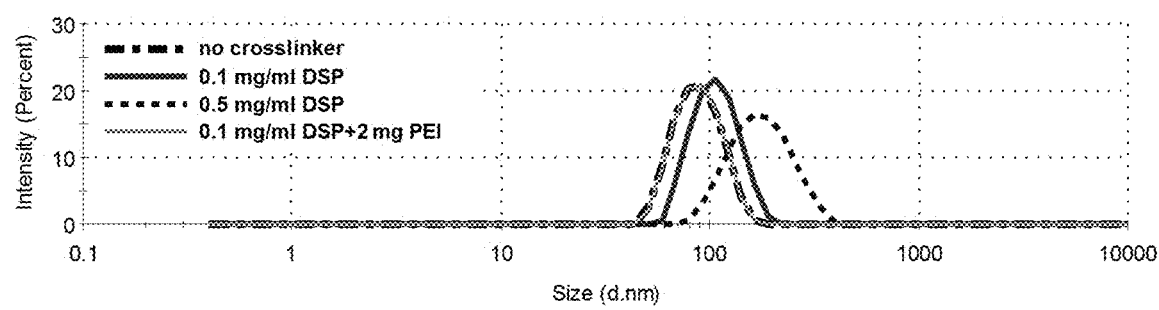
FIGS. 2A-2B show (A) the hydrodynamic size profile of MSNP modified as in FIG. 1 and synthesized under different crosslinking conditions and (B) a graph depicting the buffering capacity of three nanoconstructs with cross-linked 1.8-kDa PEI (T-NP$^{1.8C}$), non-cross-linked 10-kDa PEI (T-NP$^{10}$), and cross-linked 10-kDa PEI (T-NP$^{10C}$) measured in 150 mM NaCl. The cross-linking condition was "0.1 mg/ml DSP+2 mg PEI" as shown in FIG. 2A.
Figure 2B:
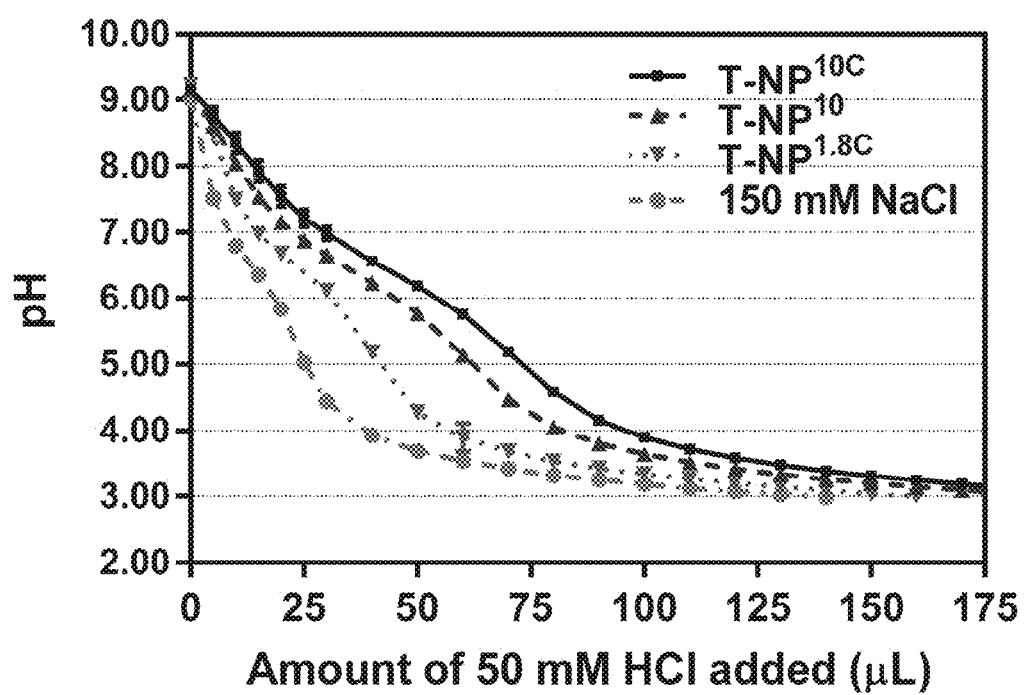

Endolysosomal escape and gene silencing efficacy is increased by increasing buffering capacity of the nanoparticles. Cross-linking the cationic polymers yields greater buffering capacity as shown in FIG. 2B. In some embodiments, the cationic polymers may be cross-linked, e.g., with a cleavable disulfide bond, pre or post coating on the nanoparticle. In some embodiments, the attached cationic polymers were cross-linked after binding to the nanoparticles, e.g., MSNP, using, for example, DSP (dithiobis[succinimidyl propionate]), DTSSP (3,3'-dithiobis(sulfosuccinimidyl propionate), and DTBP (dimethyl 3,3'-dithiobispropionimidate). The cross-linking may occur in the absence or presence of free PEI in the solution as shown in Example III and FIG. 2A. In other embodiments, the cationic polymers may not be cross-linked.

Stabilizers

A stabilizer may be conjugated to the nanoparticle and/or the cationic polymer, e.g., by any appropriate means. In some embodiments, a stabilizer is conjugated to an amine or other reactive group of a cross-linked cationic polymer coated on the nanoparticle (e.g., a MSNP). Exemplary stabilizers include, but are not limited to, polyethylene glycol (PEG), dextran, polysialic acid, hyaluronic acid (HA), polyvinyl pyrrolidone (PVP), polyvinyl alcohol (PVA), and polyacrylamide (PAM).

Figure 3A:
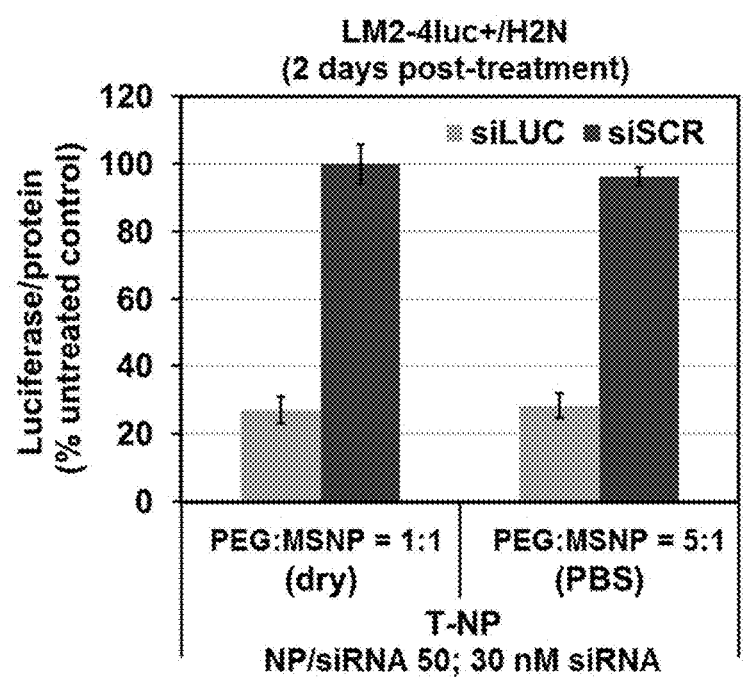
FIGS. 3A-3B show (A) the luciferase silencing efficacy of nanoconstructs made from 5-kDa PEG but with varied PEG loading conditions; 1:1 mass ratio of Mal-PEG-NHS:MSNP by adding Mal-PEG-NHS as dry powder directly to the MSNP-PEI suspension in PBS and stirring for 90-120 min or 5:1 mass ratio by first dissolving Mal-PEG-NHS in PBS prior to overnight mixing with MSNP-PEI suspension in PBS, and (B) the hydrodynamic size profile of MSNP modified as in FIG. 1(B) with PEG of various molecular weights (loaded as dry Mal-PEG-NHS at 1:1 mass ratio)

Stabilizers may have multiple chemically reactive groups, e.g., for attachment to the nanoparticle, cationic polymer, and/or other component. For example (e.g., Example IV), reactive stabilizer, e.g., PEG, derivatives may have two electrophilic moieties, such as maleimide-PEG-N-hydroxysuccinimidyl ester (Mal-PEG-NHS), which contains both a Michael acceptor and an activated ester. The stabilizer, e.g., PEG, used in conjunction with the compositions and methods of the invention generally has a molecular weight ranging between 500 Da-40 kDa, e.g., 2-10 kDa as shown in FIG. 3A. With 5-kDa PEG, the material is optimal in terms of size and PEG loading content (FIG. 3A). The stabilizer may be present from 1 to 50 wt. % of stabilizer per nanoconstruct, e.g., 5 to 30 wt. %, 10 to 20%, 10 to 25%, 5 to 15%, 5 to 20%, 5 to 25%, or 1 to 10%, e.g., about 5, 10, 15, 20, 25, 35, 40 or 45%. As shown in Example IV, Mal-PEG(5-kDa)-NHS per MSNP is used at a weight ratio of 1:1 to 5:1 during the synthesis (FIG. 3B), which results in about 6-23% of PEG per nanoconstruct (see Table 5).

Labeling Agents

Figure 37A:
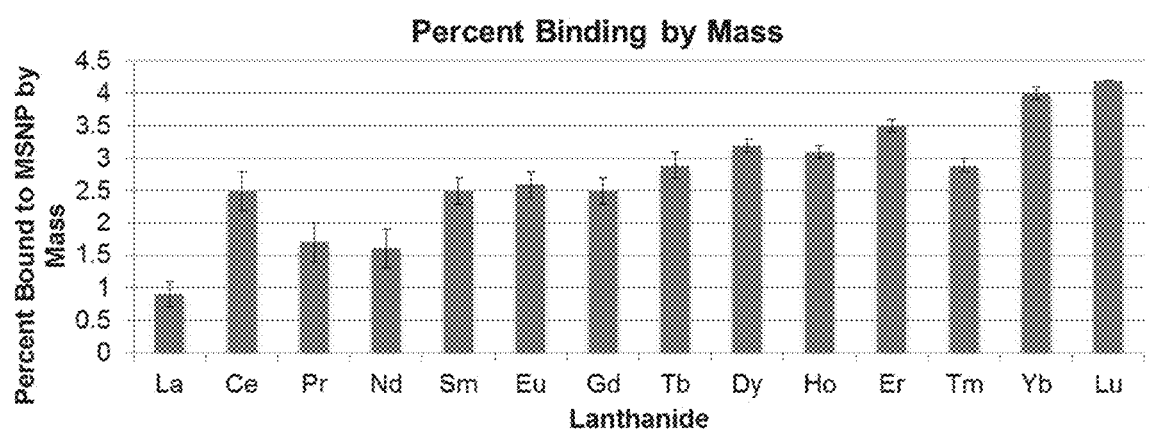
FIGS. 37A-37B show a series of lanthanides that were loaded inside the pores of MSNP nanoparticles in various amounts (A), as well as a series of fluorescence micrographs demonstrating specific staining of HER2+ cells and not HER2− cells with T-NPs containing Dylight550 (B).
Figure 37B:
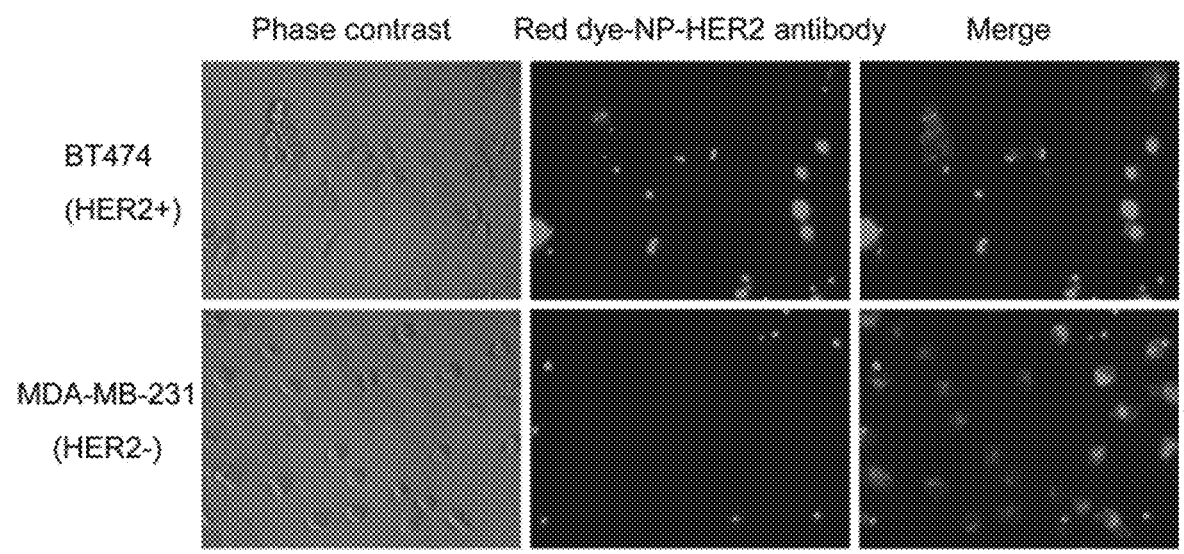

In some embodiments, the nanoconstruct may be labeled, e.g., with a lanthanide or fluorescent dye, e.g., as shown in Example XXIV and FIG. 37. A label may be any substance capable of aiding a machine, detector, sensor, device, column, or enhanced or unenhanced human eye from differentiating a labeled composition from unlabeled compositions. Examples of labels include, but are not limited to, radioactive isotopes (e.g., PET tracers), dyes, stains, quantum dots, gold nanoparticles, enzymes, nonradioactive metals (e.g., MRI contrast agents), magnets, biotin, protein tags, any antibody epitope, or any combination thereof. Exemplary fluorescent dyes include, but are not limited to, FITC, RITC, Cy™ dyes, amine-reactive Dylight® dyes, and amine-reactive Alexa Fluor® dyes. In some embodiments, lanthanides can be loaded onto hydroxyl, thiol, amine or phosphonate groups of nanoparticles, e.g., MSNPs, by covalent bonding or adsorption, e.g., as shown in FIG. 37A. Lanthanides can facilitate sample detection with high sensitivity and resolution, e.g., by mass spectrometry (FIG. 37A), while fluorescent dyes permit sample quantification by fluorescent imaging techniques, e.g., as shown in FIG. 37B. Nanoconstructs containing lanthanides such as gadolinium can also serve as MRI contrast agents for imaging disease sites.

In some embodiments, the labels, such as fluorescent dyes, may be loaded inside the pores of nanoparticles, e.g., amine-MSNPs via nucleophilic acyl substitution, e.g., between one or more nanoparticle-bound amines and an activated ester moiety (such as an NHS ester) appended to a fluorescent dye. Such labels produce nanoconstructs for fluorescence imaging applications as shown in FIG. 37B). Such a label may be added prior to or after loading of the cationic polymer and/or stabilizer. In further embodiments, the label may be attached to the cationic polymer, stabilizer, or other component prior to or after their attachment to the nanoparticle by any appropriate means.

Targeting Agents

Figure 19:
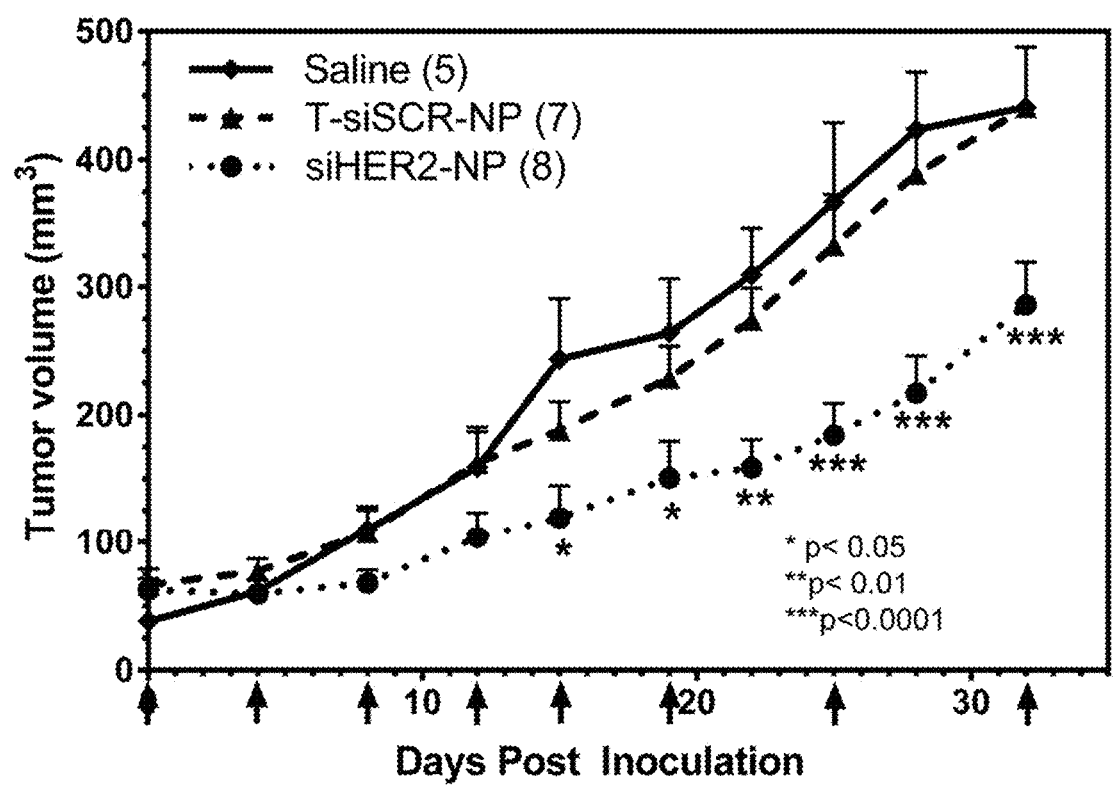
FIG. 19 is a graph depicting tumor growth in mice bearing orthotopic HCC1954 xenografts treated with siHER2-NP$^{10C}$ (no antibody) (n=8), T-siSCR-NP$^{10C}$ (n=7), or saline control (n=5) with the arrows indicating the days of i.v. injection. siHER2 or siSCR dose of 1.25 mg/kg and NP/siRNA ratio of 50.
Figure 20A:
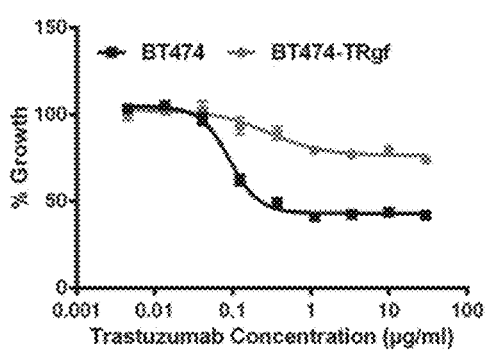
FIGS. 20A-20B show tumor growth in mice bearing trastuzumab-resistant tumor xenografts following nanoconstruct treatment.
Figure 20B:
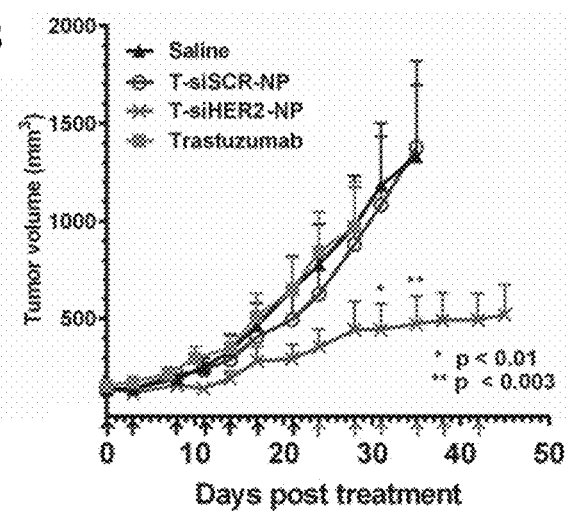

The nanoconstruct may be delivered specifically or nonspecifically. Nanoconstructs may be delivered to a site, e.g., for therapy, analysis, or diagnosis, such as a cell or tissue. The site may be in vivo or ex vivo. In some embodiments, the nanoconstructs may be delivered to tumors via the leaky vasculature of tumors. In some embodiments, the affinity of the cell or tissue, e.g., tumors, for cationic particles may permit nanoconstructs endowed with a positive charge due to the presence of cationic polymers to accumulate at the site, e.g., tumors and disease sites (see, e.g., FIG. 19 showing efficacy of siHER2-nanoparticle without targeting agent in tumor xenografts in mice). In other embodiments, the nanoconstructs may further include a targeting agent, e.g., for specific delivery of the nanoconstructs to sites such as tumors (see, e.g., FIGS. 16, 17, and 20 showing the efficacy of trastuzumab-conjugated siHER2-nanoparticle in tumor xenografts in mice). Targeting agents may be used to target a site and optionally to aid or induce internalization into a cell.

Exemplary targeting agents include, but are not limited to, monoclonal antibodies, single chain variable fragment (scFv) antibodies, other antigen binding fragments of antibodies, aptamers, small targeting molecules (e.g., ligands that bind to cell surface receptors such as N-acetylgalactosamine, mannose, transferrin, and folic acid), aptamers, carbohydrates, and peptides that have binding affinity to a cell or tissue, e.g., a tumor. The targeting agents may be attached to the nanoparticles, cationic polymer, or stabilizer by any appropriate means. In some embodiments, the targeting agents are trastuzumab (FIGS. 4 and 8), cetuximab (FIG. 8I), or HER2 scFV (FIGS. 21A-21E), which may be attached to a stabilizer, e.g., PEG, that is already attached to the nanoparticles. In some embodiments, the targeting agents, such as folic acid and transferrin, are first attached to a stabilizer, e.g., PEG, prior to attachment on the nanoparticle (FIGS. 21D-21E for folic acid (FA) conjugated nanoparticle). In further embodiments, the targeting agents, such as monoclonal antibodies, may have a therapeutic effect (see, e.g., FIGS. 9, 11, and 28). Exemplary monoclonal antibodies include, but are not limited to, anti-HER2 antibody, anti-EGFR antibody, anti-CD20 antibody, anti-VEGF-A antibody, anti-CD33 antibody, anti-CD52 antibody, and anti-TNFα antibody, such as alemtuzumab, bevacizumab, cetuximab, gemtuzumab, panitumumab, rituximab, infliximab, tositumomab, pertuzumab, and trastuzumab.

Figure 4A:
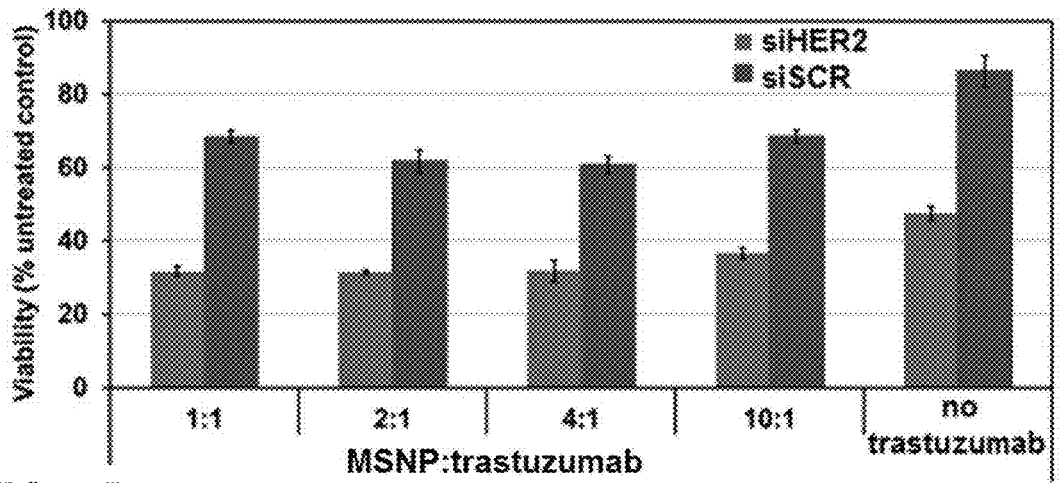
FIGS. 4A-4B are a series of charts showing the impact of varied mesoporous silica nanoparticle (MSNP) per trastuzumab mass ratio during synthesis on (A) cell viability, and (B) cellular uptake by BT474 cells.
Figure 4B:
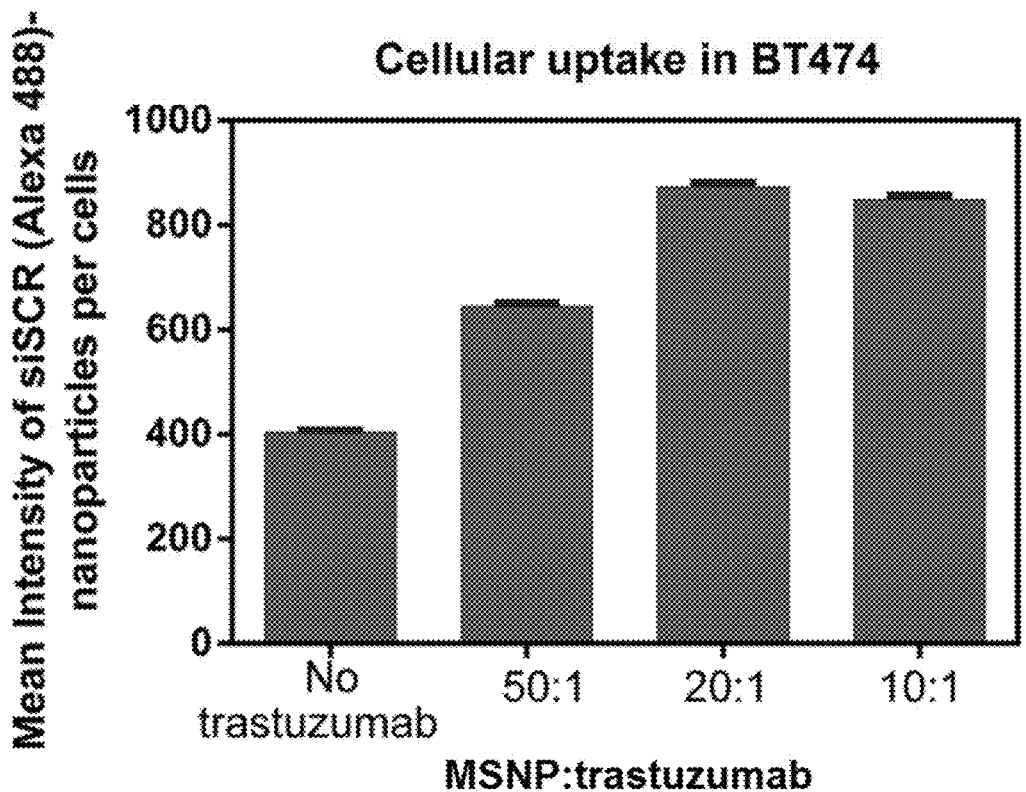

The targeting agents may be attached to the nanoconstructs by any means, and suitable conjugation chemistries are known in the art and described herein. In some embodiments (e.g., Example V), the targeting agent is thiolated and subsequently conjugated with Mal-PEG-PEI-MSNP via a thiol-maleimide reaction. In some embodiments (e.g., Example V), the targeting agents are first attached to the PEG stabilizer (e.g., FA or transferrin on PEG-NHS, commercially available) prior to conjugation to the nanoparticle by reaction of an NHS ester and an amine. The targeting agent may be present from 0.1 to 10 wt. % of targeting agent per nanoconstruct, e.g., 0.1 to 1% or 1 to 5%, e.g., 1 to 10% for antibody or 0.1 to 2% for scFV, e.g., about 1, 2, 3, 4, 5, 6, 7, 8, or 9%. For example, the MSNP per trastuzumab may be at the weight ratio of 50:1 to 1:1 (as shown in FIGS. 4A-4B) during the synthesis, resulting in 0.5 to 6 wt. % of trastuzumab per nanoconstruct (Table 5 showing 3 wt. % antibody if 10:1 ratio is used). In another example, 1-4 wt. % of HER2 scFV per MSNP during the synthesis results in 0.3-0.5 wt. % of HER2 scFV per nanoconstruct.

Small Molecules and Proteins

Figure 28A:
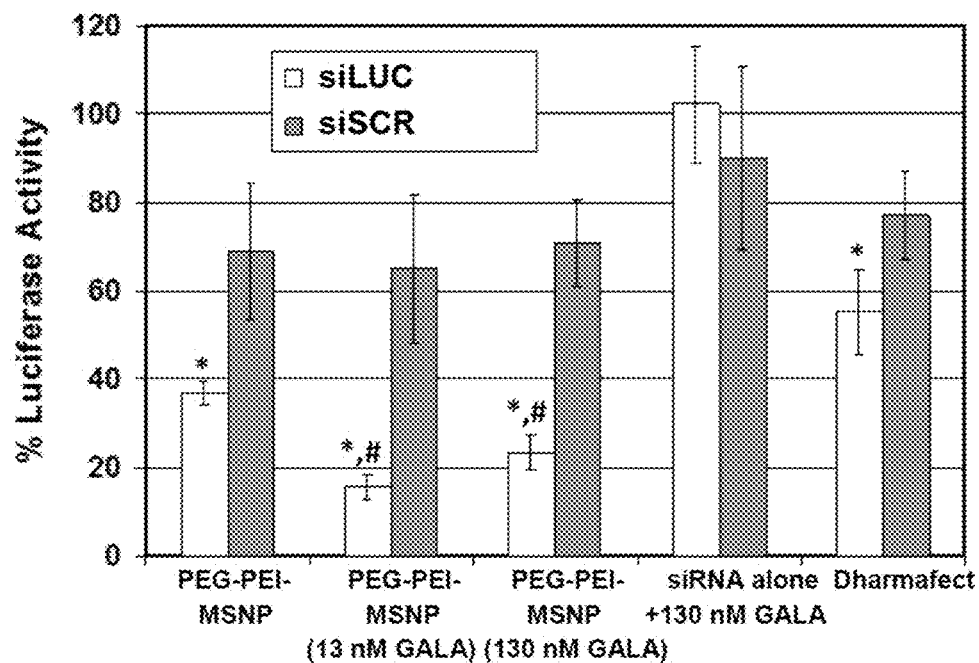
FIGS. 28A-28B are charts showing the ability of nanoconstructs to load and deliver GALA pore-forming peptide, which enhances endosomal escape of the siRNA-nanoconstruct, promoting luciferase silencing activity (A), as well as the effect of co-delivery of trastuzumab (T), paclitaxel (PTX), and siRNA (siHER2) loaded on nanoconstructs and administered to JIMT1 cancer cells (B). (A): 15 nM siRNA, NP/siRNA 50, activity measured 2 days post-treatment. (B): 30 nM siRNA, NP/siRNA 50, viability measured 5 days post-treatment.
Figure 28B:
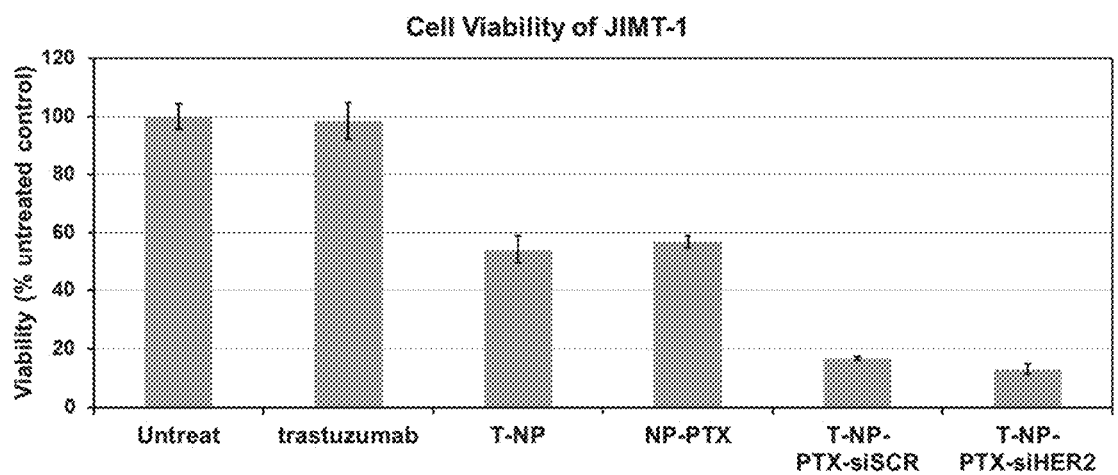
Figure 29:
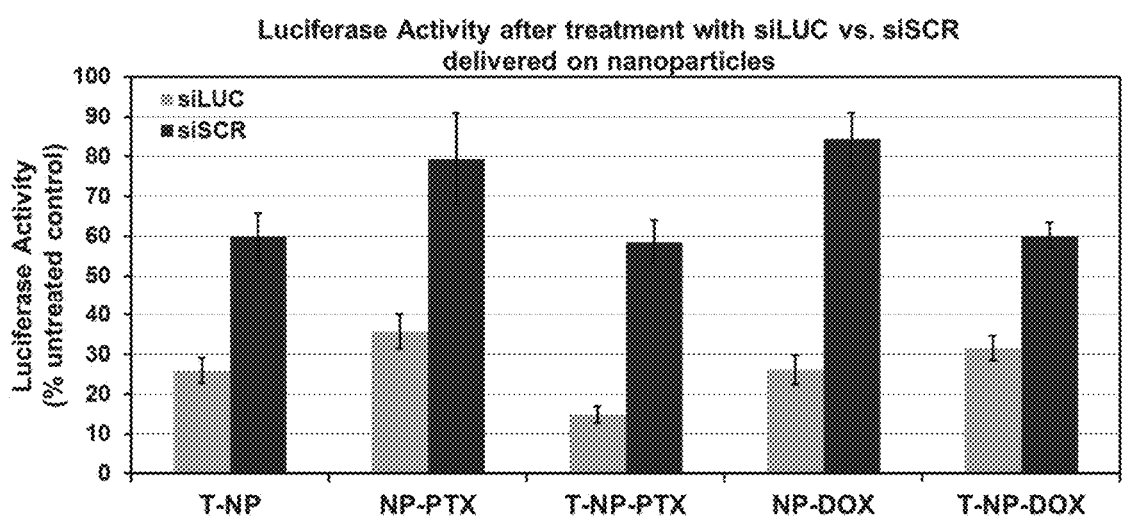
FIG. 29 is a chart showing that the loading of chemotherapeutics (paclitaxel, PTX, or doxorubicin, DOX) on the nanoconstructs did not significantly impair silencing efficacy of siRNA against luciferase (siLUC) (30 nM siRNA, NP/siRNA 50, activity measured 5 days post-treatment).
Figure 30:
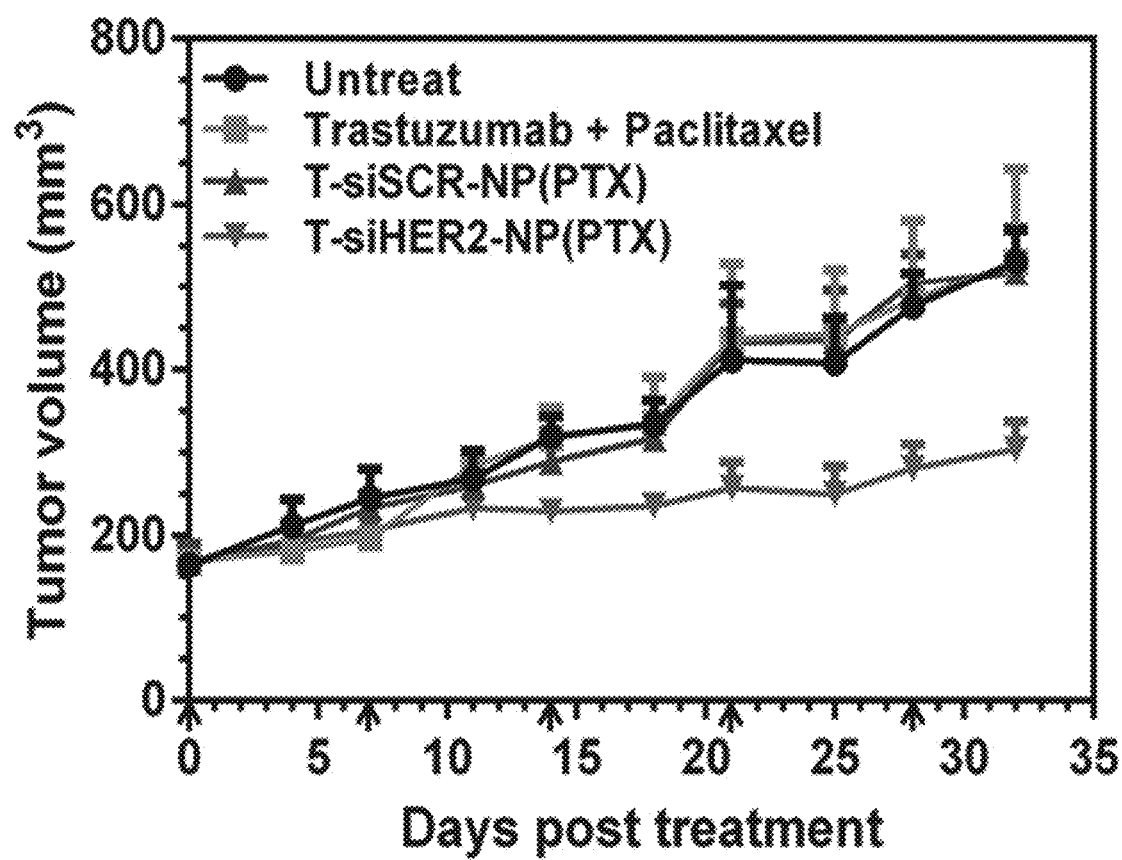
FIG. 30 is a chart showing the HCC1954 tumor growth inhibition effect of nanoconstructs loaded with both siHER2 and paclitaxel (T-siHER2-NP(PTX)) over those loaded with siSCR and paclitaxel (T-siSCR-NP(PTX)) or free drug counterparts (trastuzumab+paclitaxel). Arrows indicate injections (1.25 mg siRNA/kg, NP/siRNA 50).

In some embodiments, the nanoconstruct may be loaded with small molecules, proteins (i.e., other than targeting agents), or other therapeutic agents. Small molecules are molecules, typically with a molecular weight less than about 1000 Daltons, or in some embodiments, less than about 500 Daltons, wherein the molecule is capable of modulating, to some measurable extent, an activity of a target molecule. Exemplary small molecules such as peptides, small molecule inhibitors, chemotherapeutics, and other drugs may increase the therapeutic effects of the nanoconstruct, e.g., as shown in FIGS. 28-30. The small molecules may be located on the exterior of the nanoparticles, e.g., on PEI, and/or within the pores of the nanoparticle core, e.g., MSNP. Small molecules, such as small molecule inhibitors and other chemotherapeutic agents, may be selected based on the efficacy and specificity, e.g., in killing cancer cells over non-target cells. In addition to small molecules, small proteins such as cytokines with molecular weights less than about 50 kDa can also be loaded on the nanoparticle in the same manner as small molecules.

In some embodiments, chemotherapeutic agents such as paclitaxel, docetaxel, and doxorubicin may be loaded on nanoconstructs by hydrogen bonding with nanoparticle, e.g., MSNP, surface moieties (e.g., hydroxyl or silanol) and/or cationic polymer, e.g., PEI. Hydrophobic drugs (e.g., paclitaxel and docetaxel) can be loaded on the nanoconstructs during or after cationic polymer coating, e.g., with PEI in ethanol, while hydrophilic drugs (e.g., doxorubicin) can be loaded on the nanoconstructs after stabilizer coating, e.g., PEG, in PBS. The small molecule may be present from 0.01 to 50 wt. % of small molecule per nanoparticle, e.g., 0.1 to 30%, 1 to 30%, 1 to 20%, 1 to 10%, 1 to 5%, 0.1 to 1%, 0.5 to 5%, or 0.5 to 10%. For example, small molecule per MSNP is used at a weight ratio of 1:10 to 1:1, which results in 0.1 to 30% by weight of drug per nanoconstruct.

Exemplary chemotherapeutic agents include, but are not limited to, methotrexate; plicamycin (mithramycin); mitotane; mercaptopolylysine; pyrimidine analogs such as fluorouracil; anthracyclic antibiotics such as doxorubicin; maytansinoids such as ansamitocin; D-arabinosyl nucleosides, such as arabinosyl adenine; alkylating agents such as PAM, I-PAM, altretamine, procarbazine, busulfan, dacarbazine, temozolomide, thiotepa and dacarbazine; purine antagonists such as mercaptopurine; actinomycins such as dactinomycin; mitomycins such as mitomycin C; anti-steroids such as aminoglutethimide; anti-microtubules such as estramustine and vinblastine; anti-androgens such as flutamide; GnRH analogs such as leuprolide; megestrol acetate; estrogen receptor antagonists such as tamoxifen; amsacrine (m-AMSA); asparaginase (I-asparaginase); topoisomerase inhibitors such as etoposide (VP-16); cytokines such as interferon α-2a and interferon α-2b; podophyllotoxin derivatives such as teniposide (VM-26); arabinosyl cytosine; nitrogen mustards such as chlorambucil, cyclophosphamide, uramustine, ifosfamide, melphalan, bendamustine, mustine, and melphalan; nitrosoureas such as carmustine, fotemustine, lomustine, streptozocin, and semustine; platinum based anti-neoplastic agents such as carboplatin, cisplatin, triplatin tetranitrate and oxaliplatin; folate antimetabolites such as pemetrexed, raltitrexed, edatrexate, denopterin and cladribine; nucleoside analogs such as gemcitabine; purine nucleoside antimetabolites such as clofarabine; antimetabolites such as (N-((5-(((1,4-dihydro-2-methyl-4-oxo-6-quinazolinyl) methyl) methylamino)-2-thienyl)carbonyl)-L-glutamic acid); glutamine antagonists such as 6-diazo-5-oxo-L-norleucine; purine analogs such as fludarabine and thioguanine; prodrugs such as capecitabine and methyl aminolevulinate; mitotic inhibitors such as vincristine, vinorelbine, and vindesine; anthracyclines such as daunorubicin, doxorubicin, epirubicin, valrubicin, and idarubicin; anthracenediones such as mitoxantrone; glycopeptide antibiotics such as bleomycin; TNF inhibitors such as etanercept; aminolevulinic acid; tyrosine kinase inhibitors such as dasatinib, imatinib, nilotinib, lapatinib, neratinib, and erlotinib; epidermal growth factor receptor inhibitors such as gefitinib; protein kinase inhibitors such as sunitinib and vandetanib; platelet reducing agents such as anagrelide; proteasome inhibitors such as bortezomib; denileukin diftitox; pentostatin; pegaspargase; alagebrium (3-phenacyl-4,5-dimethylthiazolium; aminophylline; muramyl tripeptide; and mifamurtide. Other therapeutic agents are known in the art.

Oligonucleotides

In some embodiments one or more oligonucleotides may be attached to the nanoconstruct including, but not limited to, siRNA, miRNA, miRNA mimics, or antisense oligomers. Typically, the oligonucleotides will be capable of altering, e.g., reducing, expression of a target protein, e.g., by RNAi or antisense effect. Alternatively, the oligonucleotide may act as a probe in a cell or tissue of interest. Exemplary oligonucleotides include, but are not limited to, oligonucleotides that silence the expression of PLK1, AKT1/BCL2, HER2, EPS8L1, or HSP47 such as siPLK1, siAKT1/BCL2, siHER2, siEPS8L1, siHSP47, or miR-342-5P (see, e.g., Example XII and XX). Other targets are described herein. The oligonucleotide may be attached by any means. In some embodiments, the negatively charged siRNA is attached to the positively charged cationic polymer on the nanoparticle, e.g., MSNP, using an electrostatic interaction. The oligonucleotides may target one or more genes expressed in a cancer cell, such as one or more genes encoding a protein that promotes cell growth, tumor vascularization, or escape from apoptosis. In some embodiments, a single oligonucleotide may target a plurality of genes with varying potency. In other embodiments, a plurality of oligonucleotides may target a single gene. In further embodiments, a plurality of oligonucleotides may target a plurality of genes.

Figure 5A:
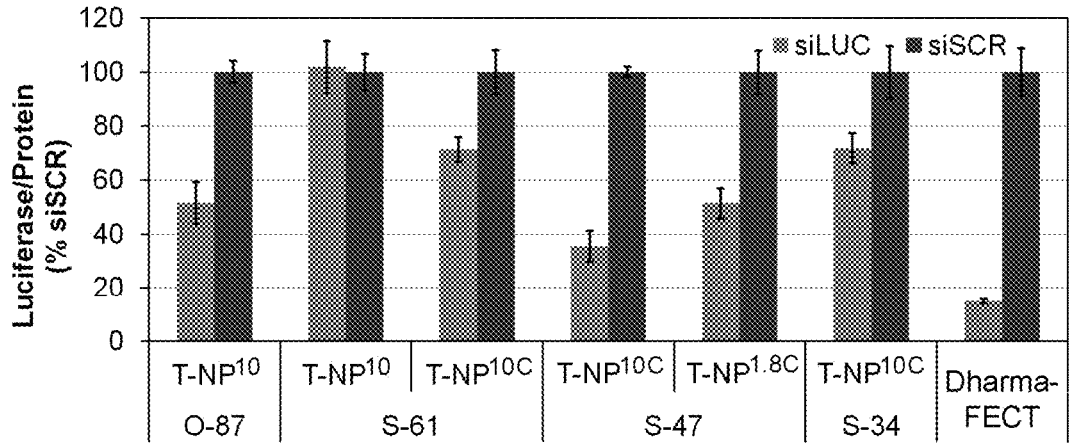
FIGS. 5A-5B are charts depicting the silencing of luciferase in LM2-4luc+/H2N upon treatment with 30 nM siLUC on trastuzumab-conjugated nanoconstruct (T-NP) at a NP/siRNA mass ratio of (A) 25 and (B) 50 measured at 48 hours post-transfection.
Figure 5B:
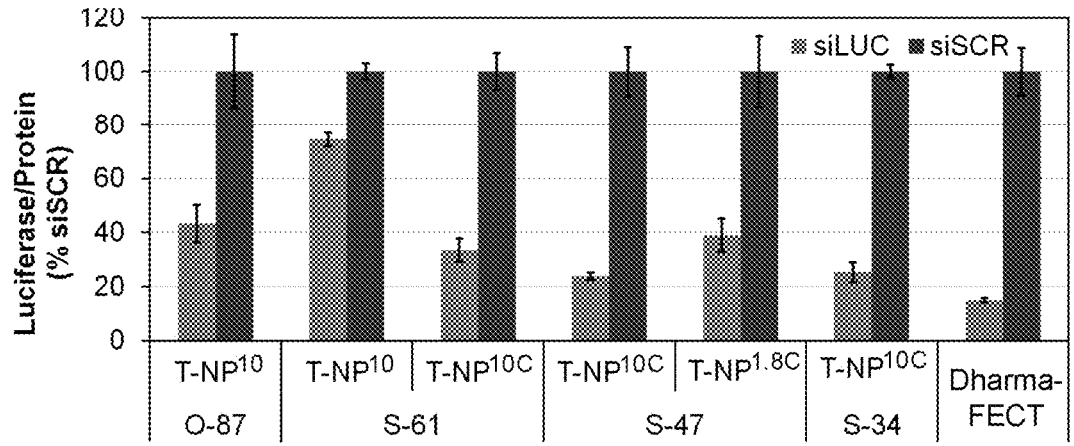
Figure 24A:
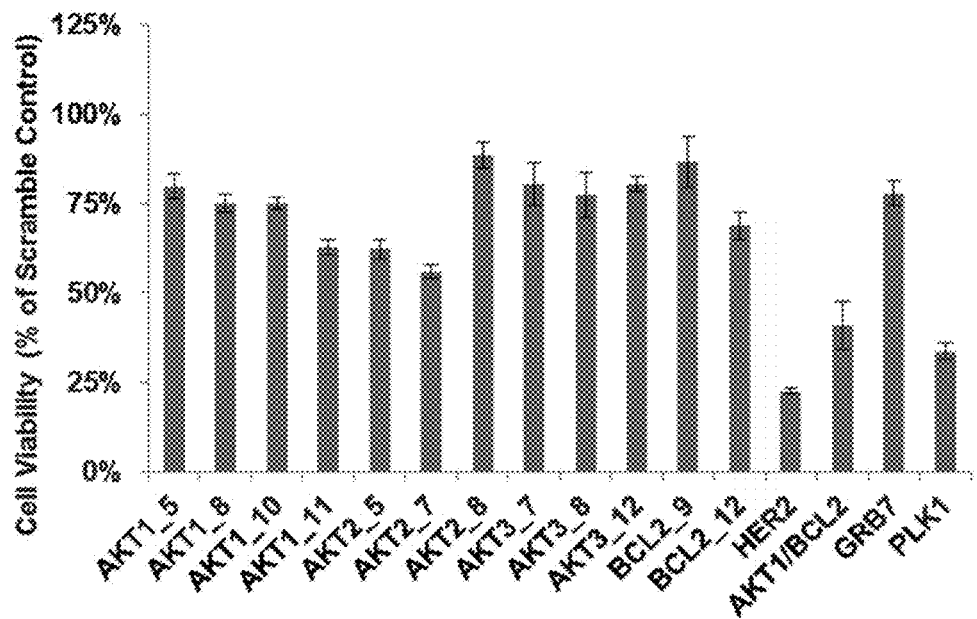
FIGS. 24A-24B are charts showing the viability of BT474 in response to 30 nM (each) of various siRNA treatments (A) and confirming protein knockdown in HCC38 cells by the dual-targeting siRNA (B) (siAKT1/BCL2; one strand targets AKT1 gene, and the other targets BCL2 gene).
Figure 24B:
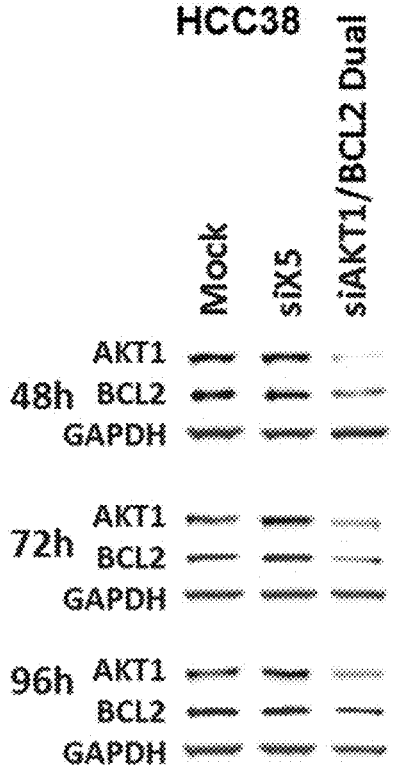
Figure 25:
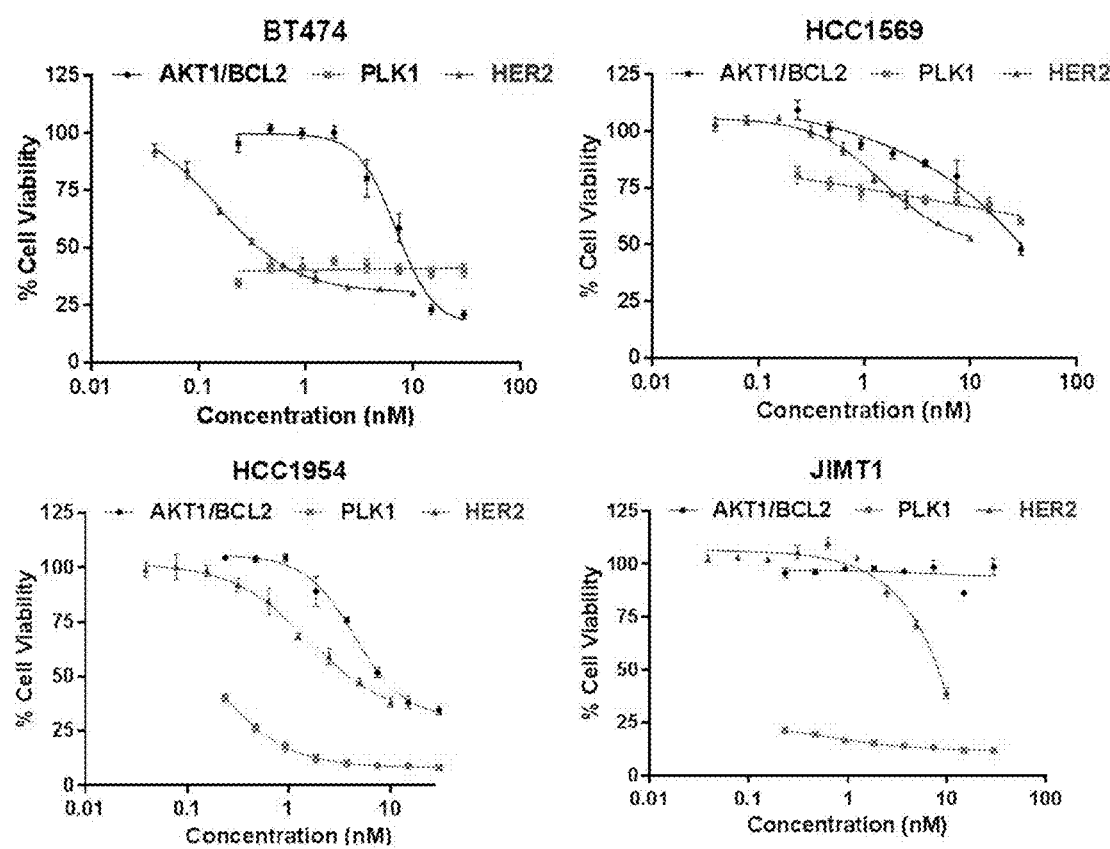
FIG. 25 is a series of graphs depicting dose response evaluation four days post-treatment with 30 nM siRNA targeting HER2, PLK1, and AKT1/BCL2 in BT474, HCC1569, HCC1954, and JIMT1 cell lines.
Figure 26:
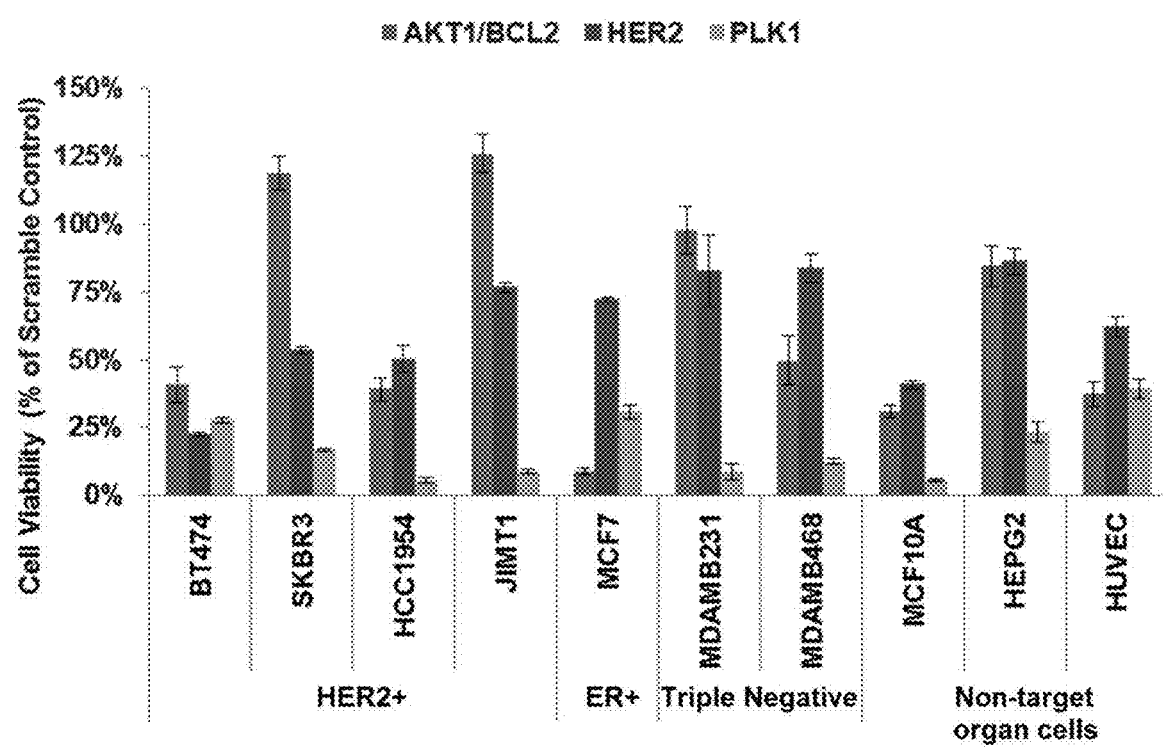
FIG. 26 is a graph depicting the effect of siRNA targeting of HER2, PLK1, and AKT1/BCL2 (delivered with commercial transfection agent, DharmaFECT™) on the viability of different breast cancer subtypes and non-target organ cells.
Figure 27A:
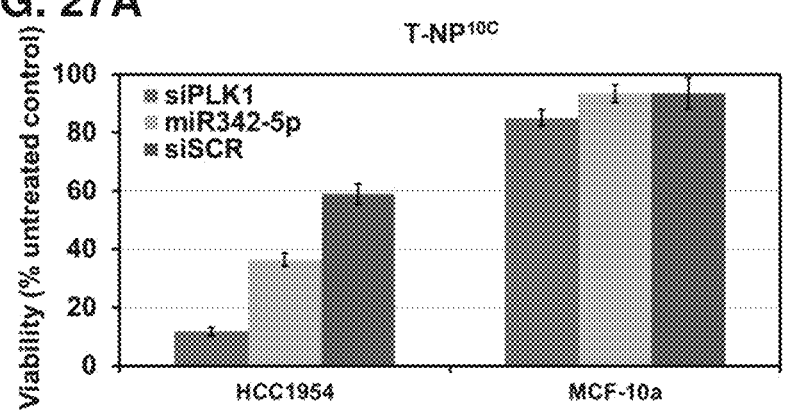
FIGS. 27A-27B are graphs showing enhanced treatment specificity to HER2+ breast cancer cell (HCC1954) compared to a non-tumorigenic breast epithelial cell line (MCF10A) with siPLK1 or miR342-5p delivered by the trastuzumab-conjugated nanoconstruct (T-NP$^{10C}$) (A), as well as the effect of delivery of siPLK1 or miR342-5p by commercial DharmaFECT™, which exhibit poorer treatment specificity to cancer cells over non-tumorigenic cells. All experiments performed with 30 nM siRNA or miRNA (B).

Oligonucleotides may be present from about 1% to 10% by weight, e.g., about 2% to about 4% by weight. For example, MSNP per siRNA (NP/siRNA) is used at the weight ratio ranging between about 10:1 to about 100:1 during the binding process, achieving complete binding. Optimal gene knock down efficacy is achieved at NP/siRNA of 25-50 as shown in FIGS. 5A-5B. For example, the MSNP-PEI-PEG (with or without a targeting agent) may be loaded with one or more siRNA sequences directed towards the target genes such as, but not limited to, siHER2, siAKT (isoforms 1, 2, 3), siBCL2, siAKT1/BCL2 (an siRNA duplex in which one strand can knock down AKT1 and the other can knock down BCL2, Table 1), siPLK1, siGRB7, and siEPS8L1. The screenings of these siRNA are shown in FIGS. 24-26. The nanoparticles may also be loaded with miRNA such as miR-342-5p under the same conditions with siRNA (FIG. 27A).

Exemplary siRNA sequences used herein are siHER2, siAKT1/BCL2, siRNA control designated siSCR, and a siRNA against luciferase designated siLUC. Specific sequences are shown in Table 1.

TABLE 1

Exemplary siRNA sequences

| siRNA | siRNA sequence |
|---|---|
| siHER2 | Sense: 5' CACGUUUGAGUCCAUGCCCAAUU 3' (SEQ ID NO. 1)<br>Antisense: 5' UUGGGCAUGGACUCAAACGUGUU 3' (SEQ ID NO. 2) |
| siLUC | Sense: 5' CGGAUUACCAGGGAUUUCAtt 3' (SEQ ID NO. 3)<br>Antisense: 5' UGAAAUCCCUGGUAAUCCGtt 3' (SEQ ID NO. 4) |

TABLE 1-continued

Exemplary siRNA sequences

| siRNA | siRNA sequence |
| --- | --- |
| siSCR | Sense: 5' UGGUUUACAUGUCGACUAA 3' (SEQ ID NO. 5)<br>Antisense: 5' UUAGUCGACAUGUAAACCA 3' (SEQ ID NO. 6) |
| siAKT1/ | Anti-Akt1: 5' AUUCAGUUUCACAUUGCUUGGUGAC 3' (SEQ ID NO. 7) |
| BCL2 | Anti-Bcl2: 5' GUCACCAAGAACUGUGACACAGAAG GG 3' (SEQ ID NO. 8) |

The exemplary siHER2 was selected by measuring the efficacy and specificity with which it reduced HER2 mRNA levels and growth in HER2+ cell lines but not HER2− cell lines. The dose of the siHER2 required to inhibit cell growth by 50% (GI50) was <5 nM in 19 out of 20 HER2+ cell lines (14 out of 20 cells did not respond to 30 μg/ml trastuzumab).

Figure 9A:
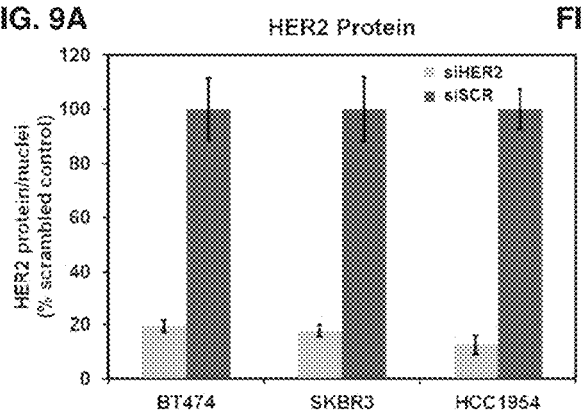
FIGS. 9A-9D show the HER2 silencing efficacy and cancer cell killing properties of siHER2 nanoconstructs.
Figure 9C:
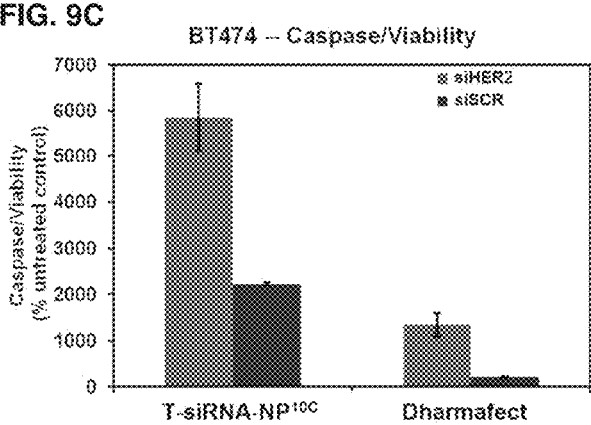
Figure 9D:
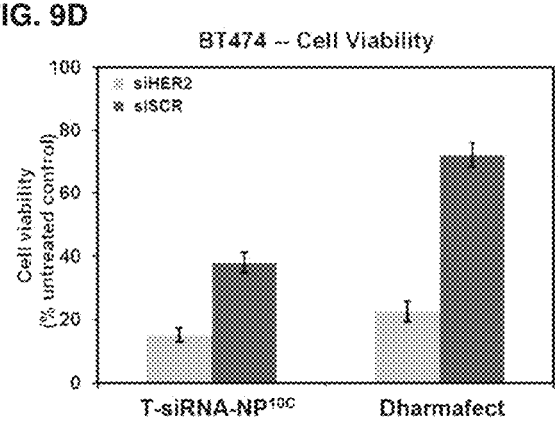
Figure 10:
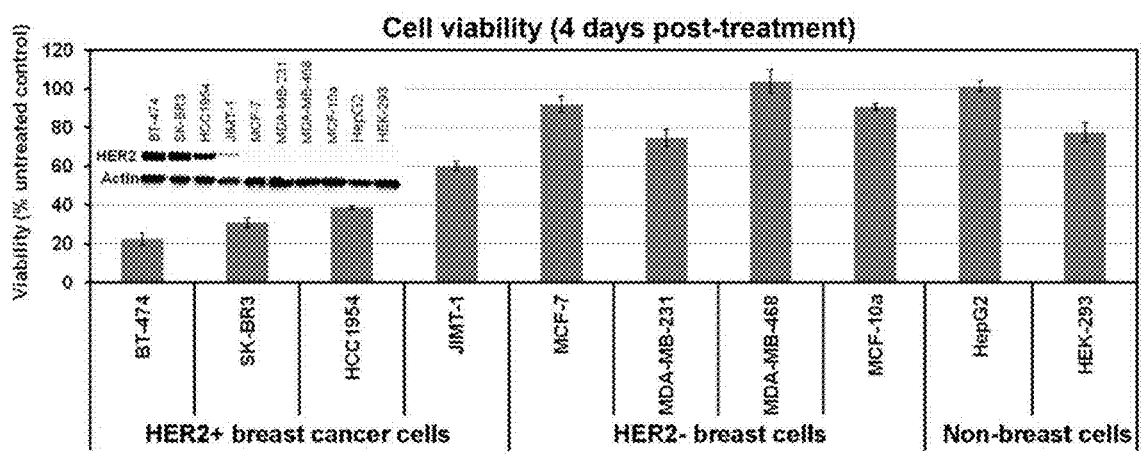
FIG. 10 shows that T-siHER2-NP$^{10C}$ treatment resulted in lower viability of HER2+ breast cancer cells but had little impact on HER2− breast cells and non-breast cells (4 days post transfection); with inset showing HER2 levels of the cells as measured by Western blot.
Figure 16A:
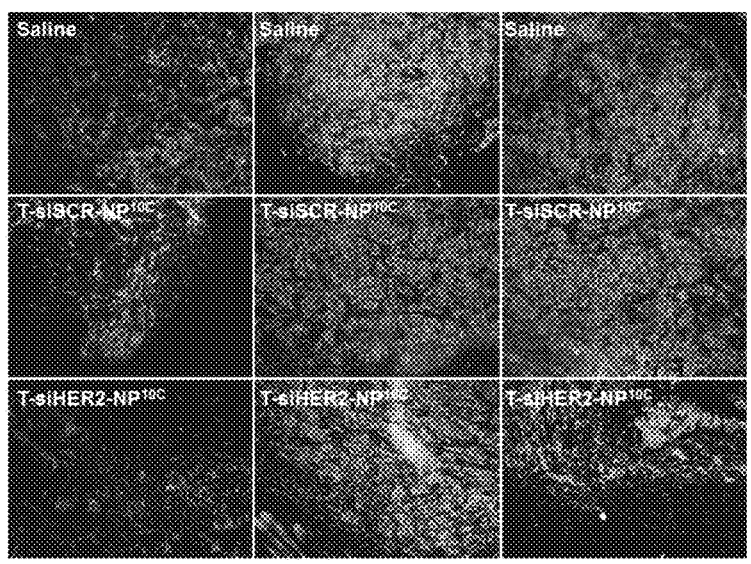
FIGS. 16A-16B show representative immunofluorescence images of HCC1954 tumor tissues collected from mice (n=4/group) at 4 days post i.v. injection with one dose of T-NP$^{10C}$ loaded with siHER2 or siSCR (1.25 mg/kg siRNA, NP/siRNA of 50) or PBS control (A) and quantitative HER2 levels of the tumor tissues (B).
Figure 16B:
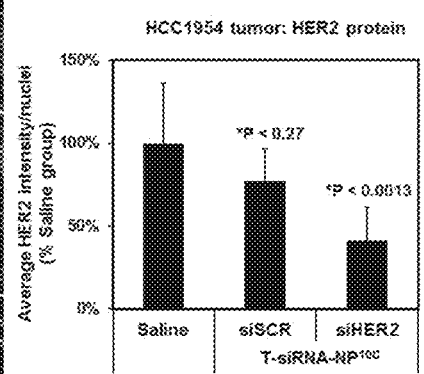

The exemplary siHER2 selected was bound to MSNP-PEI-PEG-Trastuzumab (T-NP) to create a nanoconstruct. The construct increases siRNA protection against enzymatic degradation in blood (FIGS. 6A-6E), enhances tumor-specific cellular uptake (FIGS. 8A-8I), and achieves over 80% of HER2 knockdown efficacy (FIG. 9A). The optimized nanoconstruct produced apoptotic death in HER2 positive (HER2+) breast cancer cells grown in vitro (FIG. 9C-D), but not in HER2 negative (HER2−) breast cancer or non-breast cells (FIG. 10). As seen in FIGS. 16A-16B, one dose of the siHER2-nanoparticles reduced HER2 protein levels by 60% in trastuzumab-resistant HCC1954 xenografts in mice and multiple intravenous doses administered over 3 weeks significantly inhibited tumor growth (p<0.004) (FIGS. 17A-17D). The material also had a therapeutic impact in another tumor model shown to be resistant to trastuzumab (FIG. 20).

Nanoconstruct Synthesis

Components may be bound to nanoparticles or other components by any means including covalent and electrostatic binding. Various conjugation chemistries are known in the art and described herein. In some embodiments, one or more of the components are bound to the surface of the nanoparticles. In other embodiments, one or more of the components are bound within the pores of the nanoparticle (e.g., MSNP). In further embodiments, one or more of the components are bound to each other. For example, in some embodiments, a targeting agent may be covalently bound to a stabilizer, which is covalently bound to the cationic polymer (e.g., via an amine), which is in turn electrostatically bound to the exterior of the nanoparticle, and a small molecule is bound to the interior surface of a pore. In some embodiments, the pore has a first opening at a first location on the exterior surface of the nanoparticle (e.g., MSNP) and a second, different opening at a second location on the exterior surface of the nanoparticle. Additional components may be bound anywhere along the length of the inside of the pore.

While nanoparticles, such as MSNPs, may be acquired commercially or created by any method, in some embodiments MSNPs are formed by combining a first surfactant with a second, different surfactant to form a first mixture, heating up the first mixture and adding a silica precursor to the first mixture to form a second mixture, holding the temperature for a period of time to generate MSNPs, and recovering the MSNPs by centrifugation. Surfactants can be removed by mixing the MSNP in acidic solvent under reflux conditions. In some embodiments, the first mixture may be heated prior to adding the silica precursor. In other embodiments, the first mixture may be at room temperature and the second mixture may be heated. The resulting MSNPs may have uniform or non-uniform particle size with high porosity, e.g., as shown in FIG. 1A.

For example, to form uniform MSNPs, cetyltrimethylammonium chloride (CTAC) may be combined with triethanolamine (TEA) in water, and heated to 95° C., while tetraethyl orthosilicate is added as shown in Example I. Variation of the amount of TEA while holding the amount of CTAC constant can be used to alter the size of the resulting MSNPs. In some embodiments, the amount of TEA is between about 100 to about 600 μL, about 200 to about 450 μL, or about 200 to about 350 μL. Non-uniform MSNPs may be created using a strong base, such as NaOH. For example, cetyltrimethyl ammonium bromide (CTAB) may be used as the surfactant and NaOH may be used as the base catalyst as shown in Example II.

Iron oxide nanoparticles can be purchased (e.g., Feraheme) or synthesized, e.g., as described in Example XXV. Gold and silver nanoparticles can be synthesized following various published protocols or purchased from vendors such as Sigma Aldrich, Nanocs, nanoComposix. Carbon nanotubes can be synthesized following various published protocols or purchased from vendors such as Sigma Aldrich, US Research nanomaterial, and American Elements.

In some embodiments, functional groups such as, but not limited to, thiol, amine, carboxylate, or phosphonate may be added to the nanoparticles, e.g., MSNPs, during synthesis through the use of one or more reagents, e.g., organosilanes such as, but not limited to, (3-aminopropyl)triethoxysilane and (3-aminopropyl)trimethoxysilane). Organosilanes may be added before or after the surfactants are removed from the MSNPs. Analogous reagents and other organic reagents, such as glutathione, mercaptopropionic acid, DMSA, PEG-thiol, oleic acid, and dextran may be employed to modify iron oxide nanoparticles, silver nanoparticles, gold nanoparticles, and carbon nanotubes. Functionalized nanoparticles can also be purchased directly, e.g., carbon nanotubes having surface modified with carboxylic acid, amide, polyaminobenzene sulfonic acid, octadecylamine, and PEG can be purchased from Sigma Aldrich.

The resulting nanoparticles, e.g., MSNPs after surface modification, may be of any appropriate size, e.g., from about 20 nm to about 200 nm, about 30 nm to about 100 nm, about 40 nm to about 200 nm, about 50 nm to about 200 nm, about 30 nm to about 80 nm, 40 nm to about 80 nm, about 30 nm, about 40 nm, about 30 nm to about 60 nm, about 50 nm, or about 60 nm. Exemplary hydrodynamic sizes are shown in FIGS. 1C, 2A, 3A, and 21D for final nanoconstructs with MSNP cores and FIG. 38A for final nanoconstructs with iron oxide cores.

Nanoconstruct Formulations and Methods of Use

Nanoconstructs may be formulated, as is known in the art, for therapeutic, diagnostic, or research use. Typically, such formulations for therapy or diagnosis include the nanoconstructs suspended in a pharmaceutically acceptable carrier. Nanoconstructs may be employed for in vivo or ex vivo use. Effects of the agents contained in the nanoconstruct may occur intracellularly or extracellularly. In particular, nanoconstructs may be employed to deliver oligonucleotides to cells to modulate, e.g., reduce, expression of a gene. Nanoconstructs may also be employed to delivery labels or other agents intracellularly or within an extracellular site.

The nanoconstructs may be used immediately upon formulation or may be stored. In some embodiments, the nanoconstructs may be lyophilized into dry states using a lyoprotectant, such as a sugar like trehalose. Optimal trehalose and lyophilization conditions may preserve the nanoconstruct in terms of particle size and charge (FIGS. 22A-B) and efficacy in terms of gene knock down efficacy (FIGS. 22C-D) compared to freshly made material. Nanoconstructs of the invention are stable for at least 6 months when lyophilized (FIGS. 23A-23E).

Effective amounts of a nanoconstruct for therapeutic administration will be readily determined by those of ordinary skill in the art, depending on clinical and patient-specific factors.

These and other effective unit dosage amounts may be administered in a single dose, or in the form of multiple daily, weekly or monthly doses, for example in a dosing regimen of twice per week for a 3 week cycle. In additional embodiments, dosages may be administered in concert with other treatment regimens in any appropriate dosage regimen depending on clinical and patient-specific factors. The amount, timing and mode of delivery of compositions of the invention comprising a disease treating effective amount of a nanoconstruct will be routinely adjusted on an individual basis, depending on such factors as weight, age, gender, and condition of the individual, the acuteness of the disease and/or related symptoms, whether the administration is prophylactic or therapeutic, and on the basis of other factors known to effect drug delivery, absorption, pharmacokinetics including half-life, and efficacy.

Formulations of the invention will ordinarily be selected to approximate a minimal dosing regimen that is necessary and sufficient to substantially prevent or alleviate the symptoms of the disease including cancer, fibrosis and inflammation in the mammalian subject, including humans. Therapeutic dosage and administration protocol will often include repeated dosing over a course of several days or even one or more weeks or years. An effective treatment regimen may also involve prophylactic dosage administered on a day or multi-dose per day basis lasting over the course of days, weeks, months or even years.

The compositions of the present invention may further include a pharmaceutically acceptable carrier appropriate for the particular mode of administration being employed. Dosage forms of the compositions of the present invention include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, effervescent agents and other conventional excipients and additives and/or other additives that may enhance stability, delivery, absorption, half-life, efficacy, pharmacokinetics, and/or pharmacodynamics, reduce adverse side effects, or provide other advantages for pharmaceutical use.

Some nanoconstructs of the invention are designed for parenteral administration, e.g. to be administered intravenously, intramuscularly, intratumorally, subcutaneously, or intraperitoneally, including aqueous and non-aqueous sterile injectable solutions which, like many other contemplated compositions of the invention, may optionally contain antioxidants, buffers, bacteriostats and/or solutes which render the formulation isotonic with the blood of the mammalian subject; and aqueous and non-aqueous sterile suspensions which may include suspending agents and/or thickening agents. The formulations may be presented in unit-dose or multi-dose containers. Additional compositions and formulations of the invention may include polymers for extended release following parenteral administration. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such materials are well known to those of ordinary skill in the pharmaceutical compounding arts. Parenteral preparations typically contain buffering agents and preservatives, and injectable fluids that are pharmaceutically and physiologically acceptable such as water, physiological saline, balanced salt solutions, aqueous dextrose, glycerol or the like. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

In some embodiments, the topical carrier used to deliver the nanoconstruct is an emulsion, gel or ointment. In other embodiments, the therapeutic compounds as described herein may be formulated in a spray formulation.

Emulsions, such as creams and lotions are a dispersed system comprising at least two immiscible phases, one phase dispersed in the other as droplets ranging in diameter from 0.1 µm to 100 µm. An emulsifying agent is typically included to improve stability. When water is the dispersed phase and an oil is the dispersion medium, the emulsion is termed a water-in-oil emulsion. When an oil is dispersed as droplets throughout the aqueous phase as droplets, the emulsion is termed an oil-in-water emulsion. Emulsions, such as creams and lotions that can be used as topical carriers and their preparation are disclosed in Remington: The Science and Practice of Pharmacy (Loyd V. Allen $22^{nd}$ ed. 2012), hereby incorporated herein by reference.

Ointments may be homogeneous, viscous, semi-solid preparation, most commonly a greasy, thick oil (oil 80%-water 20%) with a high viscosity. The ointment can be used as an emollient or for the application of active ingredients to the skin for protective, therapeutic, or prophylactic purposes where a degree of occlusion is desired.

A cream is an emulsion of oil and water in approximately equal proportions. It penetrates the stratum corneum outer layer of skin quite well. Cream is generally thinner than ointment, and maintains its shape when removed from its container.

The vehicle of an ointment/cream is known as the ointment base. The choice of a base depends upon the clinical indication for the ointment. The different types of ointment bases include, but are not limited to: hydrocarbon bases, e.g. hard paraffin, soft paraffin, microcrystalline wax and ceresine; absorption bases, e.g. wool fat, beeswax; Water soluble bases, e.g., macrogols 200, 300, and 400; Emulsifying bases, e.g. emulsifying wax, Vegetable oils, e.g. olive oil, coconut oil, sesame oil, almond oil and peanut oil. The therapeutic compounds are dispersed in the base and later get divided after the drug penetrates into the wound. Ointments/creams can be formulated incorporating hydrophobic, hydrophilic, or water-emulsifying bases to provide preparations that are immiscible, miscible, or emulsifiable with skin secretions. They can also be derived from fatty hydrocarbon, absorption, water-removable, or water-soluble bases. For example, a cream/ointment base can contain the active agent, white petrolatum, water, allantoin, EDTA, Stearyl alcohol, Brij 721, Brij 72, methylcelluloses, isopropyl myristate, Sorbitan monooleate, Polyoxyl 40 stearate, butylated hydroxytoluene, propylene glycol, methylparaben, propylparaben, deionized water to 100%, and buffer to neutral pH among other ingredients.

In another embodiment, the topical carrier used to deliver a compound of the invention is a gel, for example, a two-phase gel or a single-phase gel. Gels are semisolid systems consisting of suspensions of small inorganic particles or large organic molecules interpenetrated by a liquid. When the gel mass comprises a network of small discrete inorganic particles, it is classified as a two-phase gel. In some embodiments the liquid may be water or another aqueous media and the gel mass is defined as a hydrogel. Hydrogels can include, but are not limited to, alginates, polyacrylates, polyalkylene oxides, and/or poly N-vinyl pyrrolidone. The hydrogel may also be amorphous, i.e. a viscous gel as opposed to a solid such as a formulation of carboxymethylcellulose containing a humectant such as propylene glycol or glycerin. Exemplary amorphous hydrogels include, but are not limited to, maltodextra-beta glucan, acemannan, carboxymethylcellulose, pectin, xanthan gum, collagen, keratin and honey.

Nanoconstructs may be packaged into biodegradable capsules for oral administration. Alternatively, a nanoconstruct suspension may be installed inside the bladder. This is similar to intravesical chemotherapy, in which the drug administered to the bladder will come into direct contact with cancer cells in the bladder lining.

The invention disclosed herein will also be understood to encompass diagnostic compositions for diagnosing the risk level, presence, severity, or treatment indicia of, or otherwise managing diseases including, but not limited to, neoplastic diseases by contacting a labeled (e.g., isotopically labeled, fluorescent labeled or otherwise labeled to permit detection of the labeled compound using conventional methods) nanoconstruct to a mammalian subject (e.g., to a cell, tissue, organ, or individual) at risk or presenting with one or more symptom(s) of a cell proliferation disease, such as a cancer, and thereafter detecting the presence, location, metabolism, and/or binding state (e.g., detecting binding to an unlabeled binding partner involved in malignant cell receptor physiology/metabolism) of the labeled compound using any of a broad array of known assays and labeling/detection methods. In exemplary embodiments, a nanoconstruct is isotopically-labeled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. The isotopically-labeled compound is then administered to an individual or other subject and subsequently detected as described above, yielding useful diagnostic and/or therapeutic management data, according to conventional techniques.

Nanoconstructs may include various therapeutic moieties, such as targeting agents, oligonucleotides, and/or small molecules, and may have intrinsic therapeutic properties. For example, in some embodiments the nanoconstruct (e.g., a nanoconstruct containing a MSNP) may be an antioxidant. The antioxidant nanoconstruct can deliver siRNA that can reduce pro-fibrotic genes such as HSP47 and NOX4 as shown in FIGS. 31A-31D, decreasing the adverse effects of pro-inflammatory cytokines such as TGF-beta. This has proven to be effective at decreasing fibrotic markers such as COL I and alpha-SMA in vitro and in mouse models of fibrotic disease. Suitable effective unit dosage amounts of the active compounds for administration to mammalian subjects, including humans, can be readily determined by one of skill in the art. For example, for siRNA, the amount may range from about 0.01 to about 1 mg siRNA/kg, about 0.1 to about 0.75 mg siRNA/kg, about 0.1 to about 1 mg siRNA/kg per dose and any subset thereof.

Nanoconstructs containing a lanthanide and/or a fluorescent dye may be used as fluorescent, mass spectrometry, PET, and/or MRI probes for both in vitro and in vivo applications. In vitro, such nanoconstructs can be used to detect or quantify target proteins in tissue specimens or cells by immunofluorescence, flow cytometry, or mass cytometry (see, e.g., Example XXIV). In these applications, the targeting agents on the nanoconstruct will bind specifically with the protein receptors on the cells (e.g., EGFR or HER2 on cancer cells). In vivo, the nanoconstructs labeled with PET tracers, gadolinium chelates, or containing an iron oxide nanoparticle core can be used as PET or MRI contrast agents (see, e.g., Example XXVI) to detect diseases (e.g., cancer or inflammation). Additionally, nanoconstructs can be transfected into cells of interest (e.g., stem cells or immune cells) before such cells are infused to patients. This allows monitoring of these nanoconstruct-contained cells over time by non-invasive methods, such as fluorescence imaging, PET, and MRI.

Nanoconstructs made from iron oxide, gold, and silver nanoparticles can be used in hyperthermia treatment. Alternating magnetic fields and irradiation have been shown to heat up such nanoparticles, increasing temperature of tumors (e.g., up to 40° C.) in which the nanoconstructs are accumulated. This can enhance cargo release and/or induce cancer cell death.

The intrinsic properties of the nanoconstructs may have therapeutic benefits for cancer treatment. For example, in some embodiments, the antioxidant property of the nanoconstruct (from MSNP) may modulate reactive oxygen species in cancer cells, resulting in decreased migration and invasion of cancer cells (see, e.g., FIGS. 34A-34H). This effect was also confirmed in a mouse model of metastasis, as tumor spreading was observed to be attenuated in nanoconstruct-treated mice (see, e.g., FIGS. 35A-35H).

Additionally, amine groups, e.g., from PEI on nanoconstructs, are known to be highly effective chelators of copper. Copper is believed to be a cofactor for angiogenesis and hence metastasis in cancer (Brewer et al., 2000). Thus, the PEI-nanoconstruct may provide a therapeutic benefit similar to that observed for tetrathiomolybdate (TM, a copper chelator) in its clinical trial on metastatic solid tumor patients (Brewer et al, 2000). In this trial, five out of six TM-treated patients had mild copper deficiency (e.g. as assessed on the basis of a lower serum concentration of ceruloplasmin, a biomarker for total body copper status) and achieved stable disease. We also observed reduced serum ceruloplasmin in agreement with attenuated cancer metastasis and tumor burden with our nanoconstruct (see, e.g., Example XXIII).

In addition to cancer and fibrosis, the nanoconstructs are capable of delivering oligonucleotides to cells to alter gene expression (e.g., via RNA interference) and can thus also be used to treat other diseases involving aberrant gene expression. Exemplary siRNAs that can be incorporated into nanoconstructs of the invention may target genes listed in Table 2, e.g., to treat the corresponding diseases shown therein.

TABLE 2

Exemplary diseases that can be treated by gene modulation

| Category | Diseases | siRNA target |
|---|---|---|
| Ophthalmology | AMD | VEGF, RTP801, VEGF-R1 |
| | macular edema | VEGF, RTP801 |
| | chronic optic nerve atrophy | proNGF |
| Genetic disorder | pachyonychia congenita (genetic disease) | Keratin K6A |
| Oncology | chronic lymphocytic leukemia | Bcl-2 |
| | metastatic lymphoma | PLK1, LMP2, LMP7, MECL1 |
| | solid tumors | HER2, AKT1, AKT1, Bcl-2, AR, Myc, EGFR, Grb7, EPS8L1, RRM2, PKN3, Survivin, HIF1a, Furin, KSP, VEGF, eiF-4E |
| Inflammation | acute kidney injury | p53 |
| | delayed graft function | p53 |
| | familia adenomatous polyposis | b-catenin |
| Metabolic disease | Hypercholestrolemia | ApoB, PCSK9 |
| Fibrosis | liver fibrosis | HSP47 |
| | cystic fibrosis | CFTR |
| Dermatology | dermal scarring and fibrosis | CTGF, HSP47 |
| Viral Infection | Ebola infection | SNALP |
| | RSV infection | RSV nucleocapsids |
| Immunotherapy | Cancer | CD47, PD-L1, CTLA-4 |

The nanoconstructs may be used in the treatment of cancer, e.g., breast cancer. In some embodiments, the tumors may be resistant to monoclonal antibodies, small molecule inhibitors, and/or other chemotherapeutic agents, but still respond to siRNA delivered by nanoconstructs. In further embodiments, the siRNA targets the same genes/proteins that monoclonal antibodies and small molecule inhibitors target, but gene/protein suppression with siRNA is superior to that of antibodies or small molecule inhibitors and overcomes cancer resistance to the antibodies and small molecule inhibitors (see, e.g., Example XIII).

In some embodiments, more than one therapeutic agent may be used to increase effectiveness of the nanoconstruct. For example, FIGS. 28A-28B show the synergistic or additive effect of co-delivery of trastuzumab (HER2 antibody), chemotherapeutic paclitaxel (PTX), and siHER2 in terms of killing JIMT1, a multiple drug resistant HER2+ breast cancer cell. In further embodiments, as shown in FIG. 29, loading of chemotherapeutic agents such as paclitaxel (PTX) or doxorubicin (DOX) does not negatively impact the ability of siRNA on the same nanoconstruct to silence the targeted genes. FIG. 30 shows the effective inhibition of HCC1954 tumor growth in mice upon the treatment with nanoconstruct containing the three agents (T-siHER2-NP (PTX)).

As used herein, the terms "treat," "treating," "treatment," "therapeutic" and the like refer to reducing or ameliorating a disorder and/or symptoms associated therewith. It will be appreciated that, although not precluded, treating a disorder or condition does not require that the disorder, condition or symptoms associated therewith be completely eliminated.

By "effective amount" is meant the amount of an agent required to ameliorate the symptoms of a disease or arrest the progression of a disease relative to an untreated subject or to label a target, e.g., protein, cell, or tissue, sufficiently for detection. The effective amount of an active therapeutic agent for the treatment of a disease or injury varies depending upon the manner of administration, the age, body weight, and general health of the subject.

Various assays and model systems can be readily employed to determine the therapeutic effectiveness in the treatment of cancer, inflammation, fibrosis and other diseases. For example, effectiveness may be demonstrated using a complete blood count (CBC). The measurements taken in a CBC include a white blood cell count (WBC), a red blood cell count (RBC), the red cell distribution width, the hematocrit, and the amount of hemoglobin. Some signs of cancer which are visible in a CBC include a low hematocrit, a sharp decrease in the number of blood platelets, and a low level of neutrophils. An effective amount of a composition of the present invention may increase the levels measured in a complete blood count by 10%, 20%, 30%, 50% or greater increase, up to a 75-90%, or 95% or greater in comparison to individuals who have not been treated by the compositions described herein. The compositions as described herein may be effective in increasing all or some parts of the complete blood count in comparison to those treated with placebo. Effective amounts may also move the blood protein of an individual towards the optimal category for each type of protein.

Effectiveness in the treatment of neoplastic diseases may also be determined by a number of methods such as, but not limited to, microscopic examination of blood cells, bone marrow aspiration and biopsy, cytogenetic analysis, biopsy, immunophenotyping, blood chemistry studies, analysis of tumor biomarkers in blood, a complete blood count, lymph node biopsy, peripheral blood smear, visual analysis of a tumor or lesion, or any other method of evaluating and/or diagnosing malignancies and tumor progression known to those of skill in the art.

Effectiveness of the compositions and methods herein in the treatment of cancer or other disease may be evaluated by screening for markers in the blood depending on the specific cancer.

Within additional aspects of the invention, combinatorial disease treating formulations and coordinate administration methods are provided which employ an effective amount of a nanoconstruct and one or more secondary or adjunctive agent(s) that is/are combinatorially formulated or coordinately administered with the nanoconstruct to yield a combined, multi-active disease treating composition or coordinate treatment method.

Exemplary combinatorial formulations and coordinated treatment methods in this context employ the nanoconstruct, in combination with one or more secondary anti-tumor agent(s), or with one or more adjunctive therapeutic agent(s) that is/are useful for treatment or prophylaxis of the targeted (or associated) disease, condition and/or symptom(s) in the selected combinatorial formulation or coordinate treatment regimen. For most combinatorial formulations and coordinate treatment methods of the invention, a nanoconstruct is formulated, or coordinately administered, in combination with one or more adjunctive therapeutic agent(s), to yield a combined formulation or coordinate treatment method that is combinatorially effective or coordinately useful to treat neoplastic diseases and one or more symptom(s) of a secondary disease or condition in the subject. Exemplary combinatorial formulations and coordinate treatment methods in this context employ a nanoconstruct, in combination with one or more secondary or adjunctive therapeutic agents selected from, e.g., chemotherapeutic agents, anti-inflammatory agents, doxorubicin, vitamin D3, cytarabine, daunorubicin, cyclophosphamide, gemtuzumab ozogamicin, idarubicin, mercaptopurine, mitoxantrone, thioguanine, aldesleukin, asparaginase, carboplatin, etoposide phosphate, fludarabine, methotrexate, etoposide, dexamethasone, and choline magnesium trisalicylate. In addition, secondary therapies can include, but are not limited to, radiation treatment, hormone therapy and surgery.

In exemplary embodiments, a nanoconstruct and another agent will each be present in a disease treating/preventing amount (i.e., in singular dosage which will alone elicit a detectable alleviation of symptoms in the subject). Alternatively, the combinatorial formulation may comprise one or both nanoconstruct and another agent (wherein the other agent is not a nanoconstruct) in sub-therapeutic singular dosage amount(s), wherein the combinatorial formulation comprising both agents features a combined dosage of both agents that is collectively effective in eliciting the desired response.

To practice coordinated administration methods of the invention, a nanoconstruct may be administered, simultaneously or sequentially, in a coordinated treatment protocol with one or more of the adjunctive therapeutic agents contemplated herein. Thus, in certain embodiments a compound is administered coordinately with another agent and any other secondary or adjunctive therapeutic agent contemplated herein, using separate formulations or a combinatorial formulation as described above (i.e., comprising both a nanoconstruct and another agent). This coordinate administration may be done simultaneously or sequentially in either order, and there may be a time period while only one or both (or all) active therapeutic agents individually and/or collectively exert their biological activities. In another embodiment, such coordinated treatment methods are derived from protocols for the administration of one or more chemotherapeutics.

The pharmaceutical compositions of the present invention may be administered by any means that achieve their intended therapeutic or prophylactic purpose. Suitable routes of administration for the compositions of the invention include, but are not limited to, conventional delivery routes, devices and methods including injectable methods such as, but not limited to, intravenous, intramuscular, intraperitoneal, intraspinal, intrathecal, intracerebroventricular, intraarterial, subcutaneous and intranasal routes. Additional means of administration comprise topical application.

Aspects and applications of the invention presented here are described in the drawings and detailed description of the invention. Unless specifically noted, it is intended that the words and phrases in the specification and the claims be given their plain, ordinary, and accustomed meaning to those of ordinary skill in the applicable arts.

In the following examples, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. It should be noted that there are many different and alternative configurations, devices and technologies to which the disclosed inventions may be applied. The following examples are illustrative of disclosed methods. In light of this disclosure, those of skill in the art will recognize that variations of these examples and other examples of the disclosed method would be possible without undue experimentation.

EXAMPLES

Example I

Synthesis of Uniform Nanoparticle Cores

The sol-gel synthesis of mesoporous silica nanoparticle cores (MSNPs) was modified from previous reports (L. Pan et al., 2012; I. Slowing et al., 2007). For 47-nm MSNPs, nanoparticle (NP) (S-47), 0.15 M cetyltrimethylammonium chloride (CTAC) and 350 μL of triethanolamine (TEA) were mixed in 125 mL of water at 95° C. Then, 3 mL of tetraethyl orthosilicate (TEOS) was added, and the mixture was stirred for one hour. All chemicals were purchased from Sigma Aldrich, USA.

After mixing, the pellets were recovered from suspension by centrifugation, washed with a copious amount of ethanol, and dried overnight. The particles were then resuspended and refluxed in acidic methanol (0.6 M HCl in methanol) overnight to remove CTAC and TEA. Bare MSNPs were then washed with ethanol and dried in a desiccator overnight. MSNP (dry) size was measured with TEM (Phillips/FEI CM120/Biotwin TEM, Hillsboro, Oreg.) and hydrodynamic size with Zetasizer (ZS-90/Malvern, Malvern, U.K.). Varying the amount of TEA from 200-450 μl per 125 mL of reaction solution while holding the CTAC concentration constant at 0.15 M resulted in MSNP of different particle sizes; e.g., from 61±7 nm to 47±4 nm and 34±3 nm (dry size by TEM) as shown in FIG. 1A.

Multiple individual batches of mesoporous silica nanoparticles were created to determine the reproducibility of nanoparticle synthesis. As shown in Table 3, the hydrodynamic size of the S-47 MSNP core is highly reproducible, e.g., with a relative standard deviation (RSD) of 2.4% from 6 batches.

TABLE 3

| Reproducibility of nanoparticle synthesis. | |
| --- | --- |
| Batch | Hydrodynamic Size, Z-average ± SD (nm) |
| 1 | 61.1 ± 0.7 |
| 2 | 58.1 ± 0.6 |
| 3 | 59.7 ± 0.5 |
| 4 | 57.7 ± 0.9 |
| 5 | 60.8 ± 0.8 |
| 6 | 58.8 ± 0.3 |
| Average | 59.4 |
| % Relative standard deviation | 2.4 |

Example II

Synthesis of Non-Uniform Nanoparticle Cores

Non-uniform MSNPs (O-87) were synthesized in the presence of a strong base. 6 mM cetyltrimethyl ammonium bromide (CTAB) was dissolved in 240 mL of aqueous solution of pH 11.0 (adjusted by 2 M NaOH). When the temperature stabilized at 80° C., 2.5 mL of TEOS was added, and the reaction continued for 2 hours. After mixing, the pellets were recovered from suspension by centrifugation, washed with a copious amount of ethanol, and dried overnight. The particles were then resuspended and refluxed in acidic methanol (0.6 M HCl in methanol) overnight to remove CTAB. Bare MSNPs were then washed with ethanol and dried in a desiccator overnight. MSNP (dry) size was measured with TEM (Phillips/FEI CM120/Biotwin TEM, Hillsboro, Oreg.) and hydrodynamic size with Zetasizer (ZS-90/Malvern, Malvern, U.K.). These non-uniform nanoparticle cores were 87±14 nm in size (see, e.g., FIG. 1A).

Figure 1B:
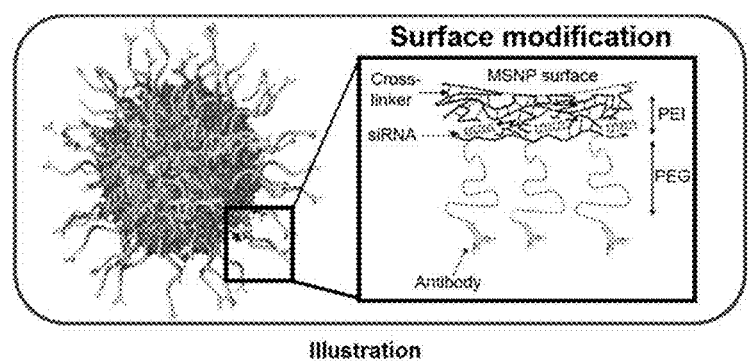
Figure 1C:
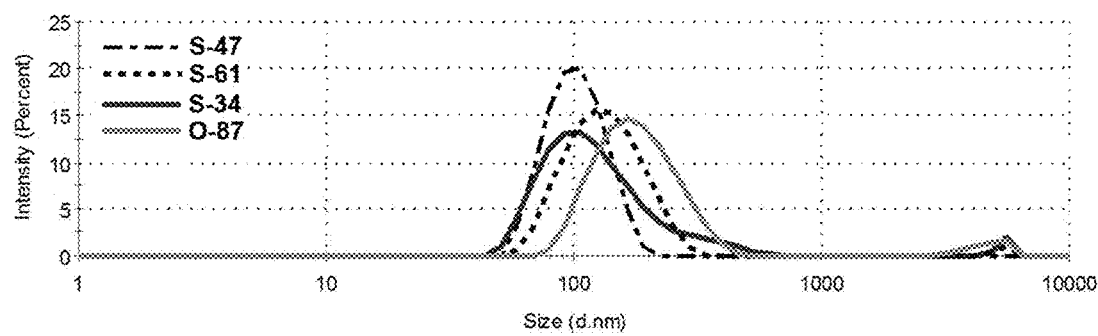

MSNPs prepared from Examples I and II were then coated layer-by-layer with cross-linked or non-cross-linked PEI, PEG, and targeting antibody. The nanoconstructs were then loaded with siRNA cargo as entailed in Examples III-IV. The characterization of compositions, size, and charge of the nanoconstructs are summarized in Example VII. FIG. 1B provides a schematic illustration of such surface decoration, and FIG. 1C shows the size of various nanoconstructs using different MSNP cores; all of which were surface modified with 10-kDa PEI (cross-linked for S-34, S-47, and S-61 MSNPs; non-cross-linked for O-87 MSNP), 5-kDa PEG, trastuzumab (HER2 antibody), and siRNA, respectively. FIG. 1C indicates that S-47 core yielded the most desirable hydrodynamic size of the final nanoconstruct.

Example III

Polyethylenimine (PEI) Attachment to MSNPs and Cross-Linking Methods

MSNPs prepared as described in Examples I and II were coated with PEI by shaking 10 mg MSNPs and 2.5 mg PEI in ethanol solution for 3 hours at room temperature. Next, the PEI-MSNP, was pelleted down. The material then underwent PEG attachment in Example IV or PEI cross-linking first prior to PEG attachment. For the PEI cross-linking method, the PEI-MSNP was re-suspended in ethanol solution containing 0 or 2.0 mg PEI (10 kDa) and 0.1-0.5 mg/ml DSP (DSP; dithiobis [succinimidyl propionate]; Lomant's Reagent) as a crosslinker. The solution was shaken for another 40 minutes. The particles were pelleted down, washed, and resuspended in PBS (pH 7.2). The hydrodynamic sizes of materials made under these various cross-linking conditions are shown in FIG. 2A, in which using 0.1 mg/ml DSP and 2 mg PEI during cross-linking yielded the most desirable size (similar to no cross-linker), while cross-linking alone without introducing 2 mg PEI causes aggregates due to inter-particle cross-linking.

Example IV

Polyethylene Glycol (PEG) Attachment to MSNPs

Mal-PEG-NHS was used to attach PEG on the nanoparticles (via an NHS ester). For PEG loading, 50 mg of mal-PEG-NHS was conjugated to the primary amine of PEI-MSNP (10 mg as MSNP) from Example III (using either cross-linked or non-cross-linked PEI-MSNP) in PBS buffer under shaking (20 hr, RT).

PEG:MSNP ratios. To reduce the usage of expensive Mal-PEG-NHS, Mal-PEG-NHS can be first dissolved in DMF or added as a dry powder directly to the PEI-MSNP suspension in PBS to limit the hydrolysis of NHS and enhance the PEG loading efficacy and reduce the reaction time. This reduces the Mal-PEG-NHS by 5 fold to a 1:1 weight ratio of Mal-PEG-NHS per MSNP and reduces the reaction time from 20 hr to 1.5 hr. For example, 10 mg of PEI-MSNP were re-suspended in 1 ml PBS. Then, 10 mg of Mal-PEG-NHS (as a powder) were added into the PEI-MSNP solution. The mixture was then vortexed for one minute and sonicated for five minutes to ensure re-suspension. The mixture was then further shaken for 1.5 hours. The resulting nanoconstructs were subsequently recovered by centrifugation and washed as aforementioned. This dry powder method avoids the use of potentially harmful DMF solvent and hence is preferable. It yields similar PEG loading (e.g., about 18%, Table 5) and siRNA protection (FIG. 6E) as those using 5:1 of Mal-PEG-NHS per MSNP ratio (see FIGS. 6A-C). The luciferase silencing efficacy using these two materials for delivering siRNA against luciferase (siLUC) (method outlined in Example VIII) is also the same (FIG. 3A).

Molecular Weights of PEG.

Figure 3B:
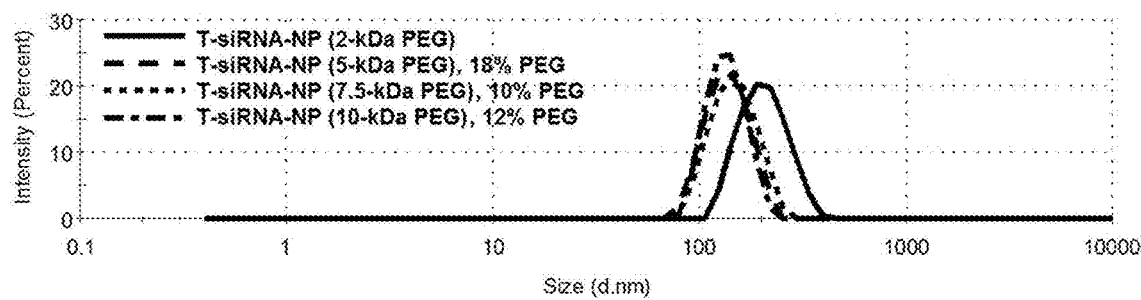

Different molecular weights of PEG were also optimized. PEGs with different molecular weights (2, 5, 7.5 and 10 kDa) were tested. The role of PEG is to provide a stealth layer to the nanoparticle, hence higher density of PEG loading (brush-like conformation) is more desirable than lower density of PEG loading (random coil conformation). FIG. 3B shows that 2-kDa PEG is not sufficient to prevent siRNA-nanoconstructs from aggregating into larger particles. A PEG of 5-kDa and above appears to prevent aggregation effectively. The amounts of PEG loaded on nanoconstructs with 5-, 7.5- and 10-kDa were quantified with the TGA to be 18%, 10% and 12% by mass, respectively. On a molar basis, 5-kDa PEG has around three times higher loading on the nanoconstructs than the 7.5-kDa or 10-kDa counterparts. Low molar loading of higher-MW PEGs suggests the PEG conformation is not brush-like at higher-MW PEG chains. 5-kDa PEG provided the highest PEG loading, suggesting an optimal brush-like stealth condition for our nanoconstructs and was used throughout the studies.

Example V

Conjugation of Targeting Agents (Antibody, Antibody Fragment, Folic Acid) on MSNP-PEI-PEG Antibody.

Antibody conjugation of MSNP-PEI-PEG utilized a thiol-maleimide reaction modified from the literature (P. Yousefpour et al., 2011, M. N. Koopaei et al., 2011). First, antibody (e.g., trastuzumab (T), cetuximab (C), or rituximab (R)) was thiolated with Traut's reagent (2-iminothiolane) in PBS (pH 8.0) under shaking with 50-fold molar excess of Traut's reagent for 2 hours and then purified by Zeba spin column—MW-40,000 (Thermo Fisher Scientific). Thiolated antibody was then mixed with MSNP-PEI-PEG at an antibody:nanoparticle mass ratio of 1:1 to 1:50. The reaction was completed overnight at 4° C. under shaking conditions (300 rpm). The material was pelleted down, resuspended in PBS, and washed with a copious amount of PBS. FIG. 4A shows the cell killing effect (method outlined in Example XII) upon delivering siHER2 (siRNA against HER2) with T-NP having different wt. % of trastuzumab. FIG. 4B shows the degree of cellular uptake (method outlined in Example XI) of T-NP having different wt. % of trastuzumab in BT474 (HER2+) cell line. It can be seen that antibody:nanoparticle mass ratio of 1:20 and 1:10 can equally enhance cellular uptake of T-NP, but cell killing started to reduce if too little antibody was used. For optimal cost and efficacy trade-off, 1:10 ratio was selected and used throughout unless specified otherwise.

Antibody Fragment (scFV).

Antibody fragment can be conjugated to the nanoparticle in a similar manner with antibody. Bacteria expressing a HER2 scFv clone (Poul et al., 2000) were grown overnight followed by expansion on the second day and stimulation with IPTG (thiogalactopyranoside) to produce scFv protein. The culture was subsequently pooled, and periplasmic bound scFv was extracted and purified on a Ni-NTA column according to manufacturer's protocol. Concentration of scFv was determined using a Nanodrop UV-Vis spectrometer, and purity was verified by gel electrophoresis. FIG. 21A shows the successful purification of HER2-scFv as indicated by the specific 25 kD band of scFv in the purified sample compared to the non-purified and wash eluent. FIG. 21B shows additional verification of scFv identity by probing with an antibody that specifically recognizes the 6× histidine tag present at the c-terminal of the scFv molecule. FIG. 21C shows HER2 scFV to be specific to HER2+ cells (BT474, SKBR3, JIMT1) over HER2− cells (MCF7 and MDAMB468). The scFv are attached to the end of the PEG chain on nanoconstructs by coupling cysteine of the scFv to the maleimide group on MSNP-PEI-PEG. Protein characterization indicated 0.4 wt. % of scFV per nanoparticle. FIG. 21D shows the size of HER2 scFV conjugated nanoparticles loaded with 3 wt. % siRNA; the size was measured in PBS. FIG. 21E shows the luciferase silencing efficacy (experiment outlined in Example VIII) of nanoparticles loaded with different amount of scFV in solution (1% or 4%, both of which resulted in 0.4 wt. % loading of scFv per nanoparticle).

Folic Acid.

NHS ester-PEG-Folic acid (FA) was obtained commercially from Nanocs. NHS-PEG-FA was attached on the nanoparticles (via an NHS ester) in a similar manner as Example IV. 2.5 mg of NHS-PEG(5 kD)-FA was conjugated to the primary amine of cross-linked PEI-MSNP (10 mg) from Example III in PBS buffer under shaking (1.5 hours, RT). NHS-PEG(5 kD) (5-20 mg) was added to further stabilize (bind with) the remaining amine active surface for another hour. FIG. 21D shows the hydrodynamic size of FA-siHER2-NP, and FIG. 21E shows the luciferase silencing efficacy of the material.

Example VI siRNA Loading on Targeting Agent Conjugated MSNP-PEI-PEG or MSNP-PEI-PEG The loading of siRNA was achieved by mixing trastuzumab-conjugated MSNP-PEI-PEG (designated as T-NP) or MSNP-PEI-PEG (NP) and siRNA at nanoparticle/siRNA (NP/siRNA) mass ratio of 10 to 100 in PBS solution (0.5 to 1 hour, room temp, 200 rpm shaking), which resulted in complete binding (no siRNA left in the supernatant) as monitored by fluorescent method and gel electrophoresis (see Example VII). Likewise, the loading of siRNA on HER2 scFV-NP and FA-NP were performed in a similar manner.

Example VII

Characterization of Nanoconstructs

After surface modification, the nanoconstructs had a hydrodynamic size of ~100 nm for the three uniform-sized core materials (S-34, S-47, S-61) and 200 nm for the non-uniform-sized core material (O-87) in water as shown in Table 4 and the size distribution histograms are shown in FIG. 10. All materials are positively charged due to the PEI. All materials have fairly narrow size distribution (PDI about 0.2) with the exception of S-34. The PEI and PEG loadings were analyzed by thermogravimetric analysis (TGA Q50, TA Instruments, Del.). Pierce Micro BCA kit (Thermo Fisher Scientific) was used to quantify the antibody or scFV loading on the nanoconstructs by analyzing for the remaining (unbound) antibodies in the supernatant. Likewise, fluorescent analysis of the remaining Dylight677-tagged siRNA in the supernatant was used to quantify siRNA loading, and was confirmed by gel electrophoresis. The composition of two representative materials are summarized in Table 5.

TABLE 4

TEM size, hydrodynamic size, and zeta potential of six different nanoconstructs.

| Material (MSNP core) | MSNP core size (nm) by TEM[a] | Surface modification[b] | Hydrodynamic size (DLS) Size (nm)[c] | PDI[d] | Zeta charge (mV) |
|---|---|---|---|---|---|
| O-87 | 87 ± 14 | T-NP[10] | 214 ± 22 | 0.22 | 22 ± 0.5 |
| S-61 | 61 ± 7 | T-NP[10] | 113 ± 1.0 | 0.20 | 18 ± 0.4 |
|  |  | T-NP[10C] | 131 ± 0.3 | 0.20 | 19 ± 3.7 |
| S-47 | 47 ± 4 | T-NP[10C] | 117 ± 0.5 | 0.19 | 25 ± 0.1 |
|  |  | T-NP[1.8C] | 117 ± 2.4 | 0.20 | 19 ± 4.0 |
| S-34 | 34 ± 3 | T-NP[10C] | 133 ± 4.1 | 0.37 | 19 ± 4.0 |

[a] Core size measured in dry state, average size of 50 particles.
[b] "10" stands for 10-kDa PEI; "1.8C" and "10C" stand for cross-linked 1.8-kDa and cross-linked 10-kDa PEI, respectively. All PEI-MSNP were then conjugated with 5-kDa PEG, and trastuzumab (T).
[c] Average of three measurements; the z-average diameter and polydispersity index (PDI) values were defined according to International Standard on DLS (ISO13321).
[d] PDI ranges from 0 to 1; smaller number indicates narrower size distribution; e.g., PDI <0.05 is considered monodisperse (one size only), while PDI >0.5 indicates a broad distribution of particle sizes.

TABLE 5

Composition of T-siRNA-NP (all reported as percent by mass of nanoparticle)

| Material | Surface modification | % PEI (by TGA) | % PEG (by TGA) | % Antibody (by BCA) | NP/siRNA mass ratio (fluorescent method) |
|---|---|---|---|---|---|
| S-47 | T-NP[10C] | 13.5 | 18.2 | 3 | Complete at NP/siRNA of 10 and above |
| S-47 | T-NP[1.8C] | 15.9 | 6.1 | 3 |  |

Example VIII

Gene Knockdown Efficacy of siRNA on Various Nanoconstructs

The LM2-4luc+/H2N cell line (over-expressing luciferase and HER2; J. M. du Manoir et al., 2006) was used for initial assessment of the nanoparticles for gene silencing efficacy when delivering siRNA against luciferase (siLUC). Cells were plated at 3000 cells/well in a 96-well plate. One day after seeding, cells were treated with siLUC-nanoparticles. The nanoparticles were loaded with siLUC at NP/siRNA ratio of 25 or 50 by mass. They were applied to each well at a fixed dose of 30 nM siLUC. The commercially available transfection agent, DharmaFECT™ (Dharmacon, Lafayette, Colo.), with the same siLUC dose served as a positive control. Non-targeting or scrambled siRNA (siSCR) was used throughout as a negative control. After overnight incubation (~20 hours), cells were washed once to remove the nanoconstructs and replenished with a complete media. At 48 hours post-treatment, cells were lysed and analyzed for luciferase activity by the Luciferase Glow Assay Kit (Thermo Fisher Scientific, Waltham, Mass.) and protein concentration by the BCA protein assay kit (Thermo Fisher Scientific), following manufacturer's protocols. Luciferase activity of the lysate was normalized with the corresponding protein concentration in the same well and reported as a percentage of the untreated or siSCR controls. All treatments were performed with replicates.

NP/siRNA Ratio.

We compared different nanoconstructs (four core sizes, loaded with PEI of 1.8-kDa or 10-kDa, cross-linked or not cross-linked) for luciferase silencing efficacy as shown in FIGS. 5A and B for NP/siRNA of 25 and 50, respectively. Silencing efficacy is defined as the reduced luciferase level due to the siLUC treatment vs. the siSCR control. The materials with NP/siRNA of 50 offered better gene silencing efficacy (per same dose of siLUC) (FIG. 5B) than those with NP/siRNA of 25 (FIG. 5A) due to the greater number of nanoparticles to which the cells were exposed. Materials with an NP/siRNA mass ratio of 50 were then used throughout unless specified otherwise.

Core Size.

Without cross-linking, smaller particles had reduced silencing efficacy compared to larger particles (e.g., see S-61 vs. O-87, both were modified with 10-kDa PEI, designated as T-NP$^{10}$ in FIG. 5).

Cross-Linking.

In FIG. 5, cross-linking indeed increased the silencing efficacy (e.g., T-NP$^{10C}$ vs. T-NP$^{10}$ on S-61). The smaller core size (S-34) resulted in aggregation (FIG. 10) and less silencing efficacy (FIG. 5A). The best hydrodynamic size (FIG. 10) and best silencing efficacy (FIG. 5) was achieved with S-47, modified with 10-kDa-PEI and with cross-linking (see T-NP$^{10C}$ on S-47) and is used throughout and referred to as "T-NP" unless specified otherwise.

Figure 7A:
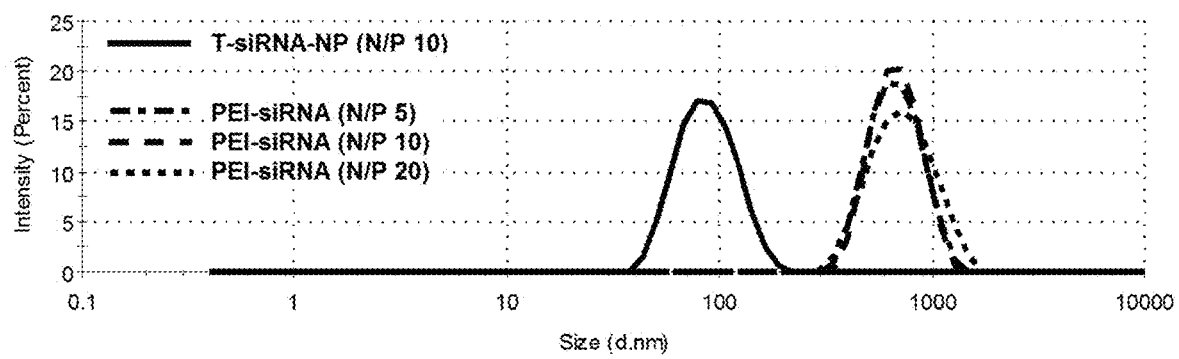
FIGS. 7A-7B shows that (A) nanoconstruct (T-siRNA-NP) has much smaller (desirable) hydrodynamic size and (B) better silencing efficacy than the PEI-siRNA polyplex counterparts (without MSNP core). N/P ratio is defined as the molar ratio of polymer nitrogen (N) to oligonucleotide phosphate (P).
Figure 7B:
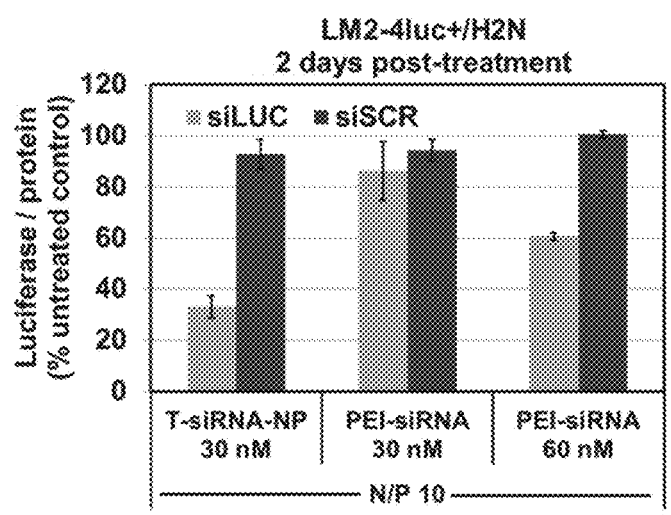

In addition, when compared to the PEI-siRNA polyplex (without MSNP core), T-NP was superior in terms of size and luciferase silencing efficacy, as shown in FIGS. 7A and B, respectively.

Example IX

Buffering Capacity of Cross-Linked-PEI Nanoconstructs

Internalized nanoparticles ultimately end up in peri-nuclear lysosomal vesicles. siRNAs must escape from these vesicles to the cytosol to silence expression. Increasing the buffering capacity of small nanoparticles in order to increase siRNA endosomal release based on the proton sponge effect principle was achieved by PEI cross-linking.

As outlined in Example III, the optimal PEI cross-linking condition was 0.1 mg/ml of DSP with 2 mg (free) PEI added to the binding solution. For measuring buffering capacity of cross-linked and non-cross-linked materials, the nanoparticles were suspended at 0.2 mg/mL in 150 mM NaCl (pH 9, pH adjusted with 0.05 M NaOH). Upon stabilization at pH 9.0, 5 µL of 0.05 M HCl was added and the solution was continuously stirred. When reaching steady state, the pH was recorded and the acid was added again. The process was repeated until the pH plateaued at around 3.0. The solution pH was then reported as a function of the amount of acid added.

FIG. 2B shows the buffering capacities of nanoparticles with cross-linked 1.8-kDa PEI (T-NP$^{1.8C}$), cross-linked 10-kDa PEI (T-NP$^{10C}$) and non-cross-linked 10-kDa PEI (T-NP$^{10}$) in 150 mM NaCl. As shown in FIG. 2B, the nanoparticles had buffering capacity in the order of T-NP$^{10C}$>T-NP$^{10}$>T-NP$^{1.8C}$. The cross-linking of the PEI on the nanoconstruct creates more secondary and tertiary amines yielding greater buffering capacity than primary amines, and promoting higher endosomal escape of siRNA based on proton sponge effect theory. This agrees well with the superior gene silencing efficacy of the cross-linked materials outlined in Example VIII.

Example X

Serum Protection Assay siRNA-nanoparticles were incubated with 50 v/v % human serum in PBS for a specified period of time (0, 0.5, 1, 2, 4, 8, 24, and 48 hours) at 37° C. under continuous shaking. At the end of each time point, the sample was mixed with proteinase K (200 µg/mL) and frozen at −80° C. to stop the enzymatic reaction. For the analysis, samples were thawed and mixed with 1.0 wt. % SDS in order to release siRNA from the nanoparticles. The sample was then mixed with an equal amount of 2× loading buffer and loaded into a 15% TBE-urea gel (BioRad). The gel ran at 100 V for the first 20 minutes and 150 V for another hour. The gel was then stained with SyBR Gold (Life Technologies) following the manufacturer's protocol and viewed in a UV chamber. The band intensity was analyzed by ImageJ software (National Institutes of Health, Bethesda, Md.). The fraction of intact siRNA was reported as a function of time that the siRNA-nanoparticles were in 50% serum. These results were compared to those obtained for free siHER2 without nanoparticles.

Figure 6A:
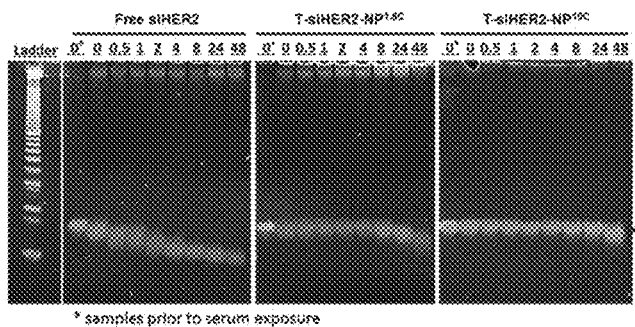
FIGS. 6A-6E show (A) the amount of intact siHER2 that survived enzymatic degradation in human serum as measured by gel electrophoresis, (B) quantification of corresponding intact siHER2, (C) the effect of PEG on siRNA protection from the enzymatic degradation (vs. MSNP-PEI and free siRNA), (D) the effect of PEG on preventing nanoconstructs from aggregating into larger sizes upon siRNA loading, and (E) nanoconstructs produced by an optimized PEG loading condition. Method optimization has been performed to reduce the amount of Mal-PEG-NHS usage from a 5:1 Mal-PEG-NHS:MSNP mass ratio to 1:1 as shown in FIG. 3A; the resulting material could still protect siRNA (FIG. 6E) in the same manner as that using a higher PEG ratio (5:1) (FIGS. 6A-6B).
Figure 6B:
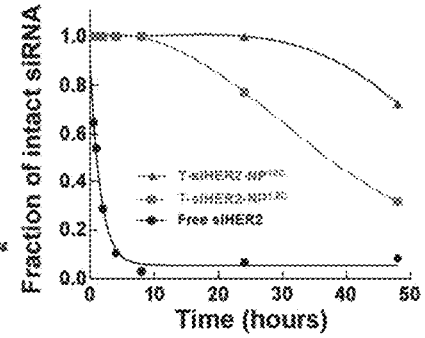
Figure 6C:
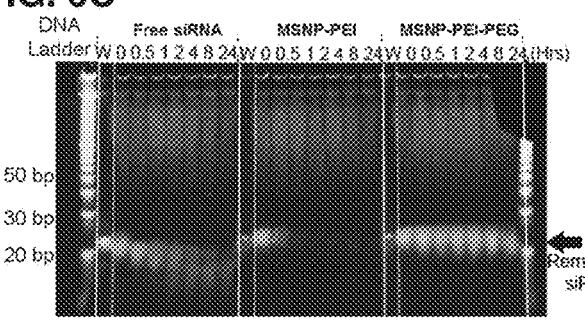

FIG. 6A shows the amount of intact siHER2 that survived enzymatic degradation as measured by gel electrophoresis. The corresponding siHER2 quantification based on the band intensity and location is shown in FIG. 6B. Without the nanoparticles, naked siHER2 was degraded within 0.5 hour (observed as bands shifted toward lower molecular weight), and its half-life was about 1 hour, in agreement with previous reports for other siRNAs (A. Mantei et al., 2008; D. M. Dykxhoorn et al., 2006). T-siHER2-NP$^{1.8C}$ fully protected siHER2 at least 8 hours, while T-siHER2-N$^{10C}$ fully protected siHER2 at least 24 hours. The siRNA on both nanoparticle platforms experienced much less degradation than on the cyclodextrin-based nanoparticle that went to clinical trials and showed antitumor efficacy (M. E. Davis, 2009). The siRNA on such material experienced 50% degradation within 12 hours, and 70% within 24 hours under 50% serum conditions (D. W. Bartlett et al., 2007).

Figure 6D:
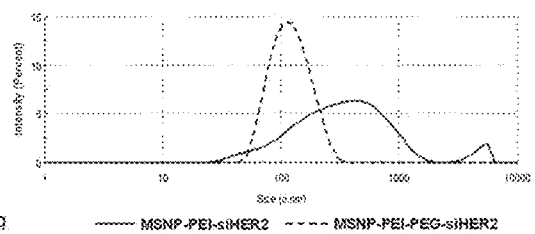
Figure 6E:
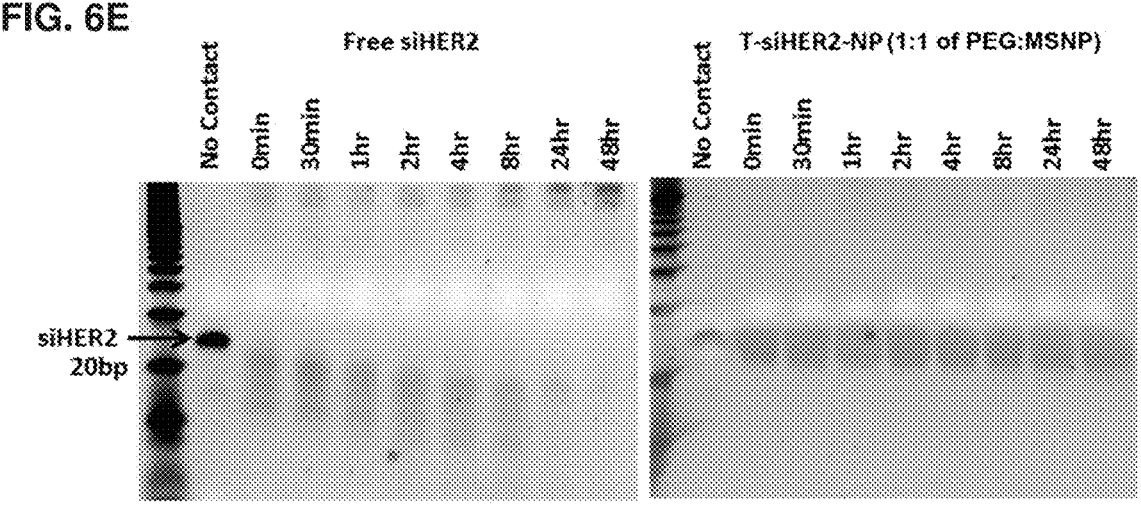

The higher siRNA protection for T-siHER2-NP$^{10C}$ compared to T-siHER2-NP$^{1.8C}$ is likely due to the higher PEG content of T-siHER2-NP$^{10C}$, e.g., 18.2% vs. 6.1% (Table 5). PEG provides a steric blocking effect (Z. Zhang et al., 2007; R. Gref, 2000) that reduces enzymatic degradation of siRNA (S. Mao et al., 2006). In a separate experiment (FIG. 6C), without PEG, siRNA on PEI-MSNP degraded faster than naked siRNA since positively charged PEI recruited more negatively charged enzymes to degrade siRNA. In addition, without steric PEG, significant aggregation of siRNA loaded nanoconstruct was observed (FIG. 6D). The steric effect of PEG also reduces binding of blood proteins to the nanoparticles (R. Gref, 2000).

Example XI

Cellular Uptake Analysis

Cells were harvested and resuspended in 1 million cells/ 150 µL/tube. Each tube was mixed with 150 µL of siSCR (tagged with Alexa-488) nanoconstructs in PBS (containing 100 μg nanoparticle). Upon nanoconstruct addition, cells were placed on a rocker in the cell incubator (37° C., 5% $CO_2$) for 0.5 or 2.0 hours. Cells were then washed (centrifuge at 115 g, 5 min) with 1 mL FACS buffer (1× Phosphate Buffered Saline (Ca/Mg++ free)+1 mM EDTA+25 mM HEPES pH 7.0+1% FBS (Heat-Inactivated) three times. Cells were then resuspended in 550 μL of FACS buffer, transferred to a 5-mL tube, and kept on ice until analysis. For cells stained with free antibody (for gating purpose), antibody labeling was performed on ice and under rocking conditions. Cells were stained with primary antibody (trastuzumab or rituximab: 2 μg per tube) for an hour, washed with PBS, stained with secondary antibody (Anti-human Alexa 488: 2 μg per tube) for 45 minutes, then washed 2 times with PBS, and re-suspended in 550 μL of FACS buffer before analysis. All tubes were counter-stained for cellular DNA with 2 μL of 5 mM DRAQS (Cell Signaling) for 15 minutes on ice. All tubes (except antibody-labeled cells for gating purpose) were then incubated with 500 μL of Trypan Blue (0.4% in PBS) to quench fluorescence outside of the cells, and subjected to flow cytometry analysis. 10,000 events (cells) were analyzed for each sample. The intensity was processed with FlowJo software (NIH, Bethesda, Md.).

The specificity with which trastuzumab-conjugated nanoconstructs were taken up by cells that over-express the HER2 protein was assessed. The nanoconstruct contained a scrambled siRNA and conjugated with trastuzumab (designated hereafter as T-siSCR-NP$^{1.8C}$ and T-siSCR-NP$^{10C}$) or with rituximab targeting CD20 (designated as R-siSCR-NP$^{1.8C}$ and R-siSCR-NP$^{10C}$). Cellular uptake of T-siSCR-NP$^{10C}$ and T-siSCR-NP$^{1.8C}$ in HER2+ breast cancer cell lines, BT474 and SKBR3, and the HER2− cell line MCF-7 was measured at 0.5 or 2.0 hours post exposure to the nanoconstructs. The siSCR was tagged with the fluorescent reporter, Alexa 488, for these experiments to enable quantitative analysis of siSCR uptake. R-siSCR-NP$^{10C}$ and R-siSCR-NP$^{1.8C}$ served as a negative control since BT474, SKBR3 and MCF-7 cells do not over-express CD20. The amount of Alexa 488-tagged siSCR inside individual cells was measured using flow cytometry. FIG. 8A-C shows that T-siSCR-NP$^{10C}$ were taken up effectively (>90%) into HER2+ cells (BT474 and SKBR3), but not HER2− cells (MCF7) and that uptake increased by extending the exposure time from 0.5 hr to 2 hr. Furthermore, uptake of T-siSCR-NP$^{10C}$ was greater than T-siSCR-NP$^{1.8C}$. R-siSCR-NP$^{10C}$ and R-siSCR-NP$^{1.8C}$ were not taken up efficiently by any of the cell lines, indicating the ability of T to promote cellular uptake to HER2+ cells. FIG. 8D illustrates HER2 protein expression in the three cell lines being evaluated. FIG. 8E-G show the average intensity of Alexa 488-tagged siSCR signal per cell and the same trend can be observed. This confirms that trastuzumab-conjugated nanoconstructs enter cells primarily by a HER2-receptor mediated endocytosis mechanism and not by adsorptive endocytosis of positively charged particles as reported for PEI-MSNP (H. Zhang, et al., 2011).

As another example, cetuximab (anti-EGFR antibody) was used as a targeting agent on the nanoconstruct, named C-NP, in a similar manner as T-NP. C-NP also showed preferential uptake to EGFR+ cells over EGFR− cells (FIGS. 8H-I).

Example XII

HER2 Protein Knockdown and Cell Viability

HER2+ breast cancer cells (BT474, SKBR3 and HCC1954) were seeded in a 96-well plate for 24 hours prior to treatment. Nanoconstructs were loaded with siHER2 or siSCR at NP/siRNA 50. siRNA dose was fixed at 60 nM. Media was switched to complete media after overnight incubation. Three days after treatment with nanoconstructs, cells were fixed and analyzed for HER2 protein expression by immunofluorescence. HER2 mRNA and β-actin mRNA levels were analyzed at 48 hours post-treatment using the Quantigene 2.0 Reagent System (Panomics) following the manufacturer's protocol. The HER2 mRNA level was then normalized with β-actin mRNA (housekeeping gene) and reported as the percentage of the siSCR control. Cell viability and apoptosis were analyzed four days post-treatment using the CellTiter-Glo® Luminescent Assay (Promega) and the Caspase-Glo® 3/7 Assay Systems (Promega), respectively. Caspase activity was normalized with the cell viability. Both were reported as a percentage of the untreated control.

Figure 9B:
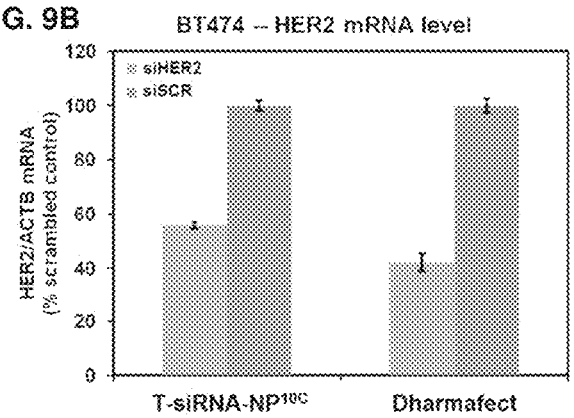

The efficiency of T-siHER2-NP$^{10C}$ in inhibiting HER2 mRNA levels and HER2 protein expression in the HER2+ breast cancer cell lines, BT474, SKBR3, and HCC1954 was assessed. As shown in FIG. 9A, T-siHER2-NP$^{10C}$ reduced HER2 levels by 81-93% compared to T-siSCR-NP$^{10C}$. As shown in FIG. 9B, there was 44% reduction in HER2 mRNA relative to siSCR control. The cleaved Caspase 3 and 7 assay for apoptotic markers shows that apoptotic activity was three-fold greater after treatment with T-siHER2-NP$^{10C}$ than with T-siSCR-NP$^{10C}$ (FIG. 9C). This is consistent with reduced cell viability (using a cellular ATP level assay) shown in FIG. 9D.

Figure 11:
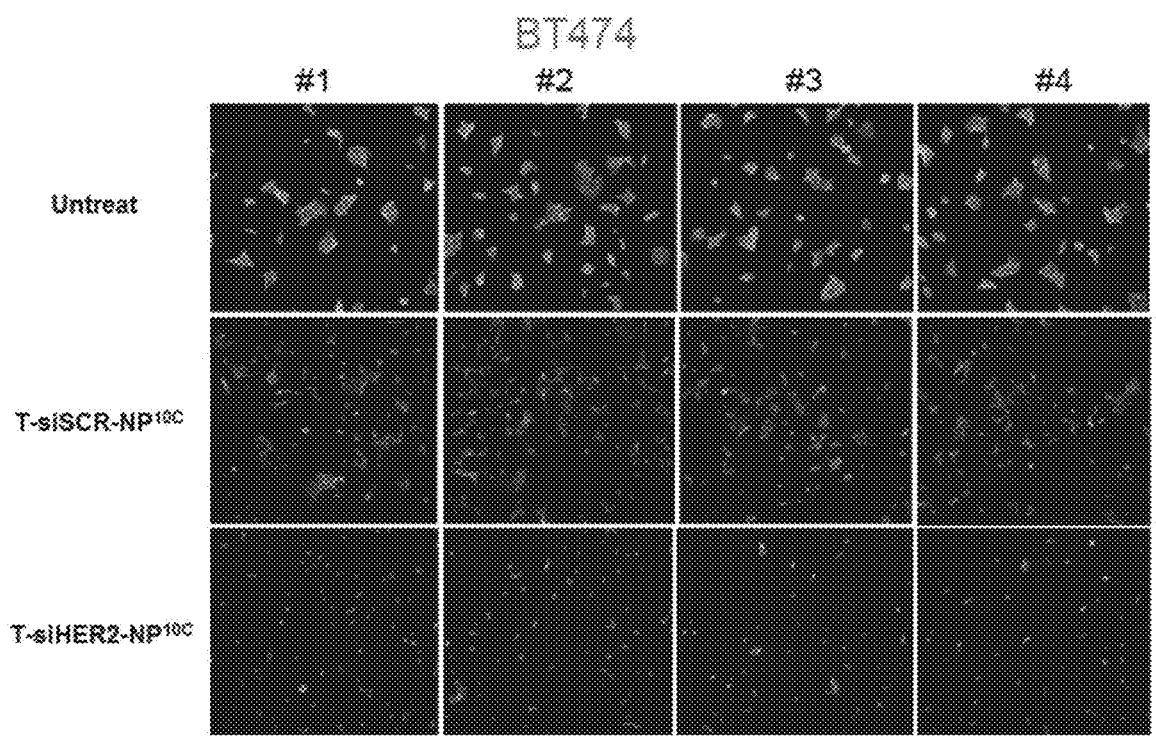
FIG. 11 shows reduced HER2 protein expression (by immunofluorescent staining) in BT474 upon treatment with T-siSCR-NP$^{10C}$ (due to trastuzumab) and T-siHER2-NP$^{10C}$ (due to siHER2 and trastuzumab). #1-4 represent replicates.

Treatment with T-siSCR-NP$^{10C}$ reduced HER2 levels and killed HER2+ breast cancer cells, indicating that the antibody (T) on the nanoconstruct not only serves as a cell targeting agent but also has therapeutic effect. FIG. 11, for example, shows that HER2 levels in BT474 were reduced by 41% with T-siSCR-NP$^{10C}$ (due to T effect) and by 87% with the T-siHER2-NP$^{10C}$ (due to T and siHER2 effect) compared to untreated controls. Likewise, FIG. 9D shows that cell viability was reduced 59% by T-siSCR-NP$^{10C}$ and 86% by T-siHER2-NP$^{10C}$.

Cell viability after treatment with T-siHER2-NP$^{10C}$ was also measured in a panel of HER2+ breast cancer cells, HER2− breast cells, and HER2− non-breast cells. FIG. 10 shows that treatment with T-siHER2-NP$^{10C}$ greatly reduced viability of HER2+ breast cancer cells (BT474, SKBR3, HCC1954 and JIMT-1), while having little impact on HER2− breast cells (MCF-7, MDA-MB-231, MDA-MB-468, MCF-10a), and HER2− non-breast cells (HepG2 and HEK-293). The cell killing effect was dependent on the HER2 protein levels of the cells (Inset of FIG. 10).

Figure 12A:
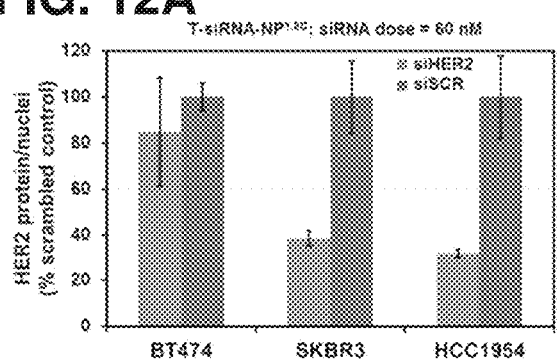
FIGS. 12A-12C show HER2 silencing efficacy of siHER2-nanoconstructs.
Figure 12B:
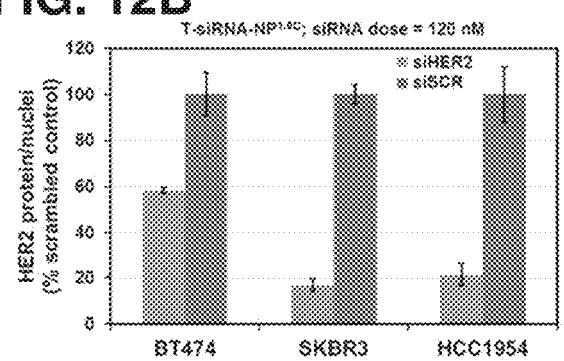

FIG. 9A shows that T-siHER2-NP$^{10C}$ was more effective than T-siHER2-NP$^{1.8C}$ (FIG. 12A) at equivalent siRNA dose. However, FIG. 12B shows that doubling the dose of T-siHER2-NP$^{1.8C}$ could reduce HER2 protein levels by 79-83% in SKBR3 and HCC1954.

Figure 12C:
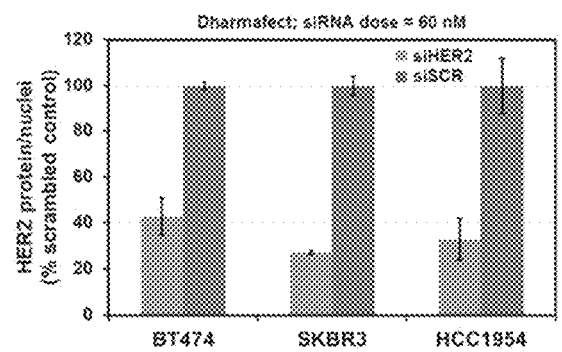

Overall, T-siHER2-NP$^{10C}$ demonstrated better HER2 knock-down and cancer cell killing efficacy than T-siHER2-NP$^{1.8C}$. Encouragingly, the T-siHER2-NP$^{10C}$ (FIG. 9A) outperformed commercially available DharmaFECT™ in all cell lines (FIG. 12C).

Example XIII

Overcoming Drug Resistant Cancer with siHER2

Figure 13A:
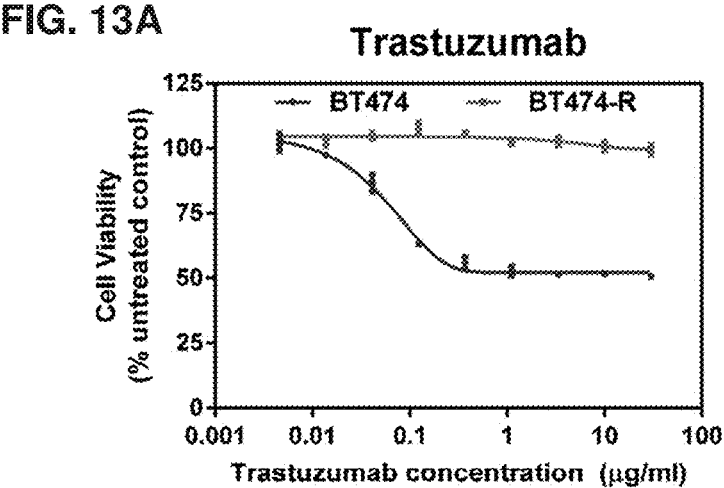
FIGS. 13A-13C show the effect of trastuzumab and siHER2-nanoconstructs on cell viability.
Figure 13B:
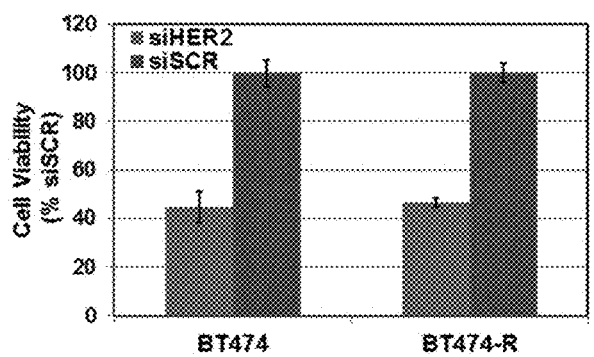
Figure 13C:
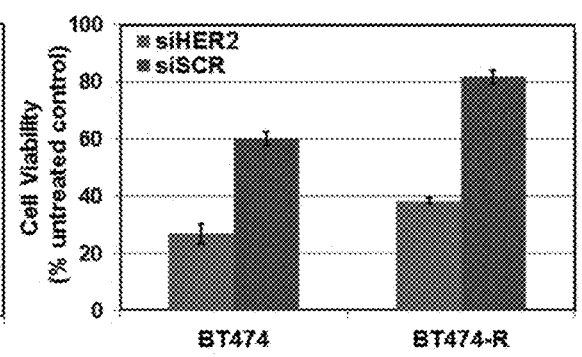

The efficacy of T-siHER2-NP$^{10C}$ in intrinsically trastuzumab-resistant HER2+ cell lines (HCC1954 and JIMT1), in a parental HER2+ cell line (BT474) that responds to trastuzumab and lapatinib, and in BT474-R, a derivative cell line that was made lapatinib-resistant by long-term treatment with 1 µM lapatinib was also assessed. FIG. 13A shows that the BT474-R cells were much less responsive to trastuzumab compared to parental BT474. However, FIG. 13B shows that both trastuzumab-sensitive and resistant cell lines responded similarly with respect to siHER2 action (see T-siHER2-NP$^{10C}$ vs. T-siSCR-NP$^{10C}$ control). This indicates that siHER2 on the nanoconstruct can overcome cancer resistance to trastuzumab. Meanwhile, FIG. 13C shows that BT474-R was less responsive to T-siSCR-NP$^{10C}$ than BT474, indicating that the BT474-R cells were indeed resistant to trastuzumab (on the nanoconstructs).

Example XIV

Blood Compatibility (Hemolysis, Coagulation, and Platelet Aggregation)

The T-siHER2-NP$^{1.8C}$ and T-siHER2-NP$^{10C}$ were assessed for hemolysis, thrombogenesis, and platelet aggregation, and the results were benchmarked with FDA-approved nanoparticle products: Abraxane (Paclitaxel-albumin nanoparticles) and Feraheme (iron oxide nanoparticles used as a MRI contrast agent). Nanoparticles were tested at 1× and 5× of the intended human blood level. Studies of blood compatibility were performed following or with minor modification from the Nanotechnology Characterization Laboratory's (Frederick, Md.) published protocols.

Hemolysis.

Figure 14A:
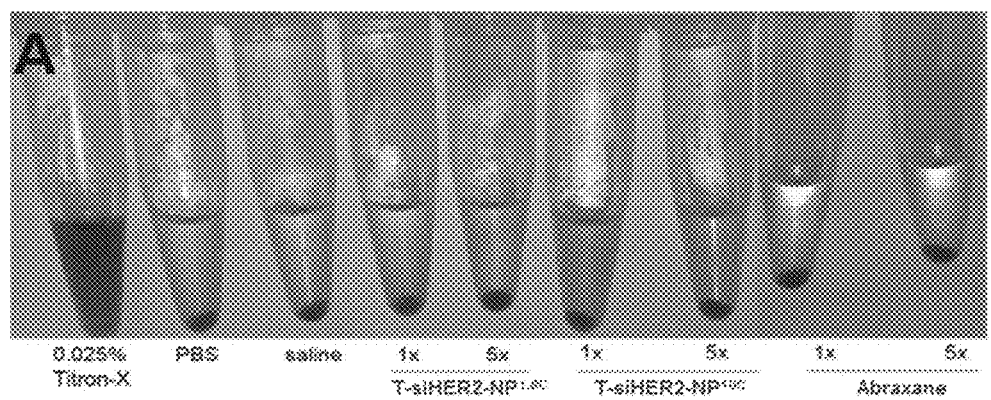

Human blood was collected in the presence of EDTA, and serum was removed. Red blood cells were suspended at 1×10$^9$ cells per mL and exposed to nanoparticle (final concentrations of 70 or 350 µg/mL for 1× or 5×, respectively) for 4 hours and 37° C. Following centrifugation, absorbance of hemoglobin in the supernatants (at 542 nm) was measured and used to quantify percent hemolysis. Abraxane (Celgene) at 94 µg/mL for 1× and 470 µg/mL for 5× was used. As shown in FIG. 14A, T-siHER2-NP$^{1.8C}$ and T-siHER2-NP$^{10C}$ did not cause hemolysis of red blood cells at either dose, while complete blood lysis was achieved with 0.025% Triton-X (the positive control).

Coagulation (Thrombogenesis) Assay.

Figure 14B:
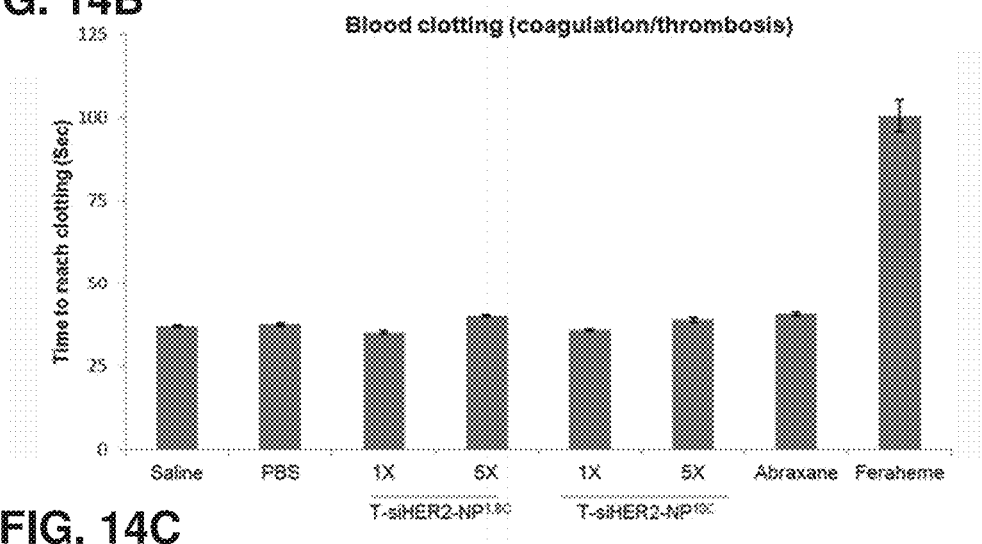
FIG. 14B is a graph showing no significant increase in clotting time over vehicle controls (saline and PBS) or FDA-approved nanoparticle-drug benchmarks (Abraxane or Feraheme).

Platelet-poor plasma (PPP) was obtained following a two-step centrifugation of isolated blood (diluted in 3.2% sodium citrate, 1:10). After the first spin at (2150 g, 10 min), the top portion of plasma (~75% of the total volume) was collected without disturbing the plasma at the bottom. The collected portion was centrifuged again at the same speed for 10 minutes, and the top portion (~75% of the total volume) was collected as PPP. Nanoconstructs were mixed with 0.15 mL PPP to the final concentration of 70 or 350 µg/mL. The tubes were incubated for 30 minutes at 37° C. After 30-minute incubation, 0.05 mL of APTT-xl reagent was added and incubated for 3 minutes in the Trinity Biotech KC-4 coagulation analyzer. After which, 8.3 mM CaCl$_2$ was added and the time until the onset of coagulation was recorded. Abraxane at 1× and 5× doses was used as a control. Likewise, Feraheme (AMAG Pharmaceuticals) at 102 µg/ml for 1× and 510 µg/ml for 5×, was also used in parallel. FIG. 14B shows that the nanoconstructs and Abraxane did not affect the coagulation time of platelet poor plasma since all took about 37 s. Only Feraheme prolonged the coagulation time, in agreement with known side effects related to abnormal clotting previously reported (M. H. Schwenk 2010).

Platelet Aggregation Assay.

Figure 14C:
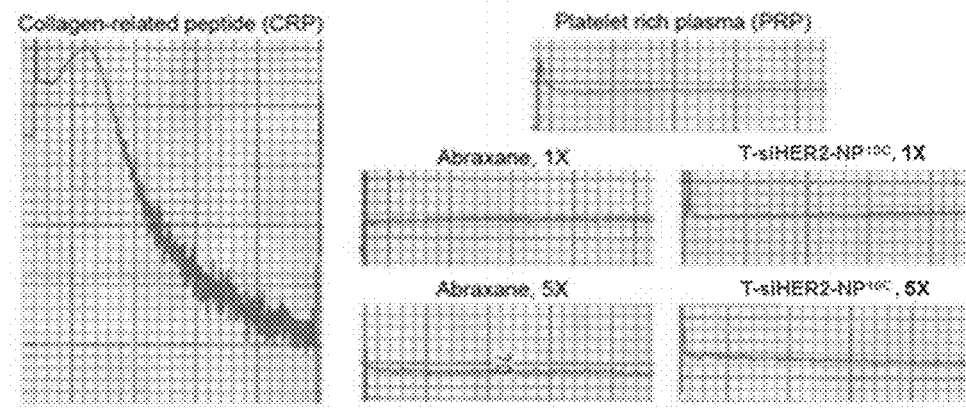
FIG. 14C is a graph showing no significant increase in platelet aggregation over vehicle controls (saline and PBS) or FDA-approved nanoparticle-drug benchmarks (Abraxane or Feraheme). 1× is anticipated human blood level, and 5× is 5-fold of that level.

Platelet-rich plasma (PRP) was obtained following centrifugation of isolated blood (diluted in 3.2% sodium citrate, 1:10). The isolated blood was centrifuged at 200 g for 20 minutes. The supernatant (which contains PRP) was collected and maintained at room temperature prior to treatment. Following a 1-min incubation at 37° C. (baseline), reactions were initiated by addition of nanoparticle (70 or 350 µg/mL) or collagen related peptide (CRP; 100 µg/ml) and monitored for three minutes for optical density via an aggregometer (Chrono-log Corp). Abraxane at 1× and 5× as entailed above was also used as a benchmark. FIG. 14C shows that the nanoparticles and Abraxane did not trigger platelet aggregation while a collagen related peptide used as a positive control triggered aggregation immediately.

Example XV

Immune Response—Peripheral Blood Mononuclear Cell (PBMC) Cytokine Release Assay

A PBMC cytokine release assay was conducted according to the recommendations and method by the Nanotechnology Characterization Lab (NCL) of NCI for immunological studies of nanoparticles. The in vitro cell based assay evaluated cytokine production by PBMCs (200,000 cells/well) following a 24-hour exposure to the test materials. Test materials included nanoconstructs with and without siHER2 to investigate the potential impact of siRNA mediated immune response. Following incubation, cell culture supernatants were collected and analyzed for IL-1β, IL-6, IFN-α, and TNF-α by a cytometry bead array (Milliplex Magnetic Bead) following the manufacturer's protocol. Abraxane and Feraheme were used as drug benchmarks since there is no siRNA based nanoconstruct drug in the market.

The effect of T-siHER2-NP$^{1.8C}$ and T-siHER2-NP$^{10C}$ on immune response was evaluated upon treating peripheral blood mononuclear cells (PBMCs) isolated from human blood with these nanoconstructs. PBMCs have been reported to respond to siRNA transfection with a sequence-specific TLR 7/8 dependent induction of IFN-α and TNF-α (R. Broering et al., 201; M. Zamanian-Daryoush, 2008). The TLR 7/8 agonist, R848, was used as a direct positive control since TLR7 and TLR8 are located within the endosomes (A. Chaturvedi, S. K. Pierce, 2009) where nanoconstructs and siRNA are expected to reside. FIGS. 15A-F show that neither T-siHER2-NP$^{1.8C}$ nor T-siHER2-NP$^{10C}$ increased the levels of IL-6 and TNF-α at either the 1× or 5× level, while Abraxane significantly increased both cytokines at the 5× level. Both nanoconstructs increased the levels of IFN-α and IL-1β somewhat, but not to the extent observed for Abraxane for IL-1β and Feraheme for IFN-α. The immune response was not significantly different for nanoconstructs with or without siRNA, suggesting that the response was not siRNA specific. Lastly, the PBMC immunological response to T-siHER2-NP$^{10C}$ was not significantly different than that to T-siHER2-NP$^{1.8C}$.

Example XVI

Endotoxin (LAL Gel-Clot) Assay of Nanoconstructs

To ensure sterility of our material production, T-siHER2-NP$^{1.8C}$ and T-siHER2-NP$^{10C}$ were tested for lipopolysaccharides or LPS (endotoxin), produced by gram-negative bacterial contamination. About 35% of clinically relevant nanoparticles have been found to carry this contaminant (R. M. Crist et al., 2013). The two nanoconstructs were tested along with Abraxane as an FDA drug benchmark. All were negative for endotoxin (FIGS. 15E and F). This suggests an advantage of layer-by-layer modification, as sequential washing steps promote sterilization of the resulting product.

Example XVII

Mouse Tumor Models and In Vivo Efficacy Studies

In vivo gene silencing studies were performed in orthotopic mouse tumor models; 4×10$^6$ HCC1954 cells (unless specified otherwise) were implanted into the mammary fat pads of 5-week-old SCID mice (Charles River, Wilmington, Mass.) and allowed to grow to an average size of about 250 mm$^3$. Mice were then grouped and proceeded to receive a single injection (tail vein) of the nanoconstructs (T-siHER2-NP$^{10C}$ or T-siSCR-NP$^{10C}$, 1.25 mg/kg siRNA), or the PBS control. The tumors were harvested four days after treatment and analyzed for HER2 protein expression by immunofluorescence as shown in FIG. 16A and quantified in FIG. 16B. FIG. 16B shows that the HER2 protein levels in the HCC1954 tumors were reduced by 59% compared to saline control (p<0.0013) and by 47% compared to treatment with the T-siSCR-NP$^{10C}$ control (p<0.015). It should be noted that 23% (p=0.27 vs. saline control) of the HER2 reduction in the siSCR control is likely due to trastuzumab on the nanoconstructs.

Figure 17A:
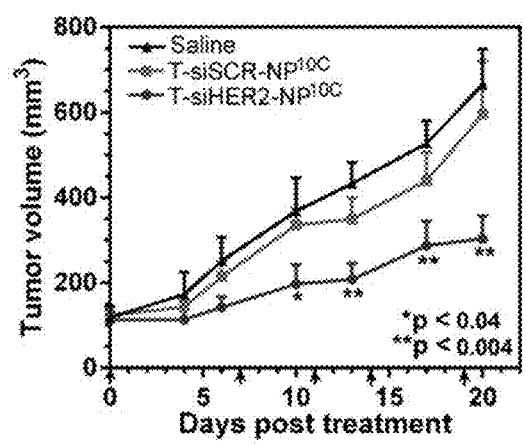
FIGS. 17A-17D are a series of graphs showing tumor growth in mice bearing tumor xenografts following nanoconstruct treatment.
Figure 17B:
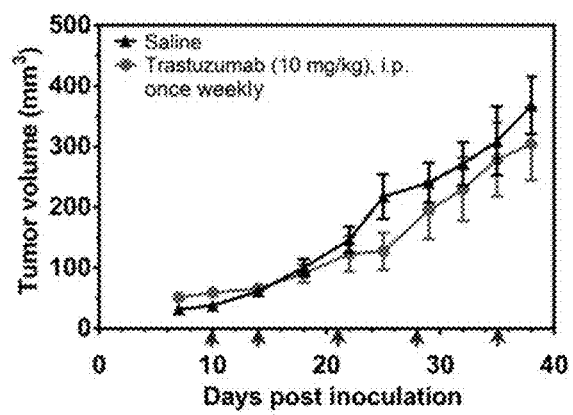
Figure 17C:
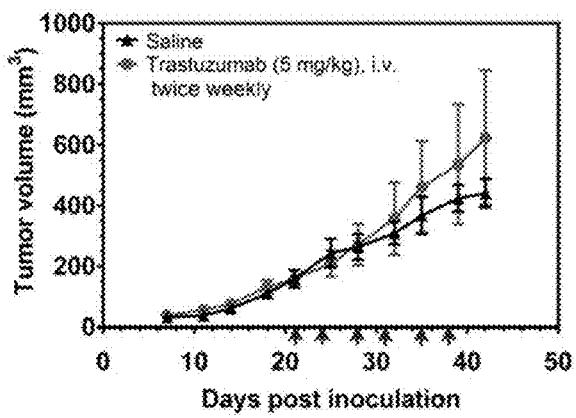
Figure 17D:
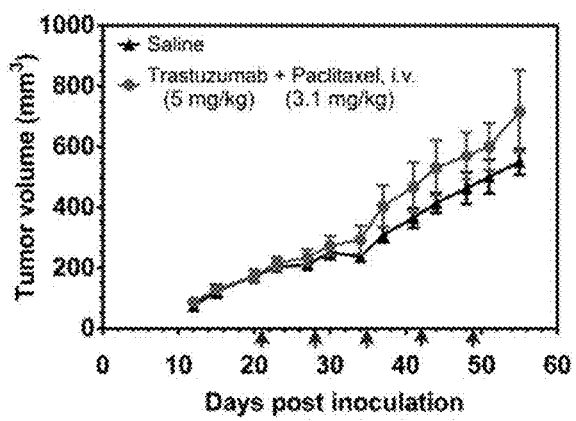

FIG. 17A shows that 5 intravenous tail vein injections of T-siHER2-NP$^{10C}$ (1.25 mg siHER2/kg), over a period of three weeks significantly inhibited tumor growth, while T-siSCR-NP$^{10C}$ produced little effect. This response is noteworthy since HCC1954 has been established as resistant to cisplatin (I. Beyer et al., 2012), trastuzumab (I. Beyer et al., 2012), and pertuzumab (F. Henjes, et al., 2012) in vitro and/or in mice. HCC1954 resistance in vivo to trastuzumab and a trastuzumab/paclitaxel combination was confirmed in our lab in FIGS. 17B-D.

Figure 18:
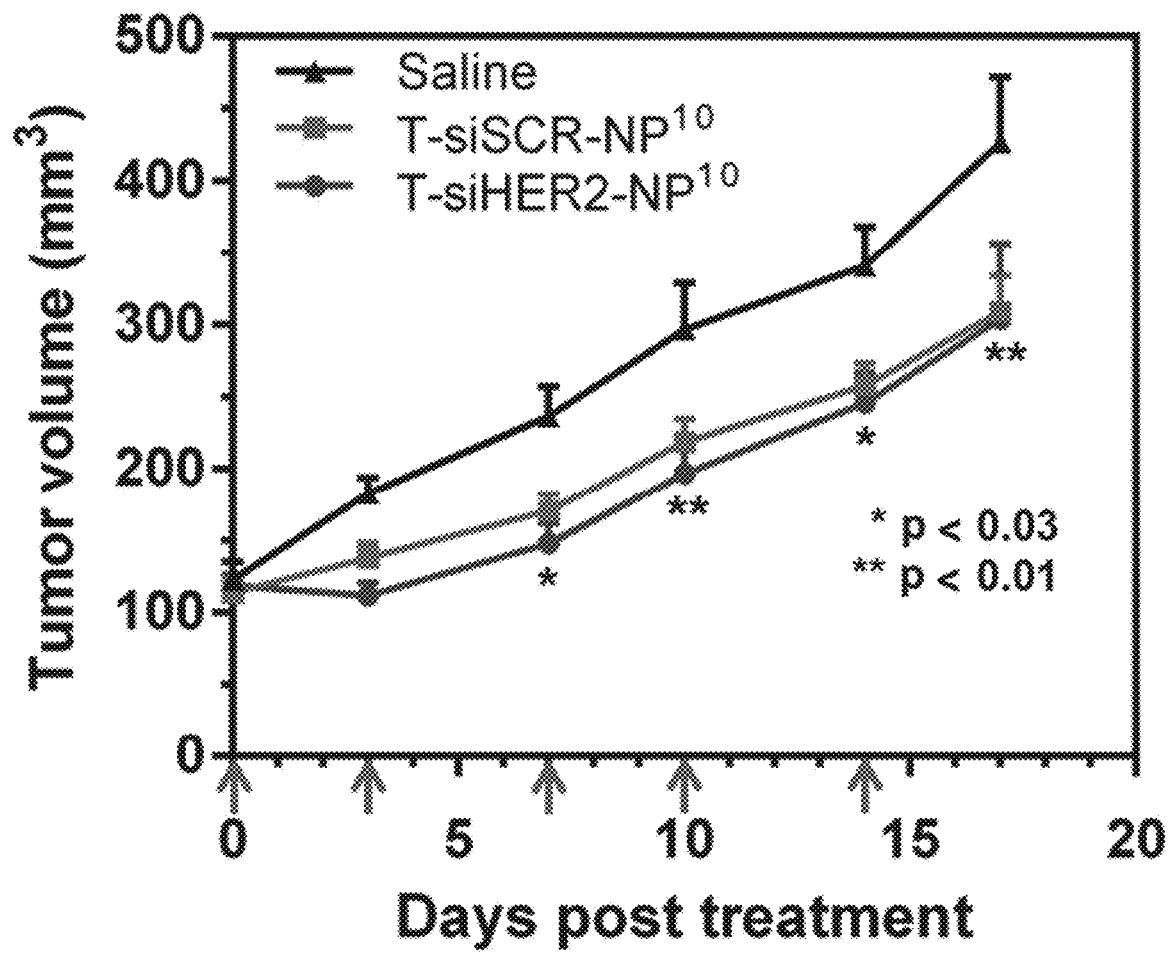
FIG. 18 is a graph showing tumor growth in mice bearing orthotopic HCC1954 tumor xenografts (n=11/group) post i.v. injection with multiple doses of T-NP$^{10}$ (O-87 core, not cross-linked) loaded with siHER2 or siSCR (2.5 mg/kg siRNA, NP/siRNA of 50) or PBS control at the time points indicated by the arrows.

T-siHER2-NP$^{10C}$ (S-47 core, about 100 nm in size, FIG. 17A) showed better tumor growth inhibition efficacy than the non-cross-linked larger particles (T-siRNA-NP$^{10C}$, with O-87 core, about 200 nm in size, FIG. 18) on the same HCC1954 tumor model (n=11/group) even at half the dose of siRNA (i.e., 1.25 mg/kg in FIG. 17A vs. 2.5 mg/kg in FIG. 18).

The nanoconstructs without trastuzumab (siHER2-NP$^{10C}$) also inhibit tumor growth in the HCC1954 tumor model as shown in FIG. 19. Tumor mice were treated with siHER2-NP (n=8), T-siSCR-NP (n=7), or saline control (n=5) at the siHER2 or siSCR dose of 1.25 mg/kg and NP/siRNA ratio of 50 on days specified with arrows. This is owed to the passive delivery, relying on enhanced permeability and retention (EPR) effect of the tumors for the nanoconstructs, followed by the uptake of positively charged nanoconstructs to cancer cells, yielding tumor growth inhibition effect.

In another example, BT474-TRgf (BT474 variant developed to be resistant to trastuzumab by serial passaging the cells in mice, Francia et al., 2012) was used to evaluate the efficacy of T-siHER2-NP. While the BT474-TRgf cells were resistant to trastuzumab in vitro (FIG. 20A) and in a tumor mouse model (FIG. 20B), they responded to T-siHER2-NP treatment in the tumor model (FIG. 20B). siHER2 dose was 1.25-2.5 mg/siRNA and 5 animals per treatment group.

Example XVIII

Lyophilization of Nanoconstructs for Long Term Storage

Nanoconstruct suspensions (T-NP or NP) in 0.1 M Tris HCl (pH 7.4) were added to a solution of trehalose to achieve a final concentration of 10 mg/mL MSNP and 0-25 weight % of trehalose per nanoparticle. The well-mixed suspension was frozen slowly from room temperature to −55° C. in a freeze dryer. This was followed by primary and secondary drying. Primary drying (−40° C., 100 µBar, 24 hr) was to sublimate the ice crystals formed during the freezing step. Secondary drying (20° C., 20 µBar, 12 hr) was to eliminate bound water molecules on the nanoconstruct surface. The finished products were in the form of powder in sealed and storable bottles.

Figure 22A:
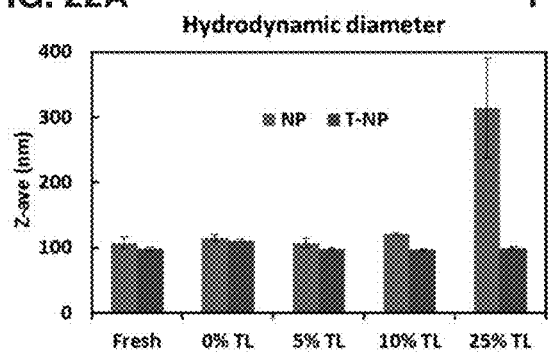
FIGS. 22A-22D show the size, zeta potential, luciferase silencing efficacy and cell viability effects of lyophilized and freshly prepared nanoconstructs.
Figure 22B:
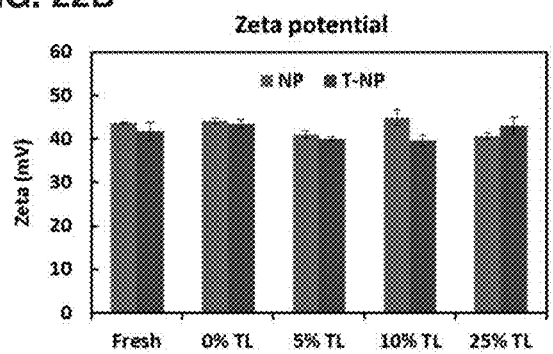
Figure 22C:
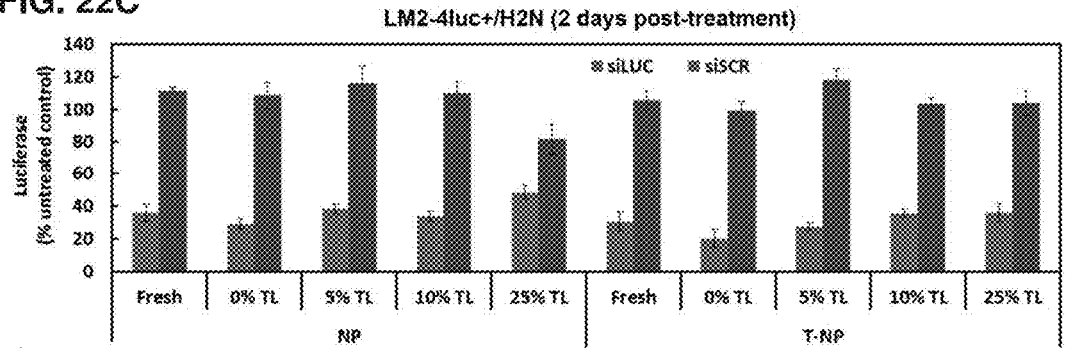
Figure 22D:
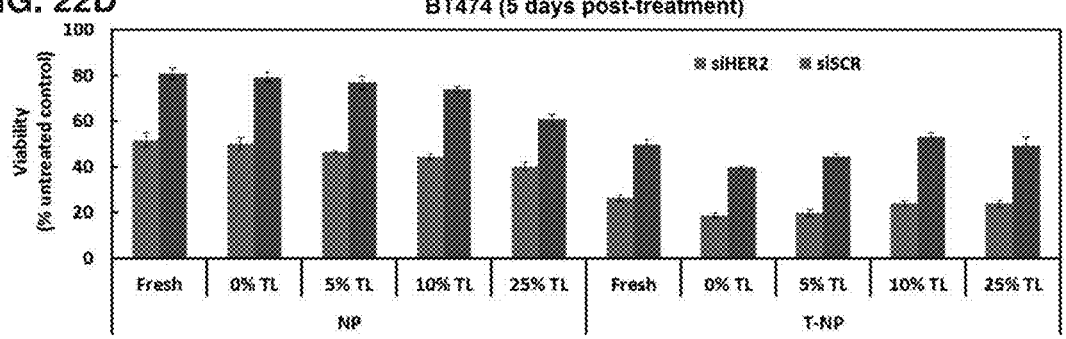
Figure 23A:
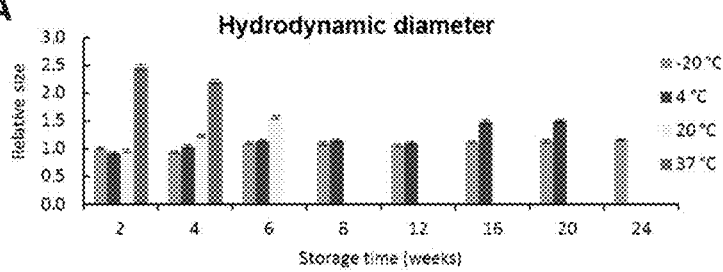
FIGS. 23A-23E show the size, zeta potential, siRNA loading properties, luciferase silencing efficacy, and cancer cell-killing properties of lyophilized trastuzumab-conjugated nanoconstructs (T-NP) stored at various temperatures and time relative to those of freshly prepared nanoconstructs from the same batch.
Figure 23B:
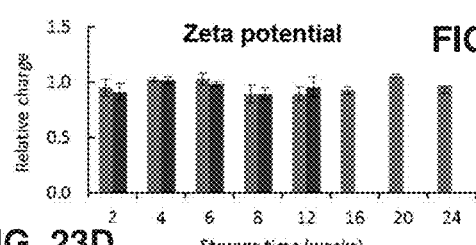
Figure 23C:
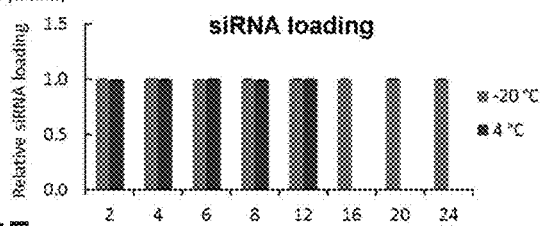
Figure 23D:
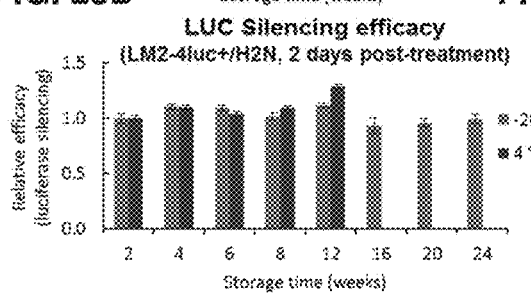
Figure 23E:
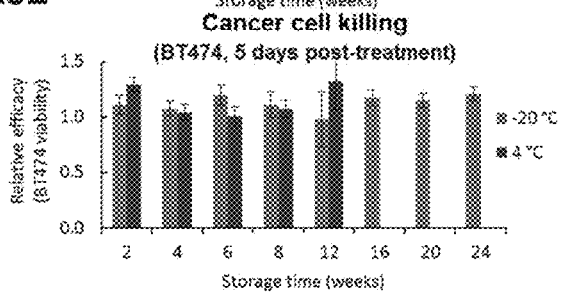

All lyophilized nanoconstructs with trehalose content of 0-10% retained the average size and charge of the freshly made nanoconstruct after 1 min of sonication as shown in FIG. 22A-B, respectively. However, the 0% trehalose conditions yielded larger size distribution (not shown). After binding with either siLUC or siHER2, lyophilized materials still yielded very comparable performance with freshly made material counterparts (from the same batch) in terms of luciferase silencing ability (FIG. 22A, with siLUC) and cell viability of BT474 cells (FIG. 4B, with siHER2). Some exceptions are also evident in FIG. 22D. The 0% trehalose conditions yielded T-NP that was more toxic to cells than freshly made material. Hence, based on the size distribution and efficacy, the 5% trehalose, the lowest additive that yielded the same efficacy as the freshly made counterpart, was selected for future lyophilization processes and long term storage evaluation.

Further, T-NP lyophilized with 5% trehalose and stored at −20° C. to 37° C. were monitored for their properties over a 24-week storage time. FIGS. 23A-23E shows that when stored at −20° C., T-NP maintained (A) hydrodynamic size, (B) zeta potential, (C) siRNA loading, (D) luciferase silencing efficacy, and (E) cancer cell killing efficacy similar to freshly made nanoparticles (Fresh) from the same batch. Data indicates that −20° C. is the best storage temperature for preserving all properties of the fresh material for at least 24 weeks (6 months). Similar outcomes were achieved with NP without T.

Example XIX

Reproducibility and Scalability of Nanoconstruct Production

Many nanoparticle platforms are known to have problems with batch-to-batch reproducibility—especially at a larger scale. MSNP core production via sol-gel chemistry and layer-by-layer surface modification affords very reproducible and scale-able production of the nanoconstruct. Multiple individual batches of mesoporous silica nanoparticles were created to determine reproducibility of nanoparticle synthesis. As shown in Table 6, the size, charge, and silencing efficacy were closely correlated with 2.4% relative standard deviation (RSD) of particle sizes from 6 batches, indicating that the material synthesis is highly reproducible. Scaling-up from 300 mg/batch to 6 g/batch has been accomplished (e.g., by simply increasing the reaction solution from 125 mL to 2.5 L during nanoparticle synthesis), which yielded similar material properties with the smaller batches.

TABLE 6

Reproducibility of nanoconstruct synthesis before and after surface modification.

| | MSNP core | T-NP$^{10C}$ | | |
|---|---|---|---|---|
| Batch | Hydrodynamic Size Z-average ± SD (nm) | Hydrodynamic size Z-average ± SD (nm) | Zeta Potential Average ± SD (mV) | % Luc silencing efficacy (vs. siSCR) |
| 1 | 61.1 ± 0.7 | 115.8 ± 4.0 | 25.0 ± 0.1 | 75.7 ± 4.0% |
| 2 | 58.1 ± 0.6 | 117.4 ± 0.5 | 24.9 ± 0.1 | 80.5 ± 2.8% |
| 3 | 59.7 ± 0.5 | 114.5 ± 7.1 | 25.0 ± 0.1 | 76.1 ± 2.4% |
| 4 | 57.7 ± 0.9 | 123.8 ± 3.3 | 25.0 ± 0.1 | 76.6 ± 3.9% |
| 5 | 60.8 ± 0.8 | 113.2 ± 2.3 | 25.0 ± 0.1 | 76.2 ± 2.8% |
| 6 | 58.8 ± 0.3 | 115.6 ± 1.3 | 25.0 ± 0.1 | 77.0 ± 2.2% |
| Average | 59.4 | 116.7 | 25.0 | 77.0 |
| % Relative SD | 2.4 | 3.2 | 0.2 | 2.3 |

Example XX

Additional siRNA Targeting Genes Beyond HER2 for Treating Cancer

The initial screen sought to assess the efficacy of individual siRNAs in HER2+ breast cancer. SiRNA against AKT (isoforms 1, 2, 3), BCL2, PLK1, GRB7, and EPS8L1, all were benchmarked against the previously optimized siHER2 sequence. Four cell lines were chosen, representing trastuzumab-resistant (HCC1569, HCC1954, JIMT1) and sensitive (BT474) HER2+ breast cancer. For each gene, the siRNA sequences were also varied (Hs_AKT1_5 FlexiTube siRNA (S1002991450), Hs_AKT1_8 FlexiTube siRNA (S100287742), Hs_AKT1_10 FlexiTube siRNA (S102757244) and Hs_AKT1_11 FlexiTube siRNA (S102758406) for AKT1 shown to be efficacious by Qiagen) (Qiagen, Valencia, Calif., USA) as possible. Representative data for BT474 is shown in FIG. 24A.

We also evaluated dual targeting siRNA against AKT1/BCL2 (e.g., one siRNA duplex has one strand targeting AKT1 and the other strand targeting BCL2) (Table 1). FIGS. 24A-24B confirm the cell killing efficacy (A) and protein knockdown activity (B) of the dual-targeting siRNA.

In the four cell lines tested, none of the individual AKT1 or BCL2 siRNAs worked better than the siAKT1/BCL2 (dual-targeting siRNA) or siPLK1. Therefore, the three siRNAs selected from the initial screening are siHER2, siAKT1/BCL2, and siPLK1. FIG. 25 shows the cell viability 4 days post-exposure to the siRNAs at the indicated dose range (0.01-30 nM). The siRNA targeting PLK1 proved to be the most potent of all siRNAs in each respective cell line; the IC$_{50}$ (dose inhibiting 50% growth) of siPLK1 is about 0.2 nM for 3 out of 4 cell lines studied.

Figure 27B:
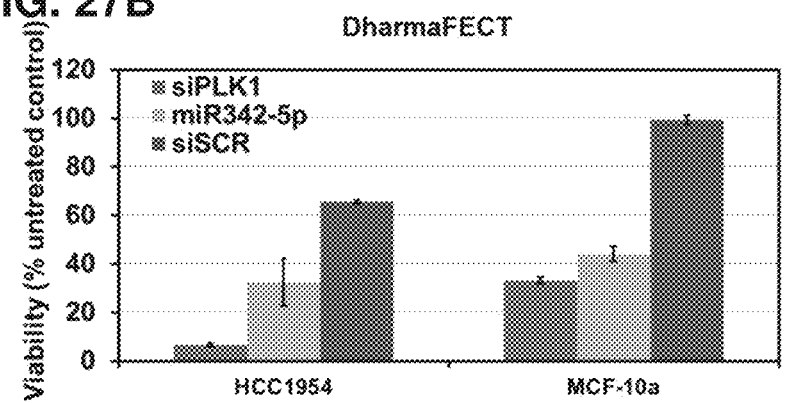

The cell panel was expanded to include triple negative breast cancer, ER+, and non-breast cells. As shown in FIG. 26, siPLK1 is still the most potent among the three siRNAs evaluated. (FIG. 26). However, siPLK1 was toxic to non-target cells (e.g., non-targeted cells in FIG. 26) when delivered with commercial DharmaFECT™. Treatment specificity may be achieved for breast cancer cells (HCC1954) over normal breast epithelial cells (MCF-10A) when the siPLK1 is delivered with the nanoconstructs (T-NP), compared to DharmaFECT™, as shown in FIGS. 27 A and B, respectively.

FIG. 27A also shows the ability of T-NP in delivering miRNA mimics (miR342-5p, obtained from GE Dharmacon (Lafayette, Colo., USA) and eliciting killing of cancer cells but not MCF-10A.

Example XXI

Screening of siRNA in Combination with Paclitaxel

Cells were first treated with 30 nM siRNAs (and commercial DharmaFECT™) followed by 5 nM paclitaxel treatment 24 hours later. Cell viability was determined 3 days later. As shown in Table 7, the combination of siRNA with paclitaxel enhanced the overall reduction in cell viability compared to paclitaxel alone (Scramble+Paclitaxel, top row). The % enhancement by various siRNAs with paclitaxel over paclitaxel alone was also summarized in Table 7. In short, knocking down HER2 had the greatest impact on paclitaxel toxicity in BT474 (having highest HER2 level). For other cells, the best efficacy was achieved with paclitaxel+siPLK1. The effect of paclitaxel combined with siAKT1/BCL2 or siEPS8L1 was also significant. The best enhancement by siAKT1/BCL2 (38-41%) appeared to be with basal cells, HCC1954, BT549, and HCC70. EPS8L1 is involved in EGFR signaling and functions in cell migration. As a result, efficacy of EPS8L1 was not restricted to HER2+ cells and proved effective in the two triple negative cell lines tested (both having high EGFR).

TABLE 7

Screening of siRNA targeting HER2, PLK1, AKT1/BCL2 and EPS8L1 in combination with the chemotherapeutic drug paclitaxel.

| | | Cell Viability (% of Scramble Control) | | | | |
|---|---|---|---|---|---|---|
| Treatments | | HER2 Positive | | | Triple Negative | |
| siRNA | | Luminal | | | Basal | |
| Targets | Paclitaxel | BT474 | SKBR3 | HCC1954 | BT549 | HCC70 |
| Scramble | + | 58% | 39% | 55% | 59% | 70% |
| HER2 | − | 35% | 51% | 68% | 51% | 76% |
| | + | 26% | 33% | 49% | 40% | 49% |
| Enhanced Paclitaxel effect due to gene knockdown | | 32% | 6% | 6% | 19% | 21% |
| AKT1+BCL2 | − | 74% | 77% | 47% | 54% | 42% |
| | + | 39% | 29% | 17% | 23% | 29% |
| Enhanced Paclitaxel effect due to gene knockdown | | 19% | 10% | 38% | 36% | 41% |
| PLK1 | − | 33% | 14% | 6% | 15% | 33% |
| | + | 33% | 13% | 5% | 13% | 27% |
| Enhanced Paclitaxel effect due to gene knockdown | | 25% | 26% | 50% | 46% | 43% |
| EPS8L1 | − | 37% | 53% | 57% | 40% | 65% |
| | + | 27% | 29% | 35% | 13% | 35% |
| Enhanced Paclitaxel effect due to gene knockdown | | 31% | 10% | 20% | 46% | 35% |

Example XXII

Delivery of Other Cargos by Nanoconstructs

Peptide Delivery.

FIG. 28A shows the ability of nanoparticles to load and deliver small peptides into cells. MSNP-PEI-PEG (non-cross-linked PEI) was loaded with GALA peptide (MW of 3 kDa) by electrostatic interaction in the same manner as siRNA. GALA was mixed with siRNA-nanoconstructs (13-130 nM GALA and 10 mg/L nanoconstructs) for 20 minutes in PBS (room temp, 300 rpm shaking). GALA clearly enhanced silencing efficacy of the nanoconstructs, owing to its ability as a pore-forming peptide to enhance endosomal escape of the siRNA-nanoconstructs (Li et al., 2004).

Co-Delivery of Antibody, siRNA, and Chemotherapeutic.

The nanoconstructs (MSNP-PEI-PEG or NP) can also co-deliver antibody, siRNA, and chemotherapeutic drugs to cancer cells. FIG. 28B shows the effects of trastuzumab (T), siHER2, and/or paclitaxel (PTX) loaded on the nanoconstruct in JIMT-1 cells. The combination of paclitaxel and trastuzumab on the same nanoparticle was very potent, which masked the effect of siHER2. Loading of PTX was accomplished by mixing 3 mg of PTX to ethanol solution containing 10 mg MSNP-PEI during the cross-linking step described in Example III. Doxorubicin (DOX) loading was performed by mixing 3 mg of DOX with 10 mg of MSNP in water overnight. MSNP-Dox was then centrifuged down and resuspended in ethanol for subsequent loading of PEI, PEG, and trastuzumab as outlined in Example III-V. In order to confirm that drug-loaded T-NP can still deliver siRNA and elicit gene knockdown effectively. Drug-loaded NP (paclitaxel (PTX) or doxorubicin (DOX)) with or without trastuzumab were evaluated for ability to deliver siLUC and elicit luciferase gene knockdown. FIG. 29 shows that the drugs did not negatively impact the gene knock-down efficacy of the materials. In addition, the combination of paclitaxel, trastuzumab, and siHER2 shows greater efficacy in inhibiting tumor growth in vivo than the free trastuzumab and paclitaxel combination as shown in FIG. 30.

Example XXIII

Antioxidant and/or Copper Chelating Nanoconstruct for siRNA Delivery

Figure 31A:
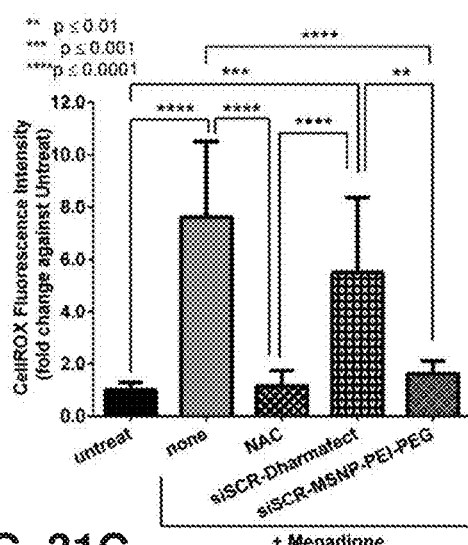
FIGS. 31A-31D.
Figure 31B:
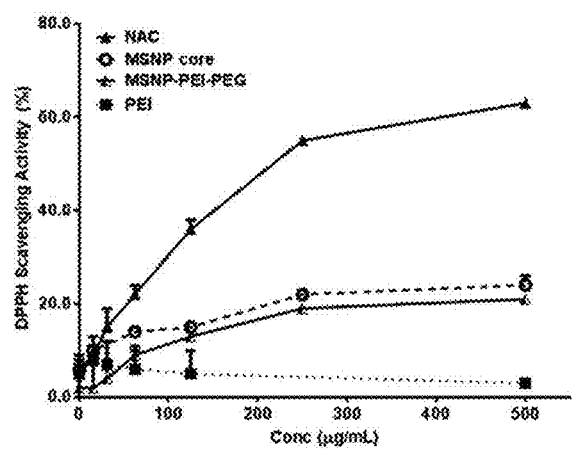
Figure 31C:
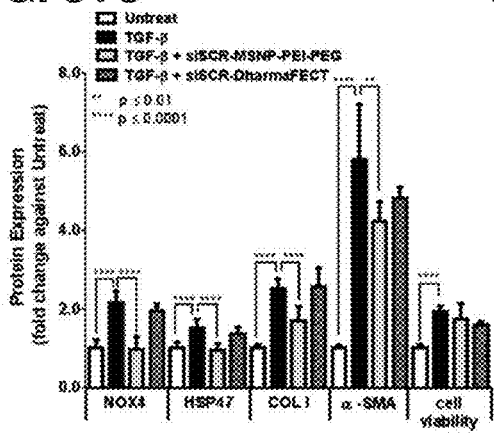
Figure 31D:
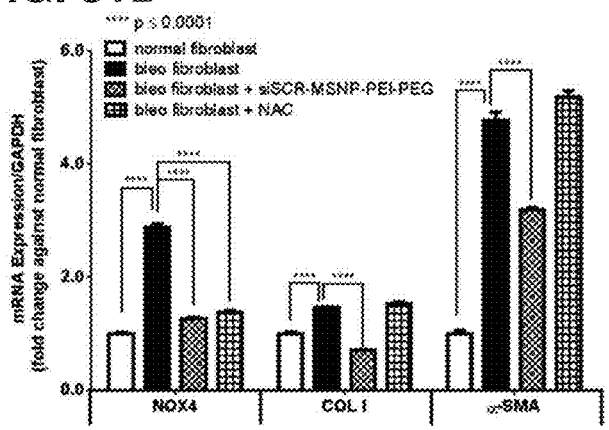
Figure 33A:
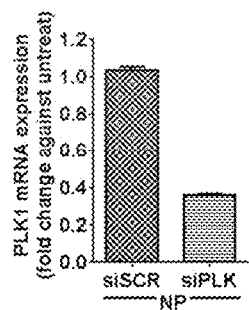
FIGS. 33A-33D are graphs showing the cellular effects of siPLK1-NP treatment.
Figure 33B:
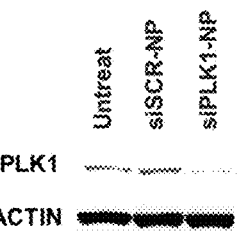
Figure 33C:
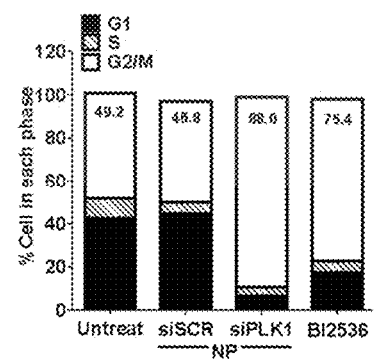
Figure 33D:
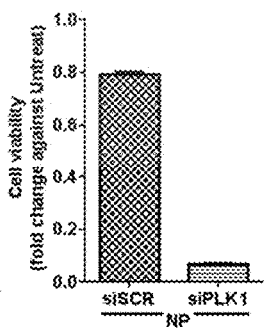

Another advantage of the MSNP based nanoconstruct is that the MSNP can reduce reactive oxygen species (ROS) in cells triggered by menadione as shown in FIG. 31A. The ROS reduction was attributed to the MSNP core and not the cationic PEI-PEG coating. This was confirmed by the finding (in a cell-free system) in FIG. 31B that bare MSNP core displayed higher DPPH free radical scavenging ability than the MSNP coated with PEI-PEG layer. FIG. 31B also shows that free PEI had no ROS scavenging ability. Note that DPPH is a stable free radical that is typically used to assess the ROS scavenging ability of antioxidants. Due to the antioxidant properties, the MSNP-PEI-PEG could reduce the effects of pro-inflammatory cytokine TGF-beta by inhibiting NOX4, HSP47, COL I, and alpha-SMA as shown in FIG. 31C. Likewise, FIG. 31D shows that the nanoconstruct could reduce the pro-fibrotic markers such as HSP47, COL I, and/or alpha-SMA, triggered by bleomycin. Bleo fibroblast denotes murine dermal fibroblasts harvested from bleomycin-induced scleroderma mouse model. Thus, the nanoconstruct has the potential to treat fibrosis as was confirmed in a fibrotic mouse model created by bleomycin treatment of mouse skin as shown in FIGS. 32A-32G (Morry et al., 2015). Treatment schedule is outlined in FIG. 32A. Reduction in skin fibrogenesis was observed with siSCR-nanoconstruct treatment but was enhanced with the siHSP47-nanoconstruct. This was evidenced by the reduction in skin thickness (FIGS. 32B-C), HSP47 (D), NOX4 (E), alpha-SMA (F), and COL I(G) compared to bleomycin treated mice.

In addition, NOX4 was found to be overexpressed in the majority of breast cancer cell lines, primary breast tumors, and ovarian tumors. The overexpression of NOX4 in normal breast epithelial cells could result in cellular senescence, resistance to programmed cell death, and tumorigenic transformation of the cells (K. A. Graham, 2010), establishing therapeutic utility of the MSNP carrier as a NOX reducer in addition to the therapeutic agents it delivers.

Antioxidant properties of nanoparticles coupled with siPLK1 can elicit treatment effects in breast cancer metastasis. FIGS. 33A-33D show in vitro PLK1 knockdown (A-B), G2/M cell cycle arrest (C), and cancer cell killing (D) induced by siPLK1-NP. FIGS. 34A-34H show that the antioxidant property of nanoparticles can scavenge ROS in cancer cells (A) without toxicity effect (B), resulting in decreased NOX expression (C), decreased cancer cell migration (in wound healing assay) (D-E), and decreased invasion of cancer cells (F-H) that was more effective than an established antioxidant NAC at 2-10 mM (H). The T-siSCR-NP nanoconstruct also limited tumor spread in vivo as shown in FIG. 35B as cancer cells were found primarily in the primary established site of this model (lung), compared to untreated mice where tumor signals can be found in other distant organs similar to metastasis sites of human breast cancer. When combined with siPLK1, T-siPLK1-NP resulted in tumor growth inhibition in lungs (FIGS. 35B-D, F and H) and subsequent prolonged survival in mice beyond T-siSCR-NP treatment (G). PLK1 knock down in the tumors was also observed (FIG. 35E).

Figure 36:
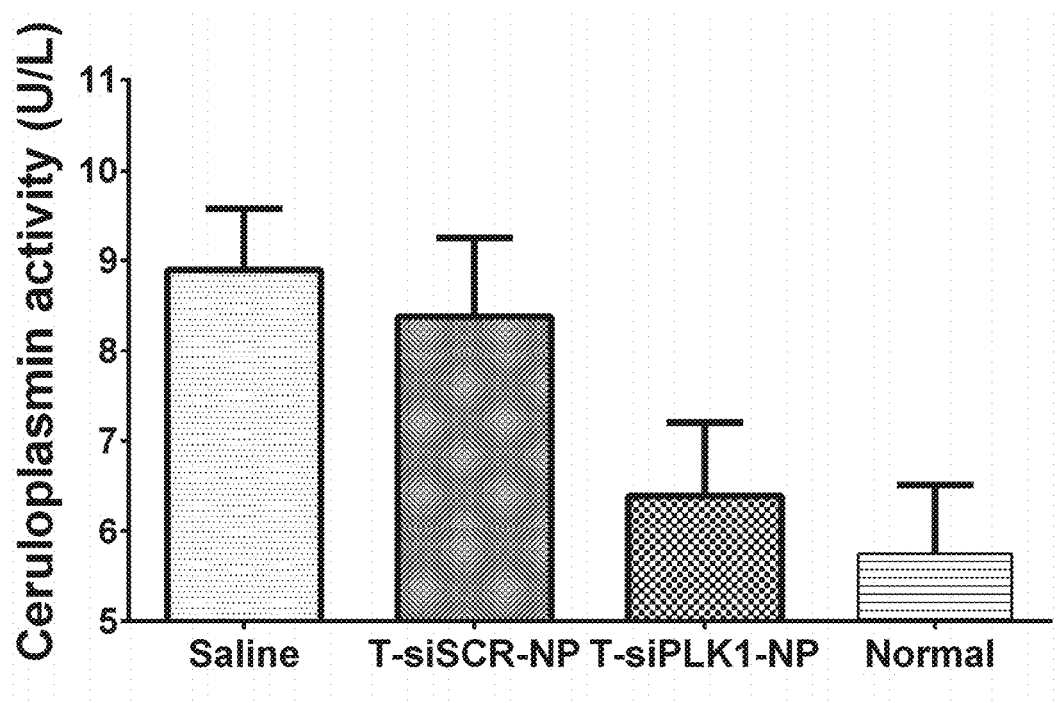
FIG. 36 shows ceruloplasmin activity (a biomarker of bioavailable copper) of the serum from the short-term study in FIGS. 35A-35H (n=5/group, serum collected at sacrifice). "Saline" represent to tumor mice with saline treatment; "Normal" represent normal mice without tumors.

Amine groups, e.g., from PEI on nanoconstructs, are known to be highly effective chelators of copper, which is a cofactor for angiogenesis and hence metastasis in cancer (Brewer et al., 2000). In agreement with our data, the lowest cancer metastasis and tumor burden was achieved with T-siPLK1-NP (FIG. 35, short term study), which agreed with the lowest serum ceruloplasmin (a biomarker for total body copper status) in corresponding mice (FIG. 36).

Example XXIV

Lanthanide and Fluorescent Dye Loading on MSNPs

MSNPs containing phosphonate groups were prepared by adding 3-trihydroxysilylpropyl methylphosphonate in situ during the MSNP synthesis described in Example I and Example II. Specifically, 500 mg of CTAB was dissolved in 240 ml of water (adjusted by 2 M NaOH). After temperature stabilized at 80° C., 2.5 mL of TEOS was added in to solution under stirring condition. After 15 minutes, 635 µL of 3-(trihydroxylsilyl) propyl methyl phosphonate was added. The reaction continued for 2 hours, and the pellets were recovered from suspension by centrifugation, washed with a copious amount of ethanol, and dried overnight. The particles were then resuspended and refluxed in acidic methanol (0.6 M HCl in methanol) overnight to remove CTAB. The resulting phosphonate-MSNPs were then washed with ethanol and dried in a desiccator overnight.

For lanthanide loading, 5 mg/ml of MSNP was suspended in water. Then 0.01-100 mg/L lanthanides were mixed with the MSNP suspension. The mixture was shaken for two hours. The material was then washed with a copious amount of water, and the material was dried. MSNP can undergo surface modifications (e.g., PEI, PEG, antibody loading as aforementioned) and can be used as a fluorescent probe or a probe for mass spectrometry.

For characterization, MSNP of known dry weight was mixed with 10 M $HNO_3$ for acid leaching of lanthanides. The leachate was then subjected to a lanthanide assay with ICP-MS. The amount of each lanthanide loaded on nanoparticle (as wt. %) is shown in FIG. 37A. FIG. 37B shows that the nanoconstruct can also be loaded with fluorescent dyes (on PEI layer) and/or an antibody (such as an anti-HER2 antibody), that recognizes HER2 proteins on the target cells.

Example XXV

Nanoconstructs Made from Other Inorganic Cores (e.g., Iron Oxide NPs)

As an alternative to silica, iron oxide ($Fe_3O_4$) nanoparticles (ION) can be used. Surface modification of such nanoparticles can be performed using similar methods to those described for MSNP. For example, a particle called DMSA-ION can be prepared. Specifically, ION were prepared by high temperature reaction of tris(acetylacetonato) iron(III) in the present of stabilizing surfactants—1,2-hexadecanediol, lauric acid and lauryl amine—in benzyl ether. The adduct was purified with ethanol and hexane to obtain precursor ION-lauric acid. The precursor nanoparticles then underwent a ligand exchange reaction from hydrophobic lauric acid to hydrophilic meso-2,3-dimercaptosuccinic acid (DMSA) which renders the nanoparticles water-soluble. The final DMSA-ION were magnetically purified with water, ethanol and acetone. ION of <10 nm by TEM has been achieved (Yantasee et al, 2007).

At neutral pH, DMSA has a negative charge which allows the ligand to electrostatically bind to positively-charged polyethylenimine (PEI). PEI modification allows the nanoparticles to bind with negative charged siRNA. Under low pH environment of intracellular compartment, DMSA is protonated and release the bound PEI which in turn releases the siRNA. Evaluation of ION based nanoconstruct for delivery of antibody, siRNA, chemotherapeutic, and/or dyes will be performed similar to MSNP nanoconstruct. Their advantages are small size for easy tumor accumulation, biocompatible, and MRI compatible.

Figure 38A:
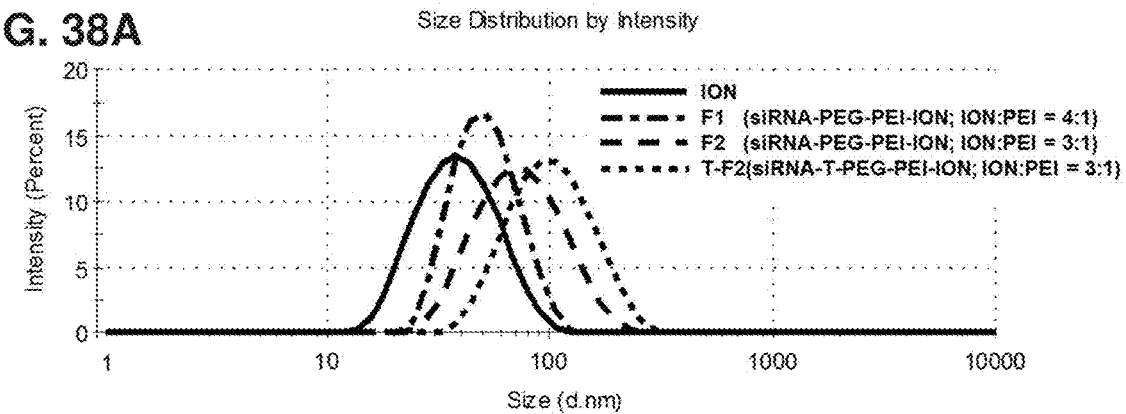
FIGS. 38A-38C show the size, luciferase silencing efficacy, and T2 relaxivity of iron oxide-containing nanoconstructs.

In this example, iron oxide nanoparticles have been surface modified in a similar manner as MSNP using aforementioned methods with minor modification. Specifically, iron oxide nanoparticles (commercially available and FDA approved Ferumoxytol or Feraheme) were dispersed in ethanol solution and PEI (10 kDa) was added to the solution at a concentration 25 or 33 wt. % of PEI (10 kDa) per iron oxide. The mixture was subsequently shaken, centrifuged, and washed twice with PBS. Dry mal-PEG(5-kDa)-NHS was then added at a 1:1 ratio by mass of iron oxide to PEI in PBS. The resulting solution was shaken for two hours at room temperature, and was subsequently washed in PBS. Targeting agent (trastuzumab, T) was incorporated in the same manner as Example V. siRNA loading was achieved by mixing the resulting nanoconstructs with siRNA for 1 hour prior to characterization. The final hydrodynamic size of the nanoconstruct was approximately 50-100 nm in average as shown in FIG. 38A for material prepared with 25 wt. % PEI (called F1) or 33 wt. % PEI (called F2). The nanoconstructs exhibited a polydispersity index of less than 0.15 and a potential of about 10-20 mV as measured in water, which increased from −50 mV of the ION (Feraheme).

Example XXVI

Iron Oxide Nanoconstructs for siRNA Delivery and MRI Contrast Agent

Figure 38B:
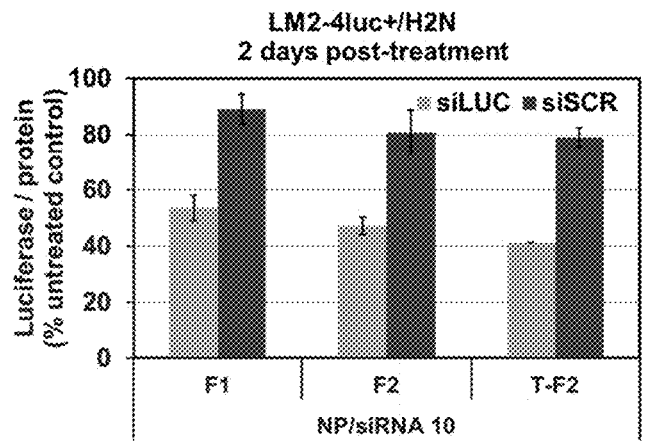

Nanoconstructs containing iron oxide nanoparticles can be used to deliver siRNA and achieve effective gene silencing. Iron oxide nanoconstructs synthesized by the method of Example XXV were loaded with 50 nM siLUC at a nanoconstruct per siLUC mass ratio of 10 and used to treat LM2-4luc+/H2N cells expressing luciferase similar to Example VIII. Good luciferase knock down efficacy (40-50%) was achieved as shown in FIG. 38B.

Figure 38C:
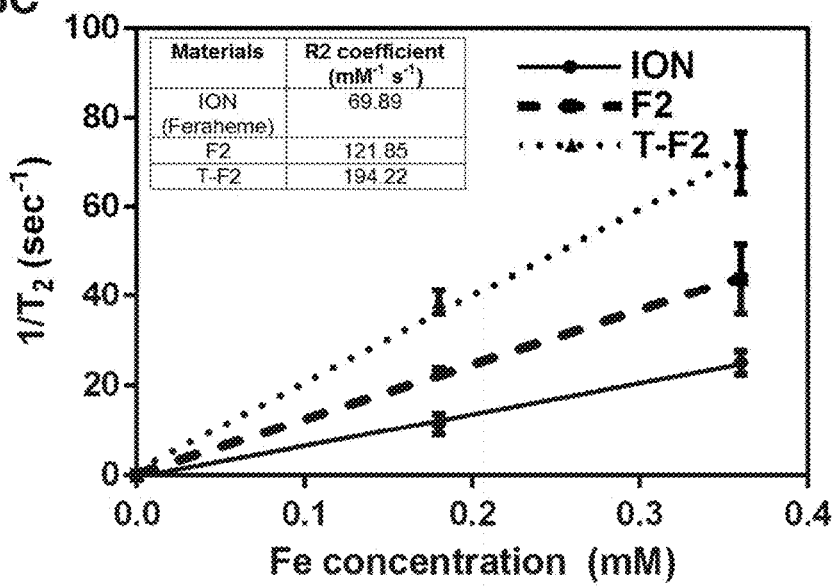

Iron oxide based nanoconstructs can serve as an MRI contrast agent. T2 relaxivity was calculated by T2 MRI (small animal Bruker BioSpin 11.75T MRI instrument (31 cm horizontal bore), Paravision 5.1 software) as increasing Fe concentrations in PBS. T2 values were found using ImageJ software and plotted as 1/T2 (1/s) vs Fe (mM) to yield relaxivity (R2 coefficient) as the slope (FIG. 38C). FIG. 38C shows that the final nanoconstruct T-F2 (conjugated with trastuzumab and loaded with siHER2) has 2-3 fold enhanced R2 coefficient, compared to unmodified ION (Ferumoxytol). Hence, the iron oxide nanoconstruct has the potential to serve as a diagnostic tool (MRI probe). In addition, since the materials are magnetic, they can potentially be used for magnetically guided delivery of therapeutics in vivo or in humans.

REFERENCES

A. Chaturvedi, S. K. Pierce, Traffic (Copenhagen, Denmark) 2009, 10, 621-628.

A. Mantei, S. Rutz, M. Janke, D. Kirchhoff, U. Jung, V. Patzel, U. Vogel, T. Rudel, I. Andreou, M. Weber, A. Scheffold, European journal of immunology 2008, 38, 2616-2625.

D. M. Dykxhoorn, D. Palliser, J. Lieberman, Gene therapy 2006, 13, 541-552.

C. Argyo, V. Weiss, C. Bräuchle, T. Bein, Chemistry of Materials 2013, 26, 435-451.

F. Tang, L. Li, D. Chen, Advanced Materials 2012, 24, 1504-1534.

G. Francia, C. Rodriguez, P. Xu, S. Man, W. Cruz-Munoz, G. Bocci, R. S. Kerbel, J Clin Oncol. 2012 ASCO Annual Meeting J. Tabernero, G. I. Shapiro, P. M. LoRusso, A. Cervantes, G. K. Schwartz, G. J. Weiss, L. Paz-Ares, D. C. Cho, J. R. Infante, M. Alsina, M. M. Gounder, R. Falzone, J. Harrop, A. C. S. White, I. Toudjarska, D. Bumcrot, R. E. Meyers, G. Hinkle, N. Svrzikapa, R. M. Hutabarat, V. A. Clausen, J. Cehelsky, S. V. Nochur, C. Gamba-Vitalo, A. K. Vaishnaw, D. W. Y. Sah, J. A. Gollob, H. A. Burris, Cancer Discovery 2013, 3, 406-417.

R. K. Ramanathan, S. I. Hamburg, M. J. Borad, M. Seetharam, M. N. Kundranda, P. Lee, P. Fredlund, M. Gilbert, C. Mast, S. C. Semple, A. D. Judge, B. Crowell, L. Vocila, I. MacLachlan, D. W. Northfelt, in AACR 104th Annual Meeting 2013, Washington, DC, 2013.

L. Pan, Q. He, J. Liu, Y. Chen, M. Ma, L. Zhang, J. Shi, Journal of the American Chemical Society 2012, 134, 5722-5725.

I. Slowing, B. G. Trewyn, S. Giri, V. S. Y. Lin, Advanced Functional Materials 2007, 17, 1225-1236.

M. Barok, H. Joensuu, J. Isola, Breast Cancer Research 2014, 16, 1-12.

A. A. Seyhan, U. Varadarajan, S. Choe, W. Liu, T. E. Ryan, Molecular bioSystems 2012, 8, 1553-1570.

M. E. Davis, J. E. Zuckerman, C. H. J. Choi, D. Seligson, A. Tolcher, C. A. Alabi, Y. Yen, J. D. Heidel, A. Ribas, Nature 2010, 464, 1067-1070.

M. E. Davis, Molecular pharmaceutics 2009, 6, 659-668.

P. Yousefpour, F. Atyabi, E. Vasheghani-Farahani, A. A. Movahedi, R. Dinarvand, International journal of nanomedicine 2011, 6, 1977-1990.

M. N. Koopaei, R. Dinarvand, M. Amini, H. Rabbani, S. Emami, S. N. Ostad, F. Atyabi, International journal of nanomedicine 2011, 6, 1903-1912.

R. Broering, C. I. Real, M. J. John, K. Jahn-Hofmann, L. M. Ickenstein, K. Kleinehr, A. Paul, K. Gibbert, U. Dittmer, G. Gerken, J. F. Schlaak, International Immunology 2014, 26, 35-46.

M. Zamanian-Daryoush, J. T. Marques, M. P. Gantier, M. A. Behlke, M. John, P. Rayman, J. Finke, B. R. Williams, Journal of interferon & cytokine research: the official journal of the International Society for Interferon and Cytokine Research 2008, 28, 221-233.

R. Kanasty, J. R. Dorkin, A. Vegas, D. Anderson, Nat Mater 2013, 12, 967-977.

D. Haussecker, Mol Ther Nucleic Acids 2012, 1, e8.

S. Ahmad, S. Gupta, R. Kumar, G. C. Varshney, G. P. S. Raghava, Sci. Rep. 2014, 4.

R. Nahta, F. J. Esteva, Breast cancer research: BCR 2006, 8, 215.

T. Bieber, W. Meissner, S. Kostin, A. Niemann, H. P. Elsasser, Journal of controlled release: official journal of the Controlled Release Society 2002, 82, 441-454.

K. Kunath, A. von Harpe, D. Fischer, H. Petersen, U. Bickel, K. Voigt, T. Kissel, Journal of controlled release: official journal of the Controlled Release Society 2003, 89, 113-125; cM. Breunig, U. Lungwitz, R. Liebl, C. Fontanari, J. Klar, A. Kurtz, T. Blunk, A. Goepferich, The journal of gene medicine 2005, 7, 1287-1298.

T. M. Allen, P. R. Cullis, Science 2004, 303, 1818-1822; bH. Kobayashi, R. Watanabe, P. L. Choyke, Theranostics 2013, 4, 81-89.

T.-M. Ketola, M. Hanzlíková, L. Leppanen, M. Ravina, C. J. Bishop, J. J. Green, A. Urtti, H. Lemmetyinen, M. Yliperttula, E. Vuorimaa-Laukkanen, The Journal of Physical Chemistry B 2013, 117, 10405-10413; bL. Aravindan, K. A. Bicknell, G. Brooks, V. V. Khutoryanskiy, A. C. Williams, Macromolecular bioscience 2013, 13, 1163-1173.

X. Li, Y. Chen, M. Wang, Y. Ma, W. Xia, H. Gu, Biomaterials 2013, 34, 1391-1401.

H. Meng, W. X. Mai, H. Zhang, M. Xue, T. Xia, S. Lin, X. Wang, Y. Zhao, Z. Ji, J. I. Zink, A. E. Nel, ACS Nano 2013, 7, 994-1005.

J. Shen, H. C. Kim, H. Su, F. Wang, J. Wolfram, D. Kirui, J. Mai, C. Mu, L. N. Ji, Z. W. Mao, H. Shen, Theranostics 2014, 4, 487-497;

D. Lin, Q. Cheng, Q. Jiang, Y. Huang, Z. Yang, S. Han, Y. Zhao, S. Guo, Z. Liang, A. Dong, Nanoscale 2013, 5, 4291-4301.

Y.-C. Wang, G. Morrison, R. Gillihan, J. Guo, R. Ward, X. Fu, M. Botero, N. Healy, S. Hilsenbeck, G. Phillips, G. Chamness, M. Rimawi, C. K. Osborne, R. Schiff, Breast Cancer Research 2011, 13, R121.

C. A. Ritter, M. Perez-Torres, C. Rinehart, M. Guix, T. Dugger, J. A. Engelman, C. L. Arteaga, Clinical Cancer Research 2007, 13, 4909-4919; cT. Cooke, J. Reeves, A. Lanigan, P. Stanton, Annals of oncology: official journal of the European Society for Medical Oncology/ESMO 2001, 12 Suppl 1, S23-28.

Z. Zhang, A. E. Berns, S. Willbold, J. Buitenhuis, Journal of colloid and interface science 2007, 310, 446-455.

R. Gref, M. Luck, P. Quellec, M. Marchand, E. Dellacherie, S. Harnisch, T. Blunk, R. H. Muller, Colloids and surfaces. B, Biointerfaces 2000, 18, 301-313.

C. G. Murphy, S. Modi, Biologics: targets & therapy 2009, 3, 289-301.

C. L. Warner, R. S. Addleman, A. D. Cinson, T. C. Droubay, M. H. Engelhard, M. A. Nash, W. Yantasee, M. G. Warner, ChemSusChem 2010, 3, 749-757.

C. M. Rudin, J. L. Marshall, C. H. Huang, H. L. Kindler, C. Zhang, D. Kumar, P. C. Gokhale, J. Steinberg, S. Wanaski, U. N. Kasid, M. J. Ratain, Clinical Cancer Research 2004, 10, 7244-7251.

C. Timchalk, M. G. Warner, Environ. Sci. Technol. 2007, 41, 5114-5119.

C. V. Pecot, G. A. Calin, R. L. Coleman, G. Lopez-Berestein, A. K. Sood, Nat Rev Cancer 2011, 11, 59-67.

D. W. Bartlett, H. Su, I. J. Hildebrandt, W. A. Weber, M. E. Davis, Proceedings of the National Academy of Sciences 2007, 104, 15549-15554.

F. Henjes, C. Bender, S. von der Heyde, L. Braun, H. A. Mannsperger, C. Schmidt, S. Wiemann, M. Hasmann, S. Aulmann, T. Beissbarth, U. Korf, Oncogenesis 2012, 1, e16.

G. J. Brewer, R. D. Dick, D. K. Grover, V. LeClaire, M. Tseng, M. Wicha, K. Pienta, B. G. Redman, T. Jahan, V. K. Sondak, M. Strawderman, G. LeCarpentier, S. D. Merajver, Clinical Cancer Research 2000, 6, 1-10.

H. Maeda, J. Wu, T. Sawa, Y. Matsumura, K. Hori, Journal of controlled release: official journal of the Controlled Release Society 2000, 65, 271-284.

H. Zhang, T. Xia, H. Meng, M. Xue, S. George, Z. Ji, X. Wang, R. Liu, M. Wang, B. France, R. Rallo, R. Damoiseaux, Y. Cohen, K. A. Bradley, J. I. Zink, A. E. Nel, ACS Nano 2011, 5, 2756-2769.

I. Beyer, H. Cao, J. Persson, M. Song, M. Richter, Q. Feng, R. Yumul, R. van Rensburg, Z. Li, R. Berenson, D. Carter, S. Roffler, C. Drescher, A. Lieber, Clinical cancer research: an official journal of the American Association for Cancer Research 2012, 18, 3340-3351.

I. Beyer, Z. Li, J. Persson, Y. Liu, R. van Rensburg, R. Yumul, X. B. Zhang, M. C. Hung, A. Lieber, Molecular therapy: the journal of the American Society of Gene Therapy 2011, 19, 479-489.

J. D. Heidel, Z. Yu, J. Y.-C. Liu, S. M. Rele, Y. Liang, R. K. Zeidan, D. J. Kornbrust, M. E. Davis, Proceedings of the National Academy of Sciences 2007, 104, 5715-5721.

J. E. Zuckerman, C. H. J. Choi, H. Han, M. E. Davis, Proceedings of the National Academy of Sciences 2012, 109, 3137-3142.

J. Lu, M. Liong, S. Sherman, T. Xia, M. Kovochich, A. E. Nel, J. I. Zink, F. Tamanoi, Nanobiotechnology: the journal at the intersection of nanotechnology, molecular biology, and biomedical sciences 2007, 3, 89-95.

J. Morry, W. Ngamcherdtrakul, S. Gu, S. M. Goodyear, D. J. Castro, M. M. Reda, T. Sangvanich, W. Yantasee, Biomaterials 2015, 66, 41-52.

J. M. du Manoir, G. Francia, S. Man, M. Mossoba, J. A. Medin, A. Viloria-Petit, D. J. Hicklin, U. Emmenegger, R. S. Kerbel, Clinical Cancer Research 2006, 12, 904-916.

K. A. Graham, M. Kulawiec, K. M. Owens, X. Li, M. M. Desouki, D. Chandra, K. K. Singh, Cancer Biology & Therapy 2010, 10, 223-231.

K. A. Whitehead, R. Langer, D. G. Anderson, Nature reviews. Drug discovery 2009, 8, 129-138.

K. Takeda, S. Akira, International Immunology 2005, 17, 1-14.

M. A. Poul, B. Becerril, U. B. Nielson, P. Morrisson, J. D. Marks, Journal of Molecular Biology 2000, 301, 1149-1161.

M. H. Schwenk, Pharmacotherapy 2010, 30, 70-79.

M. J. Roberts, M. D. Bentley, J. M. Harris, Advanced drug delivery reviews 2002, 54, 459-476.

O. Boussif, F. Lezoualc'h, M. A. Zanta, M. D. Mergny, D. Scherman, B. Demeneix, J. P. Behr, Proceedings of the National Academy of Sciences 1995, 92, 7297-7301.

R. A. Petros, J. M. DeSimone, Nature reviews. Drug discovery 2010, 9, 615-627.

R. M. Crist, J. H. Grossman, A. K. Patri, S. T. Stern, M. A. Dobrovolskaia, P. P. Adiseshaiah, J. D. Clogston, S. E. McNeil, Integrative biology: quantitative biosciences from nano to macro 2013, 5, 66-73.

R. Nahta, ISRN oncology 2012, 2012, 428062.

S. Gu, Z. Hu, W. Ngamcherdtrakul, D. J. Castro, J. Morry, M. M. Reda, J. W. Gray, W. Yantasee, Oncotarget 2016, DOI: 10.18632/oncotarget.7409.

S. Guo, L. Huang, Journal of Nanomaterials 2011, 2011, 12.

S. Mao, M. Neu, O. Germershaus, O. Merkel, J. Sitterberg, U. Bakowsky, T. Kissel, Bioconjugate chemistry 2006, 17, 1209-1218.

T. H. Chung, S. H. Wu, M. Yao, C. W. Lu, Y. S. Lin, Y. Hung, C. Y. Mou, Y. C. Chen, D. M. Huang, Biomaterials 2007, 28, 2959-2966.

W. Li, F. Nicol, F. C. Szoka Jr., Advanced Drug Delivery Review 2004, 56, 967-985.

W. Ngamcherdtrakul, J. Morry, S. Gu, D. J. Castro, S. M. Goodyear, T. Sangvanich, M. M. Reda, R. Lee, S. A. Mihelic, B. L. Beckman, Z. Hu, J. W. Gray, W. Yantasee, Advanced Functional Materials 2015, 25, 2646-2659.

W. Yantasee, C. L. Warner, T. Sangvanich, R. S. Addleman, T. G. Carter, R. J. Wiacek, G. E. Fryxell, C. Timchalk, M. G. Warner, Environmental Science & Technology 2007, 41, 5114-5119.

The invention is further described in the following numbered embodiments:

Embodiment 1. A multilayer nanoconstruct comprising a cationic polymer bound to an exterior surface of a nanoparticle, wherein the cationic polymer is cross-linked.

Embodiment 2. The nanoconstruct of embodiment 1, further comprising a stabilizer bound to the cationic polymer or nanoparticle, wherein the stabilizer prevents aggregation of the nanoconstruct in solution.

Embodiment 3. The nanoconstruct of embodiment 1 or 2, wherein the nanoparticle is mesoporous.

Embodiment 4. The nanoconstruct of any one of embodiments 1-3, wherein the nanoparticle is a silica nanoparticle, a silicon nanoparticle, an iron oxide nanoparticle, a gold nanoparticle, a silver nanoparticle, or a carbon nanotube.

Embodiment 5. The nanoconstruct of any one of embodiments 1-4, wherein the nanoconstruct has a hydrodynamic diameter of from about 10 to about 200 nm.

Embodiment 6. The nanoconstruct of embodiment 5, wherein the nanoparticle has a diameter of 5 to 90 nm.

Embodiment 7. The nanoconstruct of any one of embodiments 1-6, wherein the cationic polymer is from about 5% to about 30% by weight of the nanoconstruct.

Embodiment 8. The nanoconstruct of embodiment 7, wherein the cationic polymer is from about 10% to about 25% by weight of the nanoconstruct.

Embodiment 9. The nanoconstruct of any one of embodiments 1-8, wherein the cationic polymer is selected from the group consisting of polyethylenimine, chitosan, polypropyleneimine, polylysine, polyamidoamine, poly(allylamine), poly(diallyldimethylammonium chloride), poly(N-isopropyl acrylamide-co-acrylamide), poly(N-isopropyl acrylamide-co-acrylic acid), diethylaminoethyl-dextran, poly-(N-ethylvinylpyridinium bromide), poly(dimethylamino)ethyl methacrylate, and/or poly(ethylene glycol)-co-poly (trimethylaminoethylmethacrylate chloride).

Embodiment 10. The nanoconstruct of embodiment 9, wherein the cationic polymer is polyethylenimine having a molecular weight of from about 0.8 kDa to about 10 kDa.

Embodiment 11. The nanoconstruct of any one of embodiments 1-10, wherein the cationic polymer is cross-linked by reacting cationic polymer on the surface of the nanoparticle with a cross-linker in the presence of cationic polymer in solution.

Embodiment 12. The nanoconstruct of any one of embodiments 2-11, wherein the stabilizer is from about 1% to about 30% by weight of the nanoconstruct.

Embodiment 13. The nanoconstruct of embodiment 12, wherein the stabilizer is from about 5% to about 25% by weight of the nanoconstruct.

Embodiment 14. The nanoconstruct of any one of embodiments 2-13, wherein the stabilizer is selected from the group consisting of polyethylene glycol, dextran, polysialic acid, hyaluronic acid (HA), polyvinyl pyrrolidone (PVP), polyvinyl alcohol (PVA), and/or polyacrylamide (PAM).

Embodiment 15. The nanoconstruct of embodiment 14, wherein the stabilizer is polyethylene glycol having a molecular weight of from about 1 kDa to about 20 kDa.

Embodiment 16. The nanoconstruct of any one of embodiments 1-15, further comprising at least one type of oligonucleotide electrostatically bound to the cationic polymer.

Embodiment 17. The nanoconstruct of embodiment 16, wherein the at least one type of oligonucleotide is a siRNA, miRNA, miRNA mimic, or antisense oligomer.

Embodiment 18. The nanoconstruct of embodiment 16 or 17, wherein the at least one type of oligonucleotide is siRNA.

Embodiment 19. The nanoconstruct of embodiment 18, wherein the siRNA targets one or more genes selected from the group consisting of HER2, AKT1, AKT2, AKT3, EPS8L1, GRB7, AR, Myc, VEGF, VEGF-R1, RTP801, proNGF, Keratin K6A, Bcl-2, PLK1, LMP2, LMP7, MECL1, RRM2, PKN3, Survivin, HIF1α, Furin, KSP, eiF-4E, p53, β-catenin, ApoB, PCSK9, HSP47, CFTR, CTGF, SNALP, RSV nucleocapsids, CD47, PD-L1, and CTLA-4.

Embodiment 20. The nanoconstruct of any one of embodiments 16-19, wherein the at least one type of oligonucleotide is from about 1% to about 15% by weight of the nanoconstruct.

Embodiment 21. The nanoconstruct of embodiment 20, wherein the at least one type of oligonucleotide is from about 1% to about 5% by weight of the nanoconstruct.

Embodiment 22. The nanoconstruct of any one of embodiments 16-21, wherein the at least one type of oligonucleotide comprises two or more different siRNAs loaded onto the nanoconstruct.

Embodiment 23. The nanoconstruct of any one of embodiments 1-22, further comprising a small molecule or a protein.

Embodiment 24. The nanoconstruct of embodiment 23, wherein the small molecule is from about 0.5% to about 30% by weight of the nanoconstruct.

Embodiment 25. The nanoconstruct of embodiment 23 or 24, wherein the small molecule is a chemotherapeutic agent, small molecule inhibitor, or a polypeptide.

Embodiment 26. The nanoconstruct of embodiment 23 or 24, wherein the small molecule is a label.

Embodiment 27. The nanoconstruct of embodiment 26, wherein the label is a lanthanide, a fluorescent dye, a gold nanoparticle, a quantum dot, a positron emission tomography (PET) tracer, and/or a magnetic resonance imaging (MRI) contrast agent.

Embodiment 28. The nanoconstruct of embodiment 23, wherein the protein is a cytokine.

Embodiment 29. The nanoconstruct of any one of embodiments 1-28, further comprising a targeting agent.

Embodiment 30. The nanoconstruct of embodiment 29, wherein the targeting agent is an antibody, a scFv antibody, an affibody, an aptamer, a peptide, and/or small targeting molecule.

Embodiment 31. The nanoconstruct of embodiment 29 or 30, wherein the targeting agent is from about 0.1% to about 10% by weight of the nanoconstruct.

Embodiment 32. The nanoconstruct of embodiment 31, wherein the targeting agent is from about 0.3% to about 5% by weight of the nanoconstruct.

Embodiment 33. The nanoconstruct of any one of embodiment 30-32, wherein the small targeting molecule is a carbohydrate or ligand.

Embodiment 34. The nanoconstruct of any one of embodiments 1-33, wherein the nanoconstruct is lyophilized.

Embodiment 35. The nanoconstruct of embodiment 34, wherein the nanoconstruct is lyophilized with trehalose.

Embodiment 36. The nanoconstruct of embodiment 35, wherein the trehalose is from about 1% to about 10% by weight of the nanoconstruct.

Embodiment 37. The nanoconstruct of any one of embodiments 1-36, wherein the exterior surface of the nanoparticle comprises thiol, amine, carboxylate, and/or phosphonate functional groups.

Embodiment 38. A method of delivering an agent to a site in a human or other mammalian subject comprising administering an effective amount of the nanoconstruct of any one of embodiments 1-37 comprising the agent to the human or other mammalian subject under conditions to deliver the nanoconstruct to the site.

Embodiment 39. The method of embodiment 38, wherein the site is a cell.

Embodiment 40. The method of embodiment 39, wherein the nanoconstruct is administered under conditions that the nanoconstruct is internalized by the cell.

Embodiment 41. The method of any one of embodiments 38-40, wherein the subject is suffering from a disease or condition characterized by over-expression of one or more genes relative to expression of the one or more genes in a healthy subject.

Embodiment 42. The method of embodiment 41, wherein the disease or condition is selected from the group consisting of AMD, macular edema, chronic optic nerve atrophy, pachyonychia congenital, chronic lymphocytic leukemia, metastatic lymphoma, metastatic cancer, solid tumors, acute kidney injury, delayed graft function, familia adenomatous polyposis, hypercholesterolemia, liver fibrosis, cystic fibrosis, dermal scarring, Ebola infection, RSV infection, and inflammation.

Embodiment 43. The method of embodiment 41 or 42, wherein the nanoconstruct is administered in an amount sufficient to treat the subject having the disease or condition.

Embodiment 44. The method of any one of embodiments 38-43, wherein the agent is a label.

Embodiment 45. The method of embodiment 44, wherein the label is a lanthanide, a fluorescent dye, a PET tracer, or a MRI contrast agent.

Embodiment 46. The method of any one of embodiments 38-43, wherein the agent is a therapeutic agent.

Embodiment 47. The method of embodiment 46, wherein the therapeutic agent is a nucleic acid capable of modulating expression of a target protein.

Embodiment 48. The method of embodiment 47, wherein the nucleic acid is a siRNA, miRNA, miRNA mimic, or antisense oligomer, and expression of the target protein is reduced.

Embodiment 49. The method of embodiment 46, wherein the therapeutic agent is a chemotherapeutic agent, a small molecule inhibitor, an antibody, a peptide, and/or a cytokine.

Embodiment 50. The method of any one of embodiments 38-49, wherein the subject is diagnosed with cancer, and the effective amount is a therapeutically effective amount.

Embodiment 51. The method of embodiment 50, wherein the cancer is resistant to a monoclonal antibody or a small molecule inhibitor.

Embodiment 52. The method of embodiment 51, wherein the therapeutic agent is an oligonucleotide that targets expression of a protein inhibited by the monoclonal antibody or the small molecule inhibitor.

Embodiment 53. The method of any one of embodiments 38-52, wherein the nanoconstruct further comprises a targeting agent.

Embodiment 54. The method of embodiment 53, wherein the targeting agent is an antibody, a scFv antibody, an affibody, an aptamer, a peptide, and/or small targeting molecule.

Embodiment 55. The method of any one of embodiments 38-54, wherein the subject is diagnosed with or is at risk for fibrosis or inflammation.

Embodiment 56. The method of any one of embodiments 38-55, wherein the nanoconstruct reduces reactive oxygen species, bioavailable copper, and/or NOX expression level in the subject, Embodiment 57. The method of any one of embodiments 38-56, wherein the agent is administered in an amount sufficient to reduce tumor migration or inflammation in the human or other mammalian subject.

Embodiment 58. The method of any one of embodiments 38-57, wherein the nanoconstruct modulates an adverse effect of one or more cytokines.

Embodiment 59. The method of any one of embodiments 38-58, wherein the nanoconstruct is administered subcutaneously, topically, systemically, intravesically, orally, intratumorally, or intraperitoneally.

Embodiment 60. A method of making a nanoconstruct comprising: providing a nanoparticle coated with a cationic polymer, and cross-linking the cationic polymer to make the nanoconstruct.

Embodiment 61. The method of embodiment 60, wherein the nanoparticle is a silica nanoparticle, a silicon nanoparticle, an iron oxide nanoparticle, a gold nanoparticle, a silver nanoparticle, or a carbon nanotube.

Embodiment 62. The method of embodiment 60 or 61, wherein the cationic polymer is cross-linked in the presence of free cationic polymer.

Embodiment 63. The method of embodiment 62, wherein the cationic polymer is cross-linked in the presence of a stoichiometric excess of the free cationic polymer.

Embodiment 64. The method of any one of embodiments 60-63, wherein the cationic polymer is selected from the group consisting of polyethylenimine, chitosan, polypropyleneimine, polylysine, polyamidoamine, poly(allylamine), poly(diallyldimethylammonium chloride), poly(N-isopropyl acrylamide-co-acrylamide), poly(N-isopropyl acrylamide-co-acrylic acid), diethylaminoethyl-dextran, poly-(N-ethyl-vinylpyridinium bromide), poly(dimethylamino)ethyl methacrylate, and/or poly(ethylene glycol)-co-poly(trimethylaminoethylmethacrylate chloride).

Embodiment 65. The method of embodiment 64, wherein the cationic polymer is polyethylenimine having a molecular weight of from about 0.8 kDa to about 10 kDa.

Embodiment 66. The method of any one of embodiments 60-65, wherein the cationic polymer is cross-linked using dithiobis[succinimidyl propionate] (DSP), 3, 3'-dithiobis(sulfosuccinimidyl propionate (DTSSP), or dimethyl 3, 3'-dithiobispropionimidate (DTBP).

Embodiment 67. The method of embodiment 66, wherein the cationic polymer is cross-linked using DSP.

Embodiment 68. The method of any one of embodiments 60-67, further comprising attaching a stabilizer to the nanoconstruct.

Embodiment 69. The method of embodiment 68, wherein the stabilizer is selected from the group consisting of polyethylene glycol, dextran, polysialic acid, HA, PVP, PVA, and PAM.

Embodiment 70. The method of embodiment 69, wherein the stabilizer is polyethylene glycol having a molecular weight of from about 1 kDa to about 20 kDa.

Embodiment 71. The method of embodiment 70, wherein the method comprises incubating maleimide-polyethylene glycol-N-hydroxysuccinimidyl ester (Mal-PEG-NHS) with the nanoconstruct at a weight ratio of from about 0.5:1 to about 5:1.

Embodiment 72. The method of any one of embodiments 60-71, further comprising attaching a targeting agent to the nanoconstruct.

Embodiment 73. The method of any one of embodiments 60-72, further comprising admixing the nanoconstruct with at least one type of oligonucleotide that binds noncovalently to the cationic polymer.

Embodiment 74. The method of embodiment 73, wherein the at least one type of oligonucleotide is a siRNA, miRNA, miRNA mimic, or antisense oligomer.

Embodiment 75. The method of any one of embodiments 60-74, further comprising admixing a small molecule or protein with the nanoparticle or the nanoconstruct so that the small molecule or protein binds to the nanoconstruct.

Embodiment 76. The method of embodiment 75, wherein the small molecule or protein is a chemotherapeutic agent, a label, a peptide, and/or a cytokine.

Embodiment 77. The method of any one of embodiments 60-76, further comprising lyophilizing the nanoconstruct.

Embodiment 78. The method of embodiment 77, wherein the nanoconstruct is lyophilized with trehalose.

Embodiment 79. A method of labeling a target comprising contacting the nanoconstruct of any one of embodiments 1-37 with the target under conditions to bind the nanoconstruct to the target.

Embodiment 80. The method of embodiment 79, wherein the target is a cell or protein.

Embodiment 81. The method of embodiment 80, wherein the nanoconstruct is internalized by the cell.

Embodiment 82. The method of embodiment 80 or 81, wherein the nanoconstruct binds to the exterior of the cell.

Embodiment 83. The method of any one of embodiments 79-82, wherein the label is a lanthanide, a fluorescent dye, a gold nanoparticle, a quantum dot, a PET tracer, and/or a MRI contrast agent.

Embodiment 84. The method of any one of embodiments 79-83, further comprising quantifying the amount of target by detecting the label after the nanoconstruct binds to the target.

Embodiment 85. The method of any one of embodiments 79-84, further comprising administering the labeled target to a subject and detecting the location of the target after the administering.

Embodiment 86. The method of any one of embodiments 79-85, wherein the nanoconstruct further comprises a therapeutic agent.

Embodiment 87. The method of embodiment 84 or 85, wherein the detecting is by fluorescence, magnetic resonance, or PET.

Embodiment 88. The method of any one of embodiments 79-87, wherein the nanoparticles is an iron oxide nanoparticle.

We claim:

1. A composition comprising:
   a plurality of multilayer nanoconstructs each comprising:
   about 10% to about 30% by weight cross-linked polyethylenimine (PEI) bound to an exterior surface of a silica nanoparticle, a silicon nanoparticle, an iron oxide nanoparticle, a silver nanoparticle, or a carbon nanotube; and
   polyethylene glycol (PEG) bound to the PEI or to the nanoparticle;
   wherein the nanoconstructs have a hydrodynamic size Z-average diameter of about 200 nm or less; and the plurality of nanoconstructs have a polydispersity index (PDI) of no more than about 0.37; and
   an oligonucleotide non-covalently attached to the PEI.

2. The composition of claim 1, wherein the silica nanoparticle is a mesoporous silica nanoparticle (MSNP).

3. The composition of claim 1, wherein the nanoparticles consist essentially of material(s) selected from the group consisting of: silica, silicon, iron oxide, silver, a carbon nanotube, and a combination of two or more thereof.

4. The composition of claim 1, wherein the multilayer nanoconstructs each comprise an iron oxide nanoparticle.

5. The composition of claim 1, wherein the PEI is crosslinked using a cleavable crosslinker.

6. The composition of claim 1, wherein the PEI has an average size of 1.8 to 25 kDa.

7. The composition of claim 1, wherein the nanoparticle is from about 5 nm to about 90 nm in diameter.

8. The composition of claim 1, wherein the hydrodynamic size Z-average diameter of the nanoconstructs is about 80 nm to about 200 nm, or is about 90 nm to about 120 nm.

9. The composition of claim 1, wherein the oligonucleotide comprises at least one of siRNA, miRNA, an miRNA mimic, DNA, or an antisense oligomer.

10. The composition of claim 1, wherein the oligonucleotide comprises siRNA.

11. The composition of claim 1, wherein the PDI of the nanoconstructs is about 0.22.

12. The composition of claim 1, wherein the hydrodynamic diameter of the nanoconstructs loaded with the oligonucleotide is about 200 nm or less.

13. The composition of claim 1, wherein the PDI of the nanoconstructs loaded with the oligonucleotide is no more than about 0.2.

14. The composition of claim 1, wherein the nanoconstructs further comprise one or more of: a small molecule, a protein, or a targeting agent.

15. The composition of claim 14, wherein the small molecule comprises: a chemotherapeutic agent, a small molecule inhibitor, a label, or a polypeptide.

16. The composition of claim 14, wherein the targeting agent comprises one or more of: an antibody, a scFv antibody, an affibody, an aptamer, a ligand, a carbohydrate, a peptide, or a small targeting molecule.

17. The composition of claim 1, further comprising a label attached to the nanoconstructs.

18. The composition of claim 17, wherein the label comprises at least one of a lanthanide, a fluorescent dye, a gold nanoparticle, a quantum dot, a PET tracer, or a MRI contrast agent.

19. A method of labeling a target comprising contacting the composition of claim 18 with the target under conditions to bind the nanoconstruct to the target.

20. The method of claim 19, wherein the contacting occurs ex vivo.

21. The method of claim 19, wherein the contacting occurs in vivo in a subject.

22. The method of claim 19, wherein the label comprises at least one of a lanthanide, a fluorescent dye, a gold nanoparticle, a quantum dot, a PET tracer, or a MRI contrast agent.

23. The method of claim 19, further comprising at least one of:
   (1) quantifying the amount of target by detecting the label after the nanoconstruct binds to the target;
   (2) administering the labeled nanoconstruct to a subject; and detecting a location of the label after the administering; or
   (3) administering the labeled target to a subject; and detecting a location of the labeled target after the administering.

24. A method of delivering an oligonucleotide to a site in a human or other mammalian subject, the method comprising administering an effective amount of the composition of claim 1 to the human or other mammalian subject under conditions to deliver the nanoconstruct to the site.

25. The method of claim 24, wherein the site is a cell, or the site is a tumor.

26. The method of claim 25, wherein the nanoconstruct is administered under conditions that the nanoconstruct is internalized by the cell, or by a cancer or non-cancer cell within the tumor.

27. The method of claim 24, wherein the oligonucleotide modulates expression of a target protein.

28. The method of claim 24, wherein the subject is diagnosed with cancer or diagnosed with or is at risk for fibrosis or inflammation, and the effective amount is a therapeutically effective amount.

29. The method of claim 24, wherein the nanoconstruct further comprises a targeting agent.

30. The method of claim 24, wherein the nanoconstruct reduces reactive oxygen species, bioavailable copper, and/or NOX expression level in the subject or modulates an adverse effect of one or more cytokines.

* * * * *

SEQUENCE LISTING

```
<160> NUMBER OF SEQ ID NOS: 8

<210> SEQ ID NO 1
<211> LENGTH: 23
<212> TYPE: RNA
<213> ORGANISM: Artificial Sequence
<220> FEATURE:
<223> OTHER INFORMATION: Synthetic Construct

<400> SEQUENCE: 1
cacguuugag uccaugccca auu                                              23

<210> SEQ ID NO 2
<211> LENGTH: 23
<212> TYPE: RNA
<213> ORGANISM: Artificial Sequence
<220> FEATURE:
<223> OTHER INFORMATION: Synthetic Construct
```

```
<400> SEQUENCE: 2
uugggcaugg acucaaacgu guu                                          23

<210> SEQ ID NO 3
<211> LENGTH: 21
<212> TYPE: DNA
<213> ORGANISM: Artificial Sequence
<220> FEATURE:
<223> OTHER INFORMATION: Synthetic Construct

<400> SEQUENCE: 3
cggauuacca gggauuucat t                                            21

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
ugaaaucccu gguaauccgt t                                            21

<210> SEQ ID NO 5
<211> LENGTH: 19
<212> TYPE: RNA
<213> ORGANISM: Artificial Sequence
<220> FEATURE:
<223> OTHER INFORMATION: Synthetic Construct

<400> SEQUENCE: 5
ugguuuacau gucgacuaa                                               19

<210> SEQ ID NO 6
<211> LENGTH: 19
<212> TYPE: RNA
<213> ORGANISM: Artificial Sequence
<220> FEATURE:
<223> OTHER INFORMATION: Synthetic Construct

<400> SEQUENCE: 6
uuagucgaca uguaaacca                                               19

<210> SEQ ID NO 7
<211> LENGTH: 25
<212> TYPE: RNA
<213> ORGANISM: Artificial Sequence
<220> FEATURE:
<223> OTHER INFORMATION: Synthetic Construct

<400> SEQUENCE: 7
auucaguuuc acauugcuug gugac                                        25

<210> SEQ ID NO 8
<211> LENGTH: 27
<212> TYPE: RNA
<213> ORGANISM: Artificial Sequence
<220> FEATURE:
<223> OTHER INFORMATION: Synthetic Construct

<400> SEQUENCE: 8
gucaccaaga acugugacac agaaggg                                      27
```